US010716631B2

(12) United States Patent
Tolkowsky

(10) Patent No.: US 10,716,631 B2
(45) Date of Patent: Jul. 21, 2020

(54) APPARATUS AND METHODS FOR USE WITH SKELETAL PROCEDURES

(71) Applicants: Vuze Medical Ltd., Tel Aviv (IL); David Tolkowsky, Tel Aviv (IL)

(72) Inventor: David Tolkowsky, Tel Aviv (IL)

(73) Assignee: Vuze Medical Ltd., Tel Aviv (IL)

(*) Notice: Subject to any disclaimer, the term of this patent is extended or adjusted under 35 U.S.C. 154(b) by 181 days.

(21) Appl. No.: 16/083,247

(22) PCT Filed: Mar. 13, 2017

(86) PCT No.: PCT/IL2017/050314
§ 371 (c)(1),
(2) Date: Sep. 7, 2018

(87) PCT Pub. No.: WO2017/158592
PCT Pub. Date: Sep. 21, 2017

(65) Prior Publication Data
US 2019/0350657 A1 Nov. 21, 2019

Related U.S. Application Data

(60) Provisional application No. 62/307,514, filed on Mar. 13, 2016, provisional application No. 62/334,463, (Continued)

(51) Int. Cl.
*A61B 5/05* (2006.01)
*G06K 9/00* (2006.01)
(Continued)

(52) U.S. Cl.
CPC ............... *A61B 34/20* (2016.02); *A61B 6/12* (2013.01); *A61B 6/4441* (2013.01); *A61B 6/466* (2013.01);
(Continued)

(58) Field of Classification Search
USPC ........ 382/100, 103, 106–107, 128–134, 154, 382/162, 168, 174, 181, 190, 199, 219, (Continued)

(56) References Cited

U.S. PATENT DOCUMENTS 4,905,267 A 2/1990 Miller et al.
4,985,019 A 1/1991 Michelson
(Continued)

FOREIGN PATENT DOCUMENTS

EP 1504726 2/2005
WO 2016/113165 7/2016
(Continued)

OTHER PUBLICATIONS

"3-D Imaging Techniques Transform Cardiac Catheterization," UCLA Health (Jan. 1, 2014).
(Continued)

*Primary Examiner* — Seyed H Azarian
(74) *Attorney, Agent, or Firm* — Fish & Richardson P.C.

(57) ABSTRACT

Apparatus for performing a procedure using a tool configured to be advanced into a skeletal portion within a body of a subject along a longitudinal insertion path, and for use with:
 (a) a 3D imaging device configured to acquire 3D image data of the skeletal portion.
 (b) a 2D x-ray imaging device that is unregistered with respect to the subject's body and configured, while a portion of the tool is disposed at a first location along the longitudinal insertion path.

12 Claims, 21 Drawing Sheets

Related U.S. Application Data filed on May 11, 2016, provisional application No. 62/362,607, filed on Jul. 15, 2016, provisional application No. 62/398,085, filed on Sep. 22, 2016, provisional application No. 62/439,495, filed on Dec. 28, 2016, provisional application No. 62/463,747, filed on Feb. 27, 2017.

(51) Int. Cl.

| | |
|---|---|
| A61B 34/20 | (2016.01) |
| A61B 46/20 | (2016.01) |
| A61B 6/12 | (2006.01) |
| A61B 6/00 | (2006.01) |
| A61B 90/00 | (2016.01) |
| A61B 8/00 | (2006.01) |
| G06T 15/06 | (2011.01) |
| G06T 15/08 | (2011.01) |
| A61B 34/30 | (2016.01) |
| G06T 7/30 | (2017.01) |

(52) U.S. Cl.
CPC ............ *A61B 6/505* (2013.01); *A61B 6/5223* (2013.01); *A61B 6/5241* (2013.01); *A61B 6/5247* (2013.01); *A61B 6/5264* (2013.01); *A61B 6/584* (2013.01); *A61B 8/4416* (2013.01); *A61B 46/20* (2016.02); *A61B 90/36* (2016.02); *A61B 90/39* (2016.02); *G06T 15/06* (2013.01); *G06T 15/08* (2013.01); *A61B 34/30* (2016.02); *A61B 2034/2055* (2016.02); *A61B 2090/364* (2016.02); *A61B 2090/376* (2016.02); *A61B 2090/395* (2016.02); *A61B 2090/3966* (2016.02); *A61B 2090/3995* (2016.02); *G06T 7/30* (2017.01); *G06T 2207/10072* (2013.01); *G06T 2207/10124* (2013.01); *G06T 2207/30012* (2013.01)

(58) Field of Classification Search
USPC ....... 382/224, 254, 274, 276, 285–291, 305, 382/312; 600/424, 426; 378/4, 21
See application file for complete search history.

(56) References Cited

U.S. PATENT DOCUMENTS

| | | | |
|---|---|---|---|
| 6,782,287 B2 | 8/2004 | Grzeszczuk et al. | |
| 7,570,791 B2 | 8/2009 | Frank et al. | |
| 7,853,311 B1 | 12/2010 | Webb | |
| 8,036,441 B2 | 10/2011 | Frank et al. | |
| 8,463,010 B2 | 6/2013 | Batman et al. | |
| 9,240,046 B2 | 1/2016 | Carrell et al. | |
| 9,262,830 B2 | 2/2016 | Bakker et al. | |
| 9,427,286 B2 | 8/2016 | Siewerdsen et al. | |
| 2003/0130576 A1* | 7/2003 | Seeley ................. | A61B 6/4441 600/426 |
| 2004/0103903 A1 | 6/2004 | Falahee | |
| 2004/0127824 A1 | 7/2004 | Falahee | |
| 2009/0274271 A1 | 11/2009 | Pfister et al. | |
| 2010/0106010 A1 | 4/2010 | Rubner et al. | |
| 2010/0161022 A1 | 6/2010 | Tolkowsky | |
| 2012/0230565 A1 | 9/2012 | Steinberg et al. | |
| 2012/0289826 A1 | 11/2012 | Graumann et al. | |
| 2015/0043798 A1 | 2/2015 | Carrell et al. | |
| 2015/0085981 A1 | 3/2015 | Siewerdsen et al. | |
| 2015/0150523 A1 | 6/2015 | Sirpad et al. | |
| 2015/0201892 A1 | 7/2015 | Hummel et al. | |
| 2015/0282889 A1* | 10/2015 | Cohen .................... | A61B 34/10 600/424 |
| 2016/0100911 A1 | 4/2016 | O'Neill | |
| 2016/0191887 A1 | 6/2016 | Casas | |
| 2016/0374764 A1 | 12/2016 | Kemp et al. | |
| 2017/0084022 A1 | 3/2017 | Naidu et al. | |
| 2017/0128041 A1 | 5/2017 | Hasser et al. | |
| 2017/0156800 A1 | 6/2017 | Brown | |
| 2017/0164920 A1* | 6/2017 | Lavallee ............... | A61B 6/5235 |
| 2017/0165008 A1 | 6/2017 | Finley | |
| 2017/0258533 A1* | 9/2017 | Crawford ............... | A61B 10/02 |
| 2020/0053335 A1* | 2/2020 | Casas ................... | H04N 13/239 |

FOREIGN PATENT DOCUMENTS

| | | |
|---|---|---|
| WO | 2017/106357 | 6/2017 |
| WO | WO 2018/129532 | 7/2018 |

OTHER PUBLICATIONS

"CARESTREAM DirectView DR Long-Length Imaging System with Automatic and Manual Stitching," Carestream Health (2012).
Abe et al., "A novel 3D guidance system using augmented reality for percutaneous vertebroplasty," Journal of Neurosurgery: Spine 19.4 (2013): 492-501.
Anderst et al., "Six-Degrees-of-Freedom Cervical Spine Range of Motion During Dynamic Flexion-Extension After Single-Level Anterior Arthrodesis," The Journal of Bone and Joint Surgery. American vol. 95.6 (2013): 497.
Bifulco et al., "Simulation of the radiography formation process from CT patient volume." (1998).
Chang et al., "Registration of 2D C-Arm and 3D CT Images for a C-Arm Image-Assisted Navigation System for Spinal Surgery," Applied Bionics and Biomechanics (2015).
Chen et al., "Ruler based automatic C-arm image stitching without overlapping constraint," Roboter-Assistenten werden sensitiv.: 212-215 (2015).
Cheng et al., "Deep similarity learning for multimodal medical images," Computer Methods in Biomechanics and Biomedical Engineering: Imaging & Visualization 6.3 (2016).
De Silva et al., "Development and Clinical Translation of the "LevelCheck" Registration Algorithm for Decision Support in Spine Surgery," presented at Radiological Society of North America (RSNA) 2016 annual meeting, Nov. 29, 2016.
Elmi-Terander et al., "Surgical Navigation Technology Based on Augmented Reality and Integrated 3D Intraoperative Imaging" Spine 41.21 (2016): E1303.
Freiman et al., "Spectral-based 2D/3D X-ray to CT image rigid registration," Medical Imaging 2011: Visualization, Image-Guided Procedures, and Modeling. vol. 7964. International Society for Optics and Photonics, 2011.
Glocker, "Automatic Localization and Identification of Vertebrae in Arbitrary Field-of-View CT Scans," International Conference on Medical Image Computing and Computer-Assisted Intervention. Springer, Berlin, Heidelberg, 2012.
Goerres et al., "Deformable 3D-2D Registration for Guiding K-Wire Placements in Pelvic Trauma Surgery," Medical Imaging 2017: Image-Guided Procedures, Robotic Interventions, and Modeling. vol. 10135. International Society for Optics and Photonics, 2017.
Gooßen et al., "Automatic stitching of digital radiographies using image interpretation," Proceedings of the 5th International Conference on Image Analysis and Recognition. Berlin: Springer Verlag. 2008.
Gooßen et al., "Ruler-based automatic stitching of spatially overlapping radiographs," Bildverarbeitung für die Medizin 2008. Springer, Berlin, Heidelberg, 2008. 192-196.
Gottesfeld Brown et al., "Registration of Planar Film Radiographs with Computed Tomography," mmbia. IEEE, 1996.
Hart et al., "Reduction of radiation exposure by the use of fluoroscopic guidance in transpendicular instrumentation," Acta chirurgiae orthopaedicae et traumatologiae Cechoslovaca 78.5 (2011): 447-450.—abstract.
Jonic et al., "Multiresolution spline-based 3D/2D registration of CT volume and C-arm images for computer-assisted surgery," Medical Imaging 2001: Image Processing. vol. 4322. International Society for Optics and Photonics, 2001.
Joskowicz, "Computer Assisted Surgery Lectures Fluoro X-ray to CT rigid registration," School of Engineering and Computer Science the Hebrew University of Jerusalem, Israel. 2009.

(56) References Cited

OTHER PUBLICATIONS

Markelj et al., "A review of 3D/2D registration methods for image-guided interventions," Medical image analysis 16.3 (2012): 642-661.
Otake et al., "Intraoperative Image-based Multiview 2D/3D Registration for Image-Guided Orthopaedic Surgery: Incorporation of FiducialBased C-Arm Tracking and GPU-Acceleration," IEEE transactions on medical imaging 31.4 (2012): 948-962.
Otake et al., "Automatic Localization of Vertebral Levels in X-Ray Fluoroscopy Using 3D-2D Registration: A Tool to Reduce Wrong-Site Surgery," Phys Med Biol, Sep. 2012, 7(17): 5485-5508.
Rohlfing et al., "Progressive attenuation fields: Fast 2D-3D image registration without precomputation," Medical Physics 32.9 (2005): 2870-2880.
Russakoff et al., "Fast Intensity-based 2D-3D Image Registration of Clinical Data Using Light Fields," null. IEEE, 2003.
Russakoff et al., "Fast calculation of digitally reconstructed radiographs using light fields," Medical Imaging 2003: Image Processing. vol. 5032. International Society for Optics and Photonics, 2003.
Russakoff et al., "Fast Generation of Digitally Reconstructed Radiographs Using Attenuation Fields With Application to 2D-3D Image Registration," IEEE transactions on medical imaging 24.11 (2005): 1441-1454.
Russakoff et al., "Intensity-Based 2D-3D Spine Image Registration Incorporating One Fiducial Marker," International Conference on Medical Image Computing and Computer-Assisted Intervention. Springer, Berlin, Heidelberg, 2003.
Sakai et al., "Simultaneous Registration With CT-Fluoro Matching for Spinal Navigation Surgery," Nagoya J. Med. Sci 68 (2006): 45-52.
Table of Contents from 2001 IEEE Computer Science Conference on Computer Vision and Pattern Recognition—dated Dec. 8-14, 2001.
Toews et al., "A Feature-based Approach to Big Data Analysis of Medical Images," International Conference on Information Processing in Medical Imaging. Springer, Cham, 2015.
Tomazevic and Pernus. "Robust gradient-based 3-D/2-D registration of CT and MR to X-ray images." IEEE Transactions on Medical Imaging 27.12 (2008): 1704-1714.
Tomazevic, "3-D/2-D registration of CT and MR to X-ray images," IEEE transactions on medical imaging 22.11 (2003): 1407-1416.—abstract.
Tomazevic, "3D/2D Registration of Medical Images," Utrecht University, 2008.
U.S. Appl. No. 62/307,514, filed Mar. 13, 2016.
U.S. Appl. No. 62/334,463, filed May 11, 2016.
U.S. Appl. No. 62/362,607, filed Jul. 15, 2016.
U.S. Appl. No. 62/398,085, filed Sep. 22, 2016.
U.S. Appl. No. 62/439,495, filed Dec. 28, 2016.
U.S. Appl. No. 62/463,747, filed Feb. 27, 2017.
Uneri et al., "Deformable 3D-2D Registration of Known Components for Image Guidance in Spine Surgery," International Conference on Medical Image Computing and Computer-Assisted Intervention. Springer, Cham, 2016.
Uneri et al., "Image-Based Known-Component Registration for Surgical Guidance," presented at 2017 Image Guided Therapy (IGT) Workshop, Mar. 15, 2017.
Whitmarsh et al., "3D reconstruction of the lumbar vertebrae from anteroposterior and lateral dual-energy X-ray absorptiometry," Medical Image Analysis, 2013, 17(4), 475-487.
Written Opinion of the International Searching Authority dated Feb. 21, 2017, which issued during the prosecution of Applicant's PCT/US2016/066672.
Wu et al., "Scalable High Performance Image Registration Framework by Unsupervised Deep Feature Representations Learning," IEEE Transactions on Biomedical Engineering 63.7 (2016): 1505-1516.
Yaniv, "Registration for Orthopaedic Interventions," Computational Radiology for Orthopaedic Interventions. Springer, Cham, 2016. 41-70.
Zöllei et al., 2D-3D Rigid Registration of X-Ray Fluoroscopy and CT Images Using Mutual Information and Sparsely Sampled Histogram Estimators (2001).
Zöllei et al., "2D-3D Rigid Registration of X-Ray Fluoroscopy and CT Images Using Mutual Information and Sparsely Sampled Histogram Estimators," Computer Vision and Pattern Recognition, 2001. CVPR 2001. Proceedings of the 2001 IEEE Computer Society Conference on. vol. 2. IEEE, 2001.—abstract.
PCT International Search Report and Written Opinion in International Appln. PCT/IL2019/051272, dated Mar. 8, 2020, 27 pages.

* cited by examiner

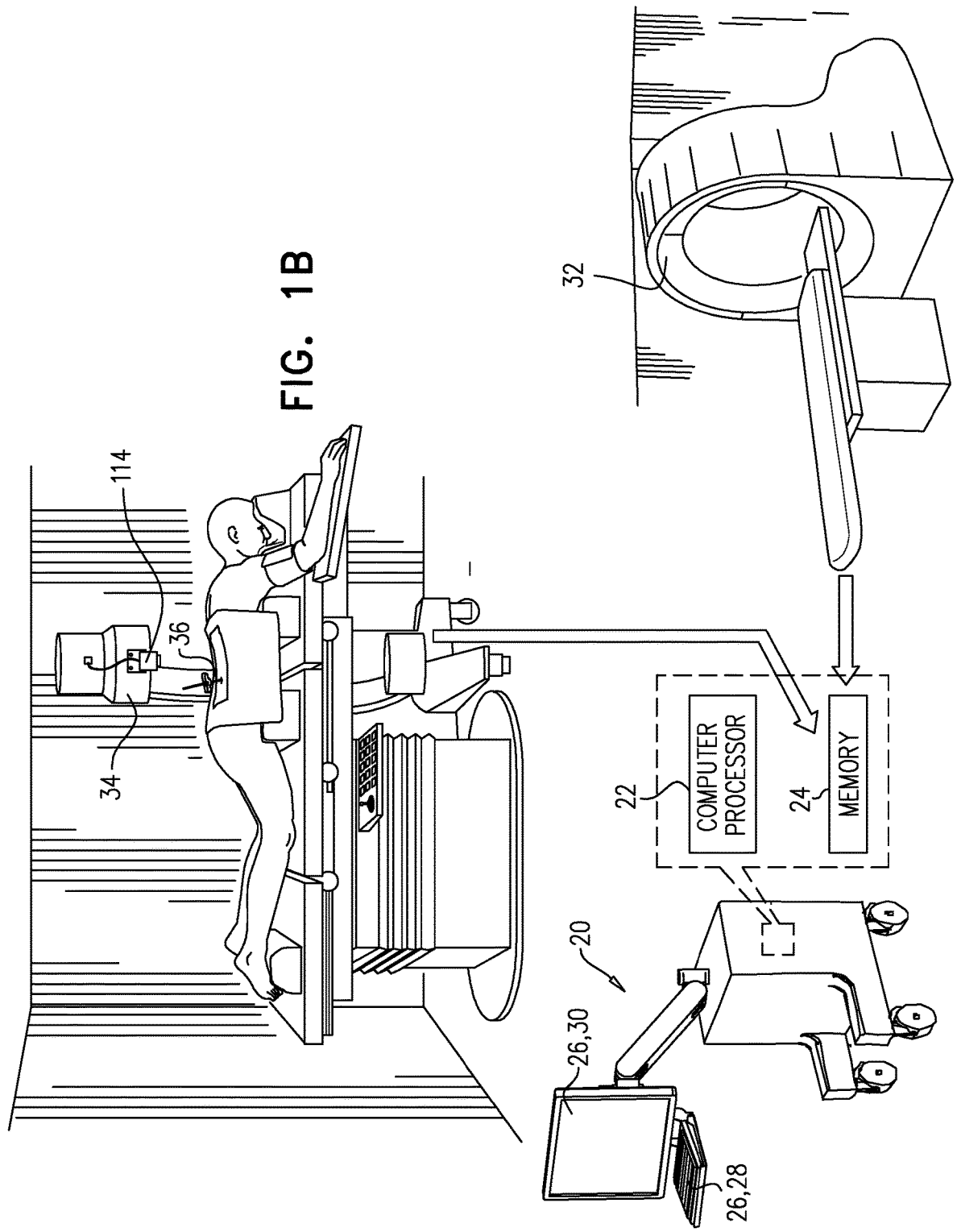

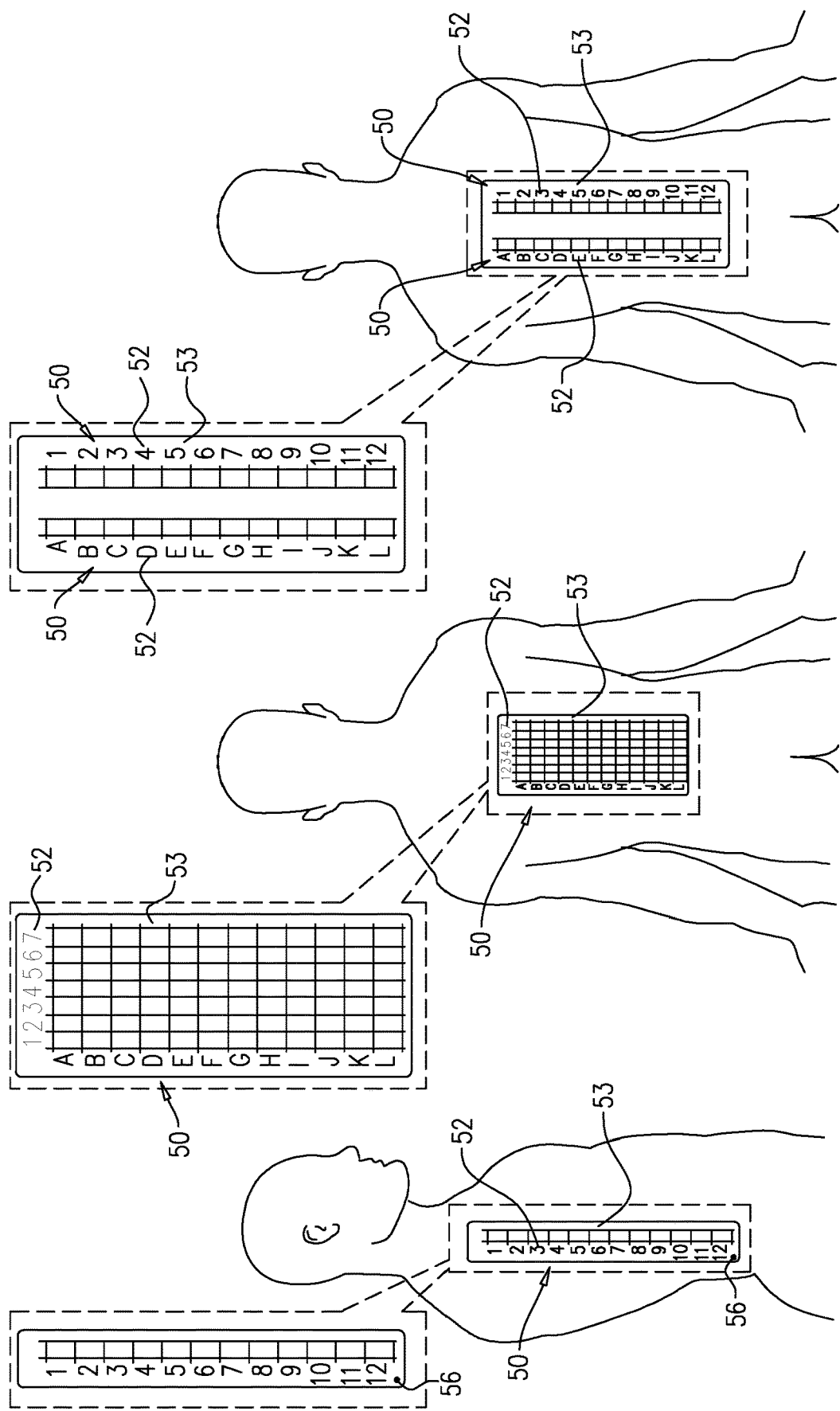

FIG. 8A
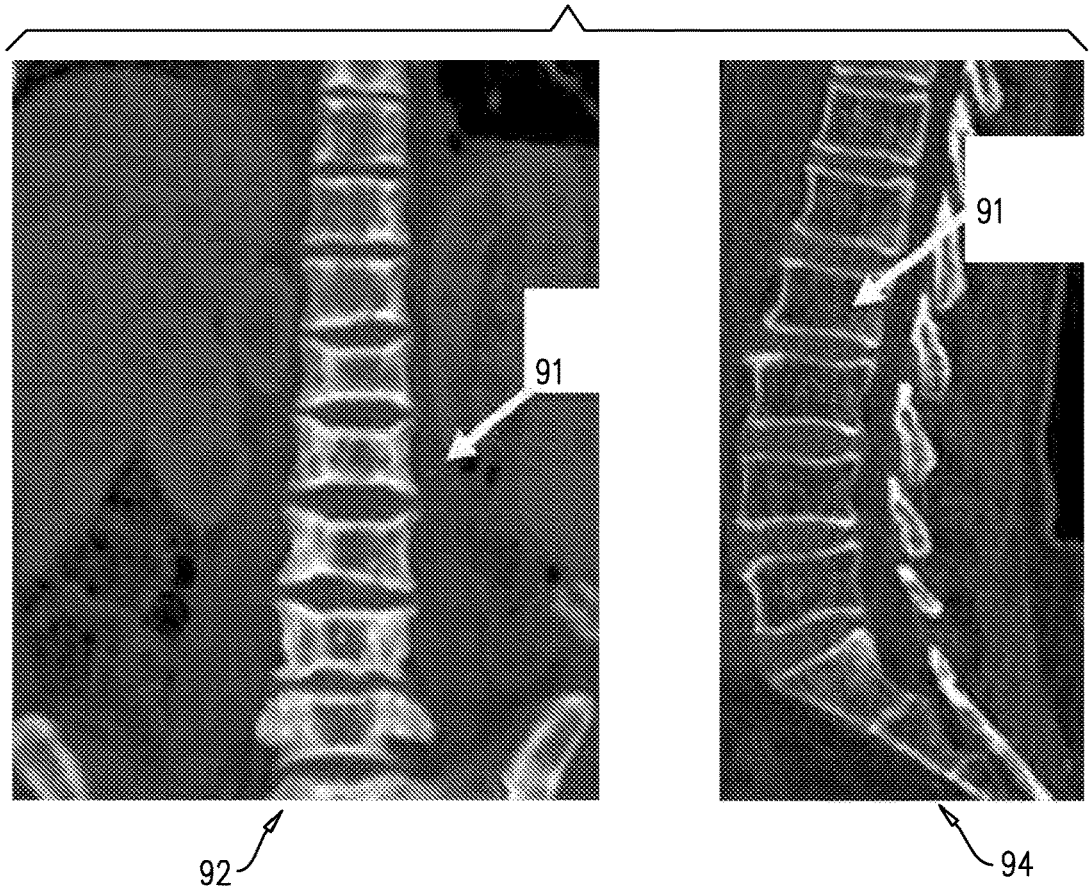
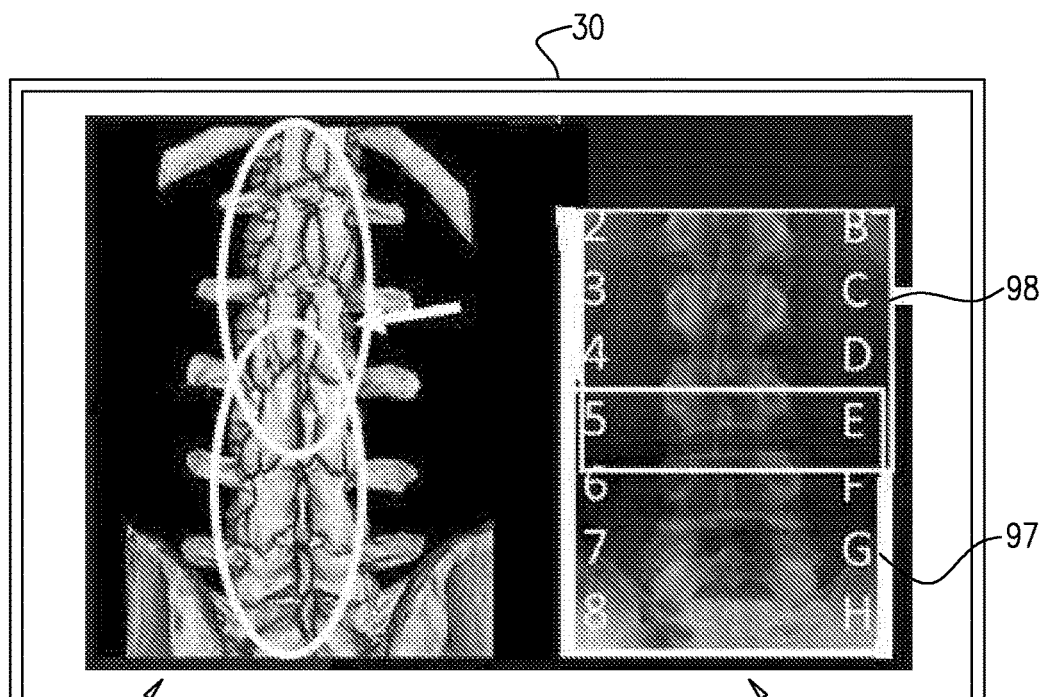
FIG. 8B

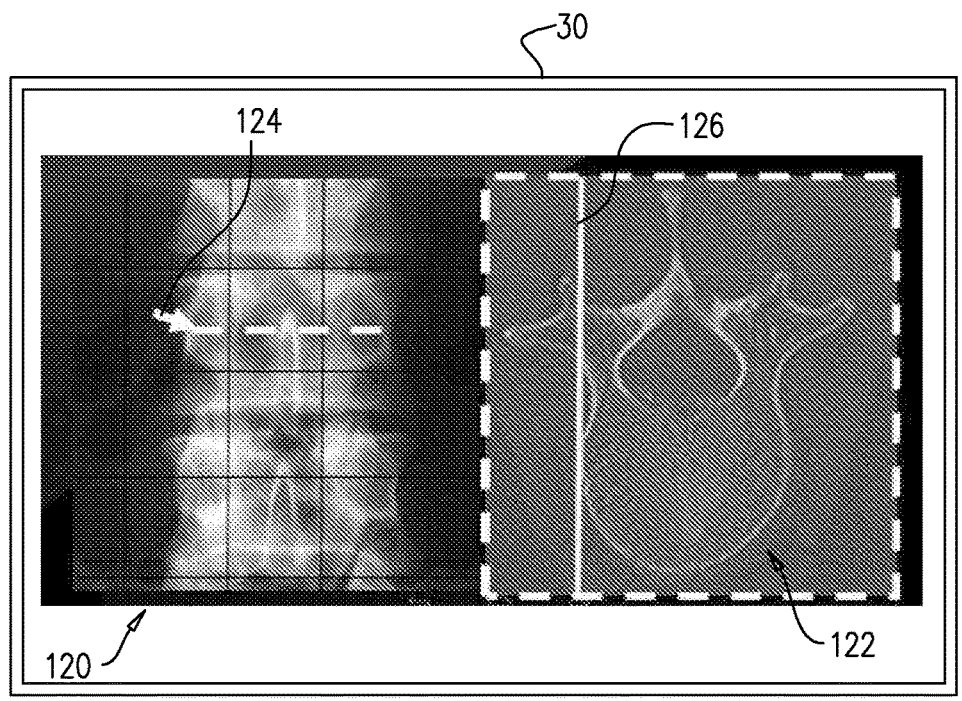
FIG. 10
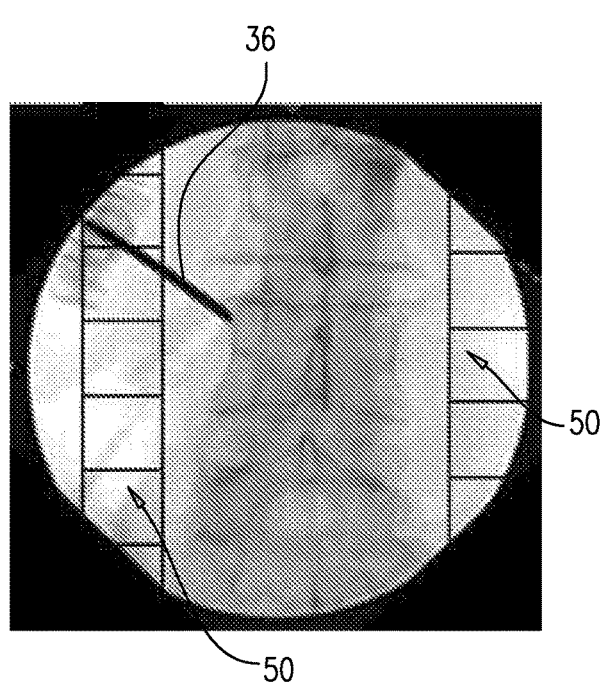 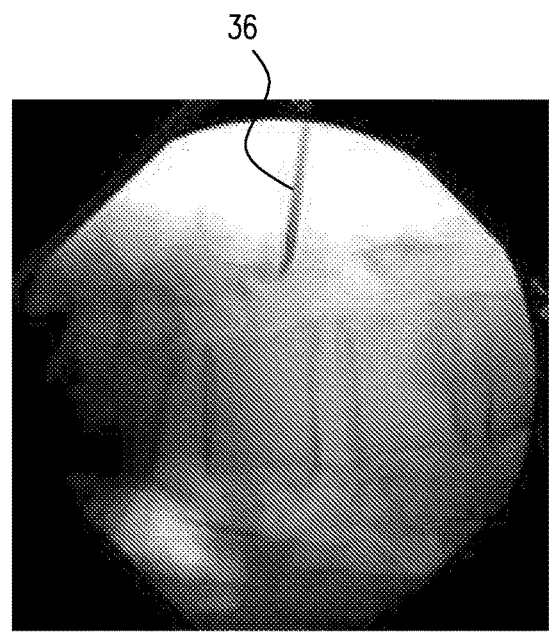
FIG. 11A	FIG. 11B

FIG. 13A
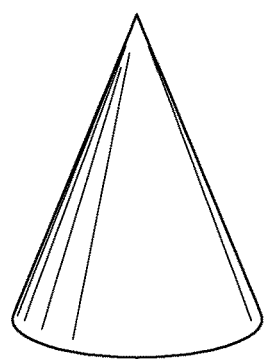
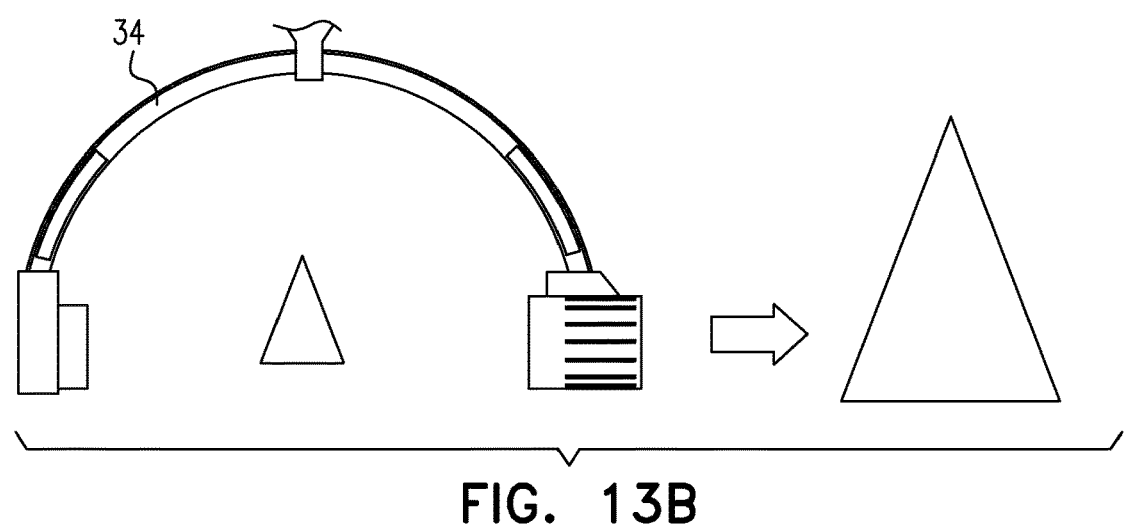
FIG. 13B
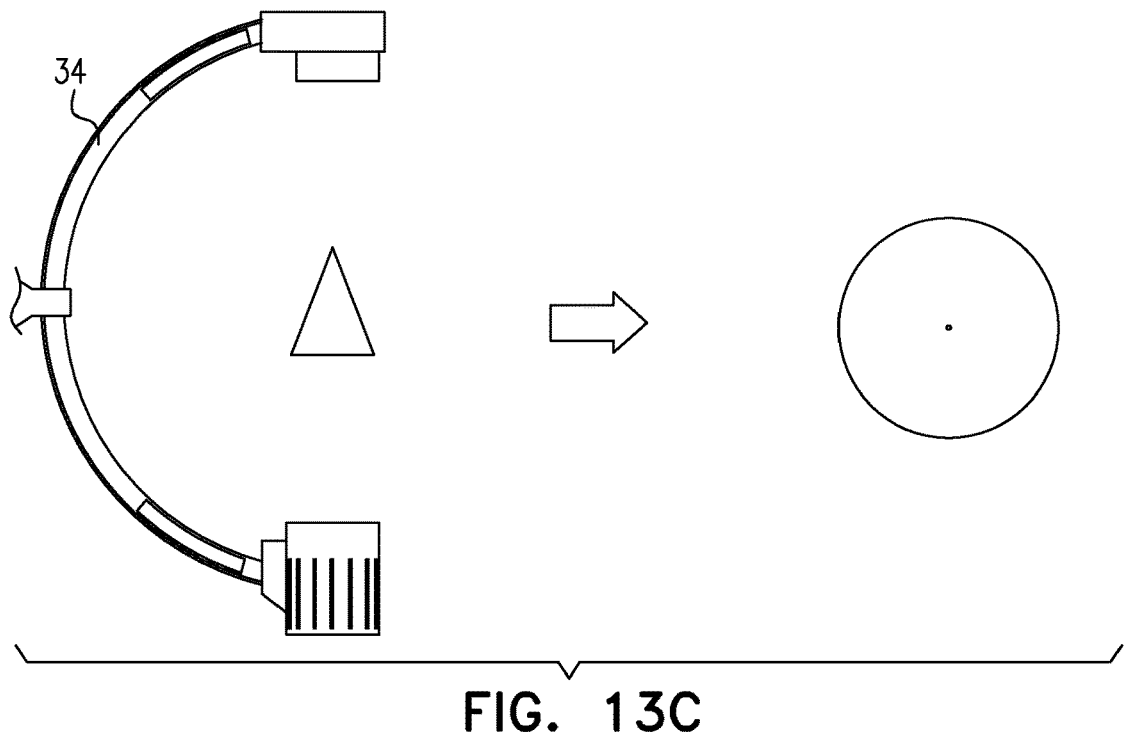
FIG. 13C 210  200

APPARATUS AND METHODS FOR USE WITH SKELETAL PROCEDURES

CROSS-REFERENCE TO RELATED APPLICATIONS

The present application is the US national stage application of PCT IL/2017/050314 filed Mar. 13, 2017, which published as PCT Publication WO 2017/158592 to Tolkowsky, and which claims priority from:

U.S. Provisional Patent Application No. 62/307,514 to Tolkowsky, filed Mar. 13, 2016, entitled "Freehand Assistant for Spinal Surgery;"

U.S. Provisional Patent Application No. 62/334,463 to Tolkowsky, filed May 11, 2016, entitled "Freehand Assistant for Spinal Surgery;"

U.S. Provisional Patent Application No. 62/362,607 to Tolkowsky, filed Jul. 15, 2016, entitled "Freehand Assistant for Spinal Surgery;"

U.S. Provisional Patent Application No. 62/398,085 to Tolkowsky, filed Sep. 22, 2016, entitled "Freehand Assistant for Spinal Surgery;"

U.S. Provisional Patent Application No. 62/439,495 to Tolkowsky, filed Dec. 28, 2016, entitled "Freehand Assistant for Spinal Surgery;" and U.S. Provisional Patent Application No. 62/463,747 to Tolkowsky, filed Feb. 27, 2017, entitled "Freehand Assistant for Spinal Surgery."

The above-referenced applications are incorporated herein by reference.

FIELD OF EMBODIMENTS OF THE INVENTION

Some applications of the present invention generally relate to medical apparatus and methods. Specifically, some applications of the present invention relate to apparatus and methods for use in procedures that are performed on skeletal anatomy.

BACKGROUND

Approximately 5 million spine surgeries are performed annually worldwide. Traditional, manual surgery is known as freehand surgery. Typically, for such procedures, a 3D scan (e.g., a CT and/or MRI) scan is performed prior to surgery. A CT scan is typically performed for bony tissue (e.g., vertebra), and an MRI scan is typically performed for soft tissue (e.g., discs).

Reference is made to FIG. 1A, which is a schematic illustration of a typical set up of an orthopedic operating room, for procedures that are performed in a freehand manner. Typically, in freehand procedures, although the CT and/or MRI scan is examined by the surgeon when preparing for surgery, no use is made of the CT and/or MRI images during surgery. Rather, the surgery is typically performed under 2D x-ray image guidance (also referred to as fluoroscopic guidance), the 2D x-rays typically being acquired using an x-ray C-arm. FIG. 1A shows a surgeon 10 performing a procedure using intraprocedural x-ray images that are acquired by a C-arm 34, and displayed on a display 12. Freehand surgery in which there is significant use of x-rays is known as fluoroscopy-guided surgery. X-ray C-arms are ubiquitous, familiar to surgeons, useful for acquiring real-time images, tool-neutral (i.e., there is no requirement to use orthopedic tools that are adapted specifically for imaging by the x-ray C-arm), and relatively inexpensive. A growing proportion of spinal surgeries are performed using a minimally-invasive surgery (also known as "MIS," or in the case of spine surgery, minimally-invasive spine surgery, which is also known as "MISS"), or "mini-open" surgery. In contrast to open surgery, in which an incision is made along the applicable segment of the spine upon which surgery is performed, in minimally-invasive surgery, very small incisions are made at the insertion point of tools. In "mini-open" surgery, incisions are made that are smaller than in open surgery and larger than in minimally-invasive surgery. Typically, the less invasive the type of surgery that is performed, the greater the use of x-ray imaging for assisting the procedure. There is evidence that less invasive procedures that are performed under fluoroscopic guidance are more accurate than open procedures. However, the use of real-time fluoroscopic guidance typically exposes the patient, as well as the surgeon and the support staff to a relatively large amount of harmful radiation.

A minority of procedures are performed using Computer Aided Surgery (CAS) systems that provide navigation and/or robotics. Such systems typically make use of CT and/or MRI images that are generated before the patient is in the operating room, or when the patient is within the operating room, but typically before an intervention has commenced. The CT and/or MRI images are registered to the patient's body, and, during surgery, tools are navigated upon the images, the tools being moved manually, robotically or both.

Typically, in CAS procedures, a uniquely-identifiable location sensor is attached to each tool that needs to be tracked by the CAS system. Each tool is identified and calibrated at the beginning of the procedure. In addition, a uniquely-identifiable reference sensor is rigidly attached to the organ. In the case of spinal surgery, the reference sensor is typically drilled into the sacrum or spine, and, if surgery is performed along a number of vertebrae, the reference sensor is sometimes moved and drilled into a different portion of the spine, mid-surgery, in order to always be close to the surgical site. The images to be navigated upon (e.g., CT, MRI), which are acquired before the patient is in the operating room, or when the patient is within the operating room, but before an intervention has commenced, are registered to the patient's body or a portion thereof. In order to register the images to the patient's body, the current location of the patient's body is brought into the same reference frame of coordinates as the images using the reference sensor. The location sensors on the tools and the reference sensor on the patient's body are then tracked in order to determine the locations of the tools relative to the patient's body, and a symbolic representation of the tool is displayed upon the images that are navigated upon. Typically, the tool is tracked in 5-6 degrees of freedom.

There are various techniques that are utilized for the tracking of tools, and corresponding location sensors are used for each technique. One technique is infrared ("IR") tracking, whereby an array of cameras track active IR lights on the tools and the patient's body, or an array of beams and cameras tracks passive IR reflectors on the tools and the patient's body. In both categories of IR tracking, lines of sight must be maintained at all times between the tracker and the tools. For example, if the line of sight is blocked by the surgeon's hands, this can interfere with the tracking. Another technique is electromagnetic or magnetic tracking, whereby a field generator tracks receivers, typically coils, on the tools and the patient's body. For those latter techniques, environmental interferences from other equipment much be avoided. In each of the techniques, the location sensors of the navigation system are tracked using tracking components that would not be present in the operating room in the absence of the navigation system (i.e., the location sensors do not simply rely upon imaging by imaging devices that are typically used in an orthopedic operating room in the absence of the navigation system).

A further technique that can be used with a robotically-driven tool is to start with the tool at a known starting point relative to the patient's body, and to then record motion of the tool from the starting point. Alternatively, such tools can be tracked using the above-described techniques.

Given the nature of CAS procedures, the equipment required for such procedures is typically more expensive than that of non-CAS procedures (non-CAS procedures including open procedures, mini-open procedures, or minimally-invasive procedures that are not computer aided with respect to the guidance of tools). Such procedures typically limit tool selection to those fitted with location sensors as described above, and typically require such tools to be individually identified and calibrated at the beginning of each surgery.

SUMMARY OF EMBODIMENTS

In accordance with some applications of the present invention, the following steps are typically performed during procedures that are performed on skeletal anatomy, using a system that includes a computer processor. Such procedures may include joint (e.g., shoulder, knee, hip, and/or ankle) replacement, joint repair, fracture repair (e.g., femur, tibia, and/or fibula), a procedure that is performed on a rib (e.g., rib removal, or rib resection), and/or other interventions in which 3D image data are acquired prior to the intervention and 2D images are acquired during the intervention. For some applications, the steps are performed during a procedure that is performed on one or more vertebrae of a subject's spine.

Typically, in a first step, targeted vertebra(e) are marked by an operator with respect to 3D image data (e.g., a 3D image, a 2D cross-section derived from 3D image data, and/or a 2D projection image derived from 3D image data) of the subject's spine. For some applications, in a second step, sets of markers are placed on the subject, underneath the subject, on the surgical table, or above the surgical table in a vicinity of the subject. Typically, in a third step, vertebrae of the spine are identified in order to verify that the procedure is being performed with respect to the correct vertebra (a step which is known as "level verification"), using radiographic images of the spine and the markers to facilitate the identification. For some applications, in a fourth step, an incision site (in the case of minimally-invasive surgery), or a tool entry point into a vertebra (in the case of open surgery) is determined. In a fifth step, the first tool in the sequence of tools (which is typically a needle, e.g., a Jamshidi™ needle) is typically inserted into the subject (e.g., in the subject's back) via the incision site or the tool entry point, and is slightly fixated in the vertebra. In a sixth step, two or more 2D radiographic images are typically acquired from respective views that typically differ by at least 10 degrees (and further typically by 30 degrees or more), and one of which is typically from the direction of insertion of the tool. Typically, generally-AP and generally-lateral images are acquired. Alternatively or additionally, images from different views are acquired. Typically, in a seventh step, the computer processor registers the 3D image data to the 2D images.

Typically, 3D image data and 2D images of individual vertebrae are registered to each other. Further typically, the 3D image data and 2D images are registered to each other by generating a plurality of 2D projections from the 3D image data, and identifying respective first and second 2D projections that match each of the 2D x-ray images of the vertebra, as described in further detail hereinbelow. Typically, first and second 2D x-ray images of the vertebra are acquired using an x-ray imaging device that is unregistered with respect to the subject's body, by (a) acquiring a first 2D x-ray image of the vertebra (and at least a portion of the tool) from a first view, while the x-ray imaging device is disposed at a first pose with respect to the subject's body, (b) moving the x-ray imaging device to a second pose with respect to the subject's body, and (c) while the x-ray imaging device is at the second pose, acquiring a second 2D x-ray image of at least the portion of the tool and the vertebra from a second view. For some applications, more than two 2D x-rays are acquired from respective x-ray image views, and the 3D image data and 2D x-ray images are typically all registered to each other by identifying a corresponding number of 2D projections of the 3D image data that match respective 2D x-ray images.

For some applications, the computer processor acquires a 2D x-ray image of a tool inside the vertebra from only a single x-ray image view, and the 2D x-ray image is registered to the 3D image data by generating a plurality of 2D projections from the 3D image data, and identifying a 2D projection that matches the 2D x-ray image of the vertebra. In response to registering the 2D x-ray image to the 3D image data, the computer processor drives a display to display a cross-section derived from the 3D image data at a current location of a tip of the tool, as identified from the 2D x-ray image, and optionally to show a vertical line on the cross-sectional image indicating a line within the cross-sectional image somewhere along which the tip of the tool is currently disposed.

As described hereinabove, typically two or more 2D x-rays are acquired from respective x-ray image views, and the 3D image data and 2D images are typically registered to each other by identifying a corresponding number of 2D projections of the 3D image data that match respective 2D x-ray images. Subsequent to the registration of the 3D image data to the 2D x-ray images, additional features of the system are applied by the computer processor. For example, the computer processor may drive the display to display the anticipated (i.e., extrapolated) path of the tool with reference to a target location and/or with reference to a desired insertion vector. For some applications, the computer processor simulates tool progress within a secondary 2D imaging view, based upon observed progress of the tool in a primary 2D imaging view. Alternatively or additionally, the computer processor overlays an image of the tool, a representation thereof, and/or a representation of the tool path, upon the 3D image data (e.g., a 3D image, a 2D cross-section derived from 3D image data, and/or a 2D projection image derived from 3D image data), the location of the tool or tool path having been derived from current 2D images.

As described hereinabove, for some applications, sets of markers are placed on the subject, underneath the subject, on the surgical table, or above the surgical table. Typically, the markers that are placed at respective locations with respect to the subject are identifiable in x-ray images, in optical images, and physically to the human eye. For example, respective radiopaque alphanumeric characters may be placed at respective locations. For some applications, markers placed at respective locations are identifiable based upon other features, e.g., based upon the dispositions of the markers relative to other markers. Using a radiographic imaging device, a plurality of radiographic images of the set of radiopaque markers are acquired, respective images being of respective locations along at least a portion of the subject's spine and each of the images including at least some of the radiopaque markers. Using the computer processor, locations of the radiopaque markers within the radiographic images are identified, by means of image processing. At least some of the radiographic images are combined with respect to one another based upon the identified locations of the radiopaque markers within the radiographic images. Typically, such combination of images is similar to stitching of images. However, the images are typically not precisely stitched such as to stitch portions of the subject's anatomy in adjacent images to one another. Rather, the images are combined with sufficient accuracy to be able to determine a location of the given vertebra within the combined radiographic images. The computer processor thus automatically determines (or facilitates manual determination of) a location of a given vertebra within the combined radiographic images. Based upon the location of the given vertebra within the combined radiographic images, a location of the given vertebra in relation to the set of radiopaque markers that is placed on the subject is determined, as described in further detail hereinbelow. The markers are typically utilized to provide additional functionalities, or in some cases to facilitate functionalities, as described in further detail hereinbelow.

There is therefore provided, in accordance with some applications of the present invention, apparatus for performing a procedure using a tool configured to be advanced into a skeletal portion within a body of a subject along a longitudinal insertion path, and for use with:

(a) a 3D imaging device configured to acquire 3D image data of the skeletal portion, (b) a 2D x-ray imaging device that is unregistered with respect to the subject's body and configured, while a portion of the tool is disposed at a first location along the longitudinal insertion path, to sequentially:

acquire a first 2D x-ray image of at least the portion of the tool and the skeletal portion from a first view, while the 2D x-ray imaging device is disposed at a first pose with respect to the subject's body, be moved to a second pose with respect to the subject's body, and while the 2D x-ray imaging device is at the second pose, acquire a second 2D x-ray image of at least the portion of the tool and the skeletal portion from a second view, and (c) an output device, the apparatus including:

at least one computer processor configured to:

receive the 3D image data of the skeletal portion from the 3D imaging device, receive the first and second 2D x-ray images of at least the portion of the tool and the skeletal portion from the 2D x-ray imaging device, register the first and second 2D x-ray images to the 3D image data, the registering including:

generating a plurality of 2D projections from the 3D image data, and identifying respective first and second 2D projections that match the first and second 2D x-ray images of the skeletal portion, identify a location of the portion of the tool with respect to the skeletal portion, within the first and second 2D x-ray images, by means of image processing, based upon the identified location of the portion of the tool within the first and second 2D x-ray images, and the registration of the first and second 2D x-ray images to the 3D image data, determine the first location of the portion of the tool with respect to the 3D image data, subsequent to moving the portion of the tool to a second location along the longitudinal insertion path with respect to the skeletal portion, receive one or more additional 2D x-ray images of at least the portion of the tool and the skeletal portion from the 2D x-ray imaging device, the one or more additional 2D x-ray images being acquired from a single image view, identify the second location of the portion of the tool within the one or more additional 2D x-ray images, by means of image processing, derive the second location of the portion of the tool with respect to the 3D image data, based upon the second location of the portion of the tool within the one or more additional 2D x-ray images, and the determined first location of the portion of the tool with respect to the 3D image data, and generate an output on the output device, at least partially in response thereto.

In some applications, the at least one computer processor is configured to receive the one or more additional 2D x-ray images of at least the portion of the tool and the skeletal portion from the 2D x-ray imaging device that are acquired from the single image view by receiving one or more additional 2D x-ray images of at least the portion of the tool and the skeletal portion from one of the first and second image views. In some applications, the at least one computer processor is configured to receive the one or more additional 2D x-ray images of at least the portion of the tool and the skeletal portion from the 2D x-ray imaging device that are acquired from the single image view by receiving one or more additional 2D x-ray images of at least the portion of the tool and the skeletal portion from a third image view that is different from the first and second image views.

There is further provided, in accordance with some applications of the present invention, apparatus for performing a procedure using a tool configured to be advanced into a skeletal portion within a body of a subject along a longitudinal insertion path, and for use with:

(a) a 2D x-ray imaging device that is unregistered with respect to the subject's body and configured, while a portion of the tool is disposed at a first location along the longitudinal insertion path, to sequentially:

acquire a first 2D x-ray image of at least the portion of the tool and the skeletal portion from a first view, while the 2D x-ray imaging device is disposed at a first pose with respect to the subject's body, be moved to a second pose with respect to the subject's body, and while the 2D x-ray imaging device is at the second pose, acquire a second 2D x-ray image of at least the portion of the tool and the skeletal portion from a second view, and (b) an output device, the apparatus including:

at least one computer processor configured:

to receive the first and second 2D x-ray images of at least the portion of the tool and the skeletal portion from the 2D x-ray imaging device, to identify the portion of the tool in the first and second 2D x-ray images, by means of image processing, to determine a relationship between the first and second 2D x-ray images, subsequent to the tool being advanced along the longitudinal insertion path with respect to the skeletal portion, such that the portion of the tool is disposed at a second location along the longitudinal insertion path, to receive one or more additional 2D x-ray images of at least the portion of the tool and the skeletal portion from the 2D x-ray imaging device, the one or more additional 2D x-ray images being acquired from a single image view, to identify the second location of the portion of the tool within the one or more additional 2D x-ray images, by means of image processing, to derive the second location of the portion of the tool with respect to at least one of the first and second 2D x-ray images, based upon the second location of the portion of the tool that was identified within the one or more additional 2D x-ray images, and the determined relationship between the first and second 2D x-ray images, and to generate an output on the output device, at least partially in response thereto.

In some applications, the at least one computer processor is configured to determine the relationship between the first and second 2D x-ray images by registering the first and second 2D x-ray images to 3D image data of the skeletal portion. In some applications, the apparatus is for use with a three-dimensional radiopaque jig, and the at least one computer processor is configured to determine the relationship between the first and second 2D x-ray images using the three-dimensional radiopaque jig that is visible in the first and second 2D x-ray images. In some applications, the tool includes two or more radiopaque features that are visible in the first and second 2D x-ray images, and the at least one computer processor is configured to determine the relationship between the first and second 2D x-ray images using the two or more radiopaque portions of the tool that are visible in the first and second 2D x-ray images. In some applications, the at least one computer processor is configured to receive the one or more additional 2D x-ray images of at least the portion of the tool and the skeletal portion from the 2D x-ray imaging device by receiving one or more additional 2D x-ray images of at least the portion of the tool and the skeletal portion from one of the first and second image views. In some applications, the at least one computer processor is configured to receive the one or more additional 2D x-ray images of at least the portion of the tool and the skeletal portion from the 2D x-ray imaging device by receiving one or more additional 2D x-ray images of at least the portion of the tool and the skeletal portion from a third image view that is different from the first and second image views.

There is further provided, in accordance with some applications of the present invention, apparatus for performing a procedure with respect to a given vertebra of a spine of a subject, and for use with a radiographic imaging device, the apparatus including:

a set of radiopaque markers configured to be placed in a vicinity of the subject, such that markers that are placed at respective locations with respect to the subject are identifiable; and at least one computer processor configured:
to receive, from the radiographic imaging device, a plurality of radiographic images of the set of radiopaque markers, respective images being of respective locations along at least a portion of the subject's spine and each of the images including at least some of the radiopaque markers, to identify locations of the radiopaque markers within the radiographic images, by means of image processing, to combine at least some of the radiographic images with respect to one another based upon the identified locations of the radiopaque markers within the radiographic images, to automatically determine a location of the given vertebra within the combined radiographic images, by means of image processing, and to generate an output in response thereto.

In some applications, the apparatus is for use with a display, and the at least one computer processor is configured to generate the output by driving the display to display the combined radiographic images with an indication of the given vertebra displayed with respect to the combined radiographic images. In some applications, the apparatus is for use with a display, and the at least one computer processor is configured to generate the output by driving the display to display the combined radiographic images with an indication of the given vertebra displayed with respect to the combined radiographic images, and driving the display to display an indication of the given vertebra with respect to 3D image data of at least a portion of the subject's spine.

In some applications, the at least one computer processor is configured to automatically determine the location of the given vertebra within the combined radiographic images by means of image processing, by: identifying an identifiable feature within the combined radiographic image; identifying individual vertebra within the combined radiographic image; and counting vertebra from the identifiable feature. In some applications, the at least one computer processor is configured to identify the identifiable feature within the combined radiographic image by identifying a sacrum of the subject within the combined radiographic image.

There is further provided, in accordance with some applications of the present invention, apparatus for performing a procedure with respect to a given rib of a ribcage of a subject, and for use with a radiographic imaging device, the apparatus including:

a set of radiopaque markers configured to be placed in a vicinity of the subject, such that markers that are placed at respective locations with respect to the subject are identifiable; and at least one computer processor configured:
to receive, from the radiographic imaging device, a plurality of radiographic images of the set of radiopaque markers, respective images being of respective locations along at least a portion of the subject's ribcage and each of the images including at least some of the radiopaque markers, to identify locations of the radiopaque markers within the radiographic images, by means of image processing, to combine at least some of the radiographic images with respect to one another based upon the identified locations of the radiopaque markers within the radiographic images to automatically determine a location of the given rib within the combined radiographic images, by means of image processing, and to generate an output in response thereto.

There is further provided, in accordance with some applications of the present invention, apparatus for performing a procedure on a spine of a body of a subject, the apparatus including:

a first set of radiopaque markers;
a second set of radiopaque markers; and one or more surfaces, the first and second sets of radiopaque markers being coupled to one another via the one or more surfaces, the one or more surfaces being configured:

to position the first and second sets of markers on respective sides of the subject's spine at predefined positions with respect to each other, by the one or more surfaces being placed over a portion of the subject's spine upon which the procedure is to be performed; and subsequent to positioning the first and second set of markers on the respective sides of the subject's spine, to be removable from the subject's body, such as to facilitate performance of the procedure upon the portion of the subject's spine over which the one or more surfaces were placed, while leaving the first and second sets of markers on the respective sides of the subject's spine at the predefined position with respect to each other.

In some applications, at least some of the markers of each of the first and second sets of markers are rigid and have known dimensions. In some applications, each of the first and second sets of markers includes a set of radiopaque characters, the sets being different from each other. In some applications, the apparatus further includes a third set of a radiopaque markers that is coupled to the first and second set of markers via the one or more surfaces such that the third set of markers is configured to be positioned along a center of the subject's spine, when the first and second sets of markers are positioned on respective sides of the subject's spine at the predefined positions with respect to each other, by the one or more surfaces being placed over the portion of the subject's spine upon which the procedure is to be performed.

There is further provided, in accordance with some applications of the present invention, apparatus for use with a radiographic imaging device that is configured to acquire radiographic images of a spine of a body of a subject, the apparatus including:

a flexible material configured to be placed upon the subject's body along at least a portion of the subject's spine, and to generally conform to contours of the subject's body; and a set of radiopaque markers disposed upon the flexible material, at least some of the radiopaque markers being rigid and having respective known dimensions, the rigid radiopaque markers being disposed upon the flexible material, such that rigidity of the rigid markers does not prevent the flexible material from generally conforming to the contours of the subject's body; and at least one computer processor configured to:

identify, by means of image processing, at least one of the rigid radiopaque markers within a radiographic image of the spine acquired by the radiographic imaging device, and based upon the identified rigid radiopaque markers, determine dimensions of features within the radiographic image, by means of image processing.

There is further provided, in accordance with some applications of the present invention, a method for performing a procedure on a spine of a body of a subject, the method including:

providing:
a first set of radiopaque markers, and
a second set of radiopaque markers, and positioning the first and sets of markers with respect to the subject's spine, such that the first set of the markers appear in radiographic images of the subject's spine that are acquired from a first image view, and such that the second set of the markers appear in radiographic images of the subject's spine that are acquired from a second image view;

acquiring radiographic images of the subject's spine from the first and second image views; and associating a given vertebra that appears in the radiographic images of the spine from the first image view, with the given vertebra of the spine in the radiographic images of the spine from the second image view, by identifying markers that have a known association with one another in the radiographic images acquired from the first and second image views.

In some applications, associating the given vertebra that appears in the radiographic images of the spine from the first image view, with the given vertebra of the spine in the radiographic images of the spine from the second image view includes, using at least one computer processor, associating the given vertebra that appears in the radiographic images of the spine from the first image view, with the given vertebra of the spine in the radiographic images of the spine from the second image view, by identifying markers that have a known association with one another in the radiographic images acquired from the first and second image views. In some applications, associating the given vertebra that appears in the radiographic images of the spine from the first image view, with the given vertebra of the spine in the radiographic images of the spine from the second image view includes, manually, associating the given vertebra that appears in the radiographic images of the spine from the first image view, with the given vertebra of the spine in the radiographic images of the spine from the second image view, by identifying markers that have a known association with one another in the radiographic images acquired from the first and second image views There is further provided, in accordance with some applications of the present invention, apparatus for performing a procedure on a spine of a body of a subject, the apparatus including:

a first set of radiopaque markers configured to be placed with respect to the subject's spine such that the first set of radiopaque markers appear in radiographic images of the subject's spine that are acquired from a first image view; and a second set of radiopaque markers, the first and second sets of markers being coupled to one another such that when first set of radiopaque markers are placed with respect to the subject's spine such that the first set of radiopaque markers appear in radiographic images of the subject's spine that are acquired from the first image view, the second set of the markers appear in radiographic images of the subject's spine that are acquired from a second image view, the first and second sets of markers thereby facilitating associating a given vertebra that appears in the radiographic images of the spine from the first image view, with the given vertebra of the spine in the radiographic images of the spine from the second image view, by facilitating identification of markers that have a known association with one another in the radiographic images acquired from the first and second image views.

In some applications, the apparatus further includes at least one computer processor that is configured to associate the given vertebra that appears in the radiographic images of the spine from the first image view with the given vertebra of the spine in the radiographic images of the spine from the second image view, by identifying markers that have the known association with one another in the radiographic images acquired from the first and second image views.

There is further provided, in accordance with some applications of the present invention, apparatus for performing a procedure with respect to a skeletal portion within a body of a subject, using a 2D radiographic imaging device, an optical camera, and one or more displays, the apparatus including:

a set of radiopaque markers configured to be placed in a vicinity of the subject; and at least one computer processor configured:
to receive a radiographic image of the skeletal portion from the 2D radiographic imaging device,
to receive an optical image of the subject's body from the optical camera;
to identify the radiopaque markers in the radiographic image and in the optical image, by means of image processing,
based upon the identification of the radiopaque markers in the radiographic image and in the optical image, to bidirectionally map the radiographic image and the optical image with respect to one another,
to display the radiographic image and the optical image separately from one another, upon the one or more displays,
to receive an input indicating a location in a first one of the radiographic and the optical images, and
in response thereto, to generate an output indicating the location in the other one of the radiographic and the optical images.

In some applications, the at least one computer processor is configured to receive the input indicating the location in the first one of the radiographic and the optical images by identifying, within the optical image of the subject's body, an object placed at a proposed entry point into the skeletal portion, and the at least one computer processor is configured to generate the output by generating an output indicating the proposed entry point into the skeletal portion with respect to the radiographic image. In some applications, the at least one computer processor is configured to receive the input indicating the location in the first one of the radiographic and the optical images by identifying, within the optical image of the subject's body, an object placed at a proposed incision site, and the at least one computer processor is configured to generate the output by generating an output indicating the proposed incision site in the radiographic image.

In some applications, the at least one computer processor is configured to receive the input indicating the location in the first one of the radiographic and the optical images by receiving an input indicating a location in the optical image, the at least one computer processor being further configured, in response to receiving the input, to drive the one or more displays to display a cross-section of the skeletal portion corresponding to the indicated location. In some applications, the at least one computer processor is further configured, in response to receiving the input, to drive the one or more displays to display a line upon the cross-section of the skeletal portion, indicating that the indicated location is somewhere along the line.

There is further provided, in accordance with some applications of the present invention, apparatus for performing a procedure using a tool configured to be advanced into a skeletal portion within a body of a subject along a longitudinal insertion path, and for use with:

(a) a 3D imaging device configured to acquire 3D image data of the skeletal portion, (b) a 2D x-ray imaging device that is unregistered with respect to the subject's body and configured, while a portion of the tool is disposed at a location along the longitudinal insertion path, to sequentially:
acquire a first 2D x-ray image of at least the portion of the tool and the skeletal portion from a first view, while the 2D x-ray imaging device is disposed at a first pose with respect to the subject's body,
be moved to a second pose with respect to the subject's body, and
while the 2D x-ray imaging device is at the second pose, acquire a second 2D x-ray image of at least the portion of the tool and the skeletal portion from a second view, and (c) an output device, the apparatus including:
at least one computer processor configured to:
receive the 3D image data of the skeletal portion from the 3D imaging device,
receive the first and second 2D x-ray images of at least the portion of the tool and the skeletal portion from the 2D x-ray imaging device,
register the first and second 2D x-ray images to the 3D image data, the registering including:
generating a plurality of 2D projections from the 3D image data, and
identifying respective first and second 2D projections that match the first and second 2D x-ray images,
identify, the location of the portion of the tool with respect to the skeletal portion, within the first and second x-ray images, by means of image processing, based upon the identified location of the portion of the tool within the first and second x-ray images, and the registration of the first and second 2D x-ray images to the 3D image data, derive a relationship between the location of the portion of the tool with respect to the 3D image data and a given location within the 3D image data, and
generate an output, on the output device, that is indicative of the relationship between the location of the portion of the tool with respect to the 3D image data and the given location within the 3D image data.

In some applications, the at least one computer processor is configured to generate the output that is indicative of the relationship between the location of the portion of the tool with respect to the 3D image data and the given location within the 3D image data by generating the output upon a 2D cross-section of the skeletal portion that is derived from the 3D image data. In some applications, the at least one computer processor is configured to generate the output that is indicative of the relationship between the location of the portion of the tool with respect to the 3D image data and the given location within the 3D image data by generating the output upon a 2D projection of the skeletal portion that is derived from the 3D image data. In some applications, the at least one computer processor is configured to generate the output that is indicative of the relationship between the location of the portion of the tool with respect to the 3D image data and the given location within the 3D image data by generating the output upon a 3D image of the skeletal portion that is derived from the 3D image data.

In some applications, the at least one computer processor is configured to derive the relationship between the location of the portion of the tool with respect to the 3D image data and the given location within the 3D image data by deriving an anticipated longitudinal insertion path of the tool with respect to the given location within the 3D image data. In some applications, the at least one computer processor is configured to derive the relationship between the location of the portion of the tool with respect to the 3D image data and the given location within the 3D image data by deriving a relationship between the first location of the portion of the tool with respect to the 3D image data and a predesignated target location within the 3D image data. In some applications, the at least one computer processor is configured to derive the relationship between the location of the portion of the tool with respect to the 3D image data and the given location within the 3D image data by deriving a relationship between the first location of the portion of the tool with respect to the 3D image data with respect to respective volumes within the 3D image data, the respective volumes designating respective levels of acceptability of protrusion of the tool with respect to the respective volumes.

There is further provided, in accordance with some applications of the present invention, apparatus for performing a procedure using a tool configured to be advanced into a skeletal portion within a body of a subject along a longitudinal insertion path, and for use with:

(a) a 3D imaging device configured to acquire 3D image data of the skeletal portion, (b) a 2D x-ray imaging device that is unregistered with respect to the subject's body and configured to sequentially:
  acquire a first 2D x-ray image of at least a portion of the tool and the skeletal portion from a first view, while the 2D x-ray imaging device is disposed at a first pose with respect to the subject's body,
  be moved to a second pose with respect to the subject's body, and
  while the 2D x-ray imaging device is at the second pose, acquire a second 2D x-ray image of at least the portion of the tool and the skeletal portion from a second view, and (c) an output device,
the apparatus including:
at least one computer processor configured to:
receive the 3D image data of the skeletal portion from the 3D imaging device,
receive a designation of a location within the skeletal portion, with respect to the 3D image data,
receive the first and second 2D x-ray images of at least the portion of the tool and the skeletal portion from the 2D x-ray imaging device,
register the first and second 2D x-ray images to the 3D image data, the registering including:
  generating a plurality of 2D projections from the 3D image data, and
  identifying respective first and second 2D projections that match the first and second 2D x-ray images of the skeletal portion,
based upon the registration of the first and second 2D x-ray images to the 3D image data, derive a position of the designated location within at least one of the 2D x-ray images of the skeletal portion,
identify a location of at least a portion of the tool with respect to the at least one of the 2D x-ray images of the skeletal portion, by means of image processing, based upon the identified location of the portion of the tool, determine, within the at least one of the 2D x-ray images of the skeletal portion, a relationship between an anticipated longitudinal insertion path of the tool and the designated location, and
generate an output on the output device, at least partially in response thereto.

In some applications, the at least one computer processor is configured to receive the designation of a location within the skeletal portion with respect to the 3D image data by receiving a designation of a target location within the skeletal portion with respect to the 3D image data. In some applications, the at least one computer processor is configured to receive the designation of a location within the skeletal portion with respect to the 3D image data by receiving a designation of one or more locations that the tool should avoid within the skeletal portion with respect to the 3D image data.

In some applications, the at least one computer processor is configured to receive the designation of a location within the skeletal portion with respect to the 3D image data by receiving a designation of the location with respect to a cross-section of the skeletal portion that is derived from the 3D image data. In some applications, the at least one computer processor is configured to receive the designation of a location within the skeletal portion with respect to the 3D image data by receiving a designation of the location with respect to a 2D projection of the skeletal portion that is derived from the 3D image data. In some applications, the at least one computer processor is configured to receive the designation of a location within the skeletal portion with respect to the 3D image data by receiving a designation of the location with respect to a 3D image of the skeletal portion that is derived from the 3D image data.

There is further provided, in accordance with some applications of the present invention, apparatus for performing a procedure using a tool configured to be advanced into a skeletal portion within a body of a subject along a longitudinal insertion path, and for use with:

(a) a 3D imaging device configured to acquire 3D image data of the skeletal portion, (b) a 2D x-ray imaging device that is unregistered with respect to the subject's body and configured to sequentially:
  acquire a first 2D x-ray image of at least a portion of the tool and the skeletal portion from a first view, while the x-ray imaging device is disposed at a first pose with respect to the subject's body,
  be moved to a second pose with respect to the subject's body, and
  while the 2D x-ray imaging device is at the second pose, acquire a second 2D x-ray image of at least the portion of the tool and the skeletal portion from a second view, and (c) a display,
the apparatus including:
at least one computer processor configured to:
receive the 3D image data of the skeletal portion from the 3D imaging device,
receive the first and second 2D x-ray images of at least the portion of the tool and the skeletal portion from the 2D x-ray imaging device,
register the first and second 2D x-ray images to the 3D image data, the registering including:
  generating a plurality of 2D projections from the 3D image data, and
  identifying respective first and second 2D projections that match the first and second 2D x-ray images of the skeletal portion,
identify a location of a tip of the tool with respect to the first and second x-ray images of the skeletal portion, by means of image processing,
based upon the identified location of the tip of tool with respect to the first and second x-ray images of the skeletal portion, and the registration of the first and second x-ray images to the 3D image data, determine a location of the tip of the tool with respect to the 3D image data, and in response thereto, drive the display to display a cross-section of the skeletal portion, the cross-section being derived from the 3D image data, and corresponding to the location of the tool tip.

In some applications, the at least one computer processor is further configured to drive the display to display an indication of a location of the tool upon the cross-section of the skeletal portion. In some applications, the at least one computer processor is configured to drive the display to display the cross-section of the skeletal portion by driving the display to display a cross-sectional view selected from the group consisting of: an axial cross-section, a coronal cross-section, a sagittal cross-section, and a cross-sectional view that is based upon a direction of insertion of the tool.

There is further provided, in accordance with some applications of the present invention, apparatus for performing a procedure using a tool configured to be advanced into a given vertebra within a body of a subject along a longitudinal insertion path, and for use with:

(a) a 3D imaging device configured to acquire 3D image data of at least a portion of the subject's spine that contains the given vertebra, (b) a 2D x-ray imaging device that is unregistered with respect to the subject's body and configured to sequentially:
acquire a first 2D x-ray image of at least at least a portion of the tool and the portion of the subject's spine that contains the given vertebra from a first view, while the 2D x-ray imaging device is disposed at a first pose with respect to the subject's body,
be moved to a second pose with respect to the subject's body, and
while the 2D x-ray imaging device is at the second pose, acquire a second 2D x-ray image of at least a portion of the tool and at least the portion of the subject's spine that contains the given vertebra from a second view, and (c) an output device,
the apparatus including:
at least one computer processor configured to:
receive the 3D image data of at least the portion of the subject's spine that contains the given vertebra from the 3D imaging device,
receive the first and second 2D x-ray images of at least a portion of the tool and at least the portion of the subject's spine that contains the given vertebra from the 2D x-ray imaging device,
receive an input that is indicative of a location of the given vertebra within the 3D image data,
automatically determine a location of the given vertebra within the first and second x-ray images, by means of image processing,
register the given vertebra within the first and second 2D x-ray images to the given vertebra within the 3D image data, the registering including:
generating a plurality of 2D projections of the given vertebra from the 3D image data, and
identifying respective first and second 2D projections that match the given vertebra within the first and second 2D x-ray images of the skeletal portion,
identify a location of at least the portion of the tool with respect to the given vertebra within the first and second 2D x-ray images of the portion of the spine, by means of image processing,
based upon the registration of the given vertebra within the first and second 2D x-ray images to the given vertebra within the 3D image data, and the identified location of at least the portion of the tool, determine the location of at least the portion of the tool with respect to the given vertebra within the 3D image data, and
generate an output on the output device, in response thereto.

There is further provided, in accordance with some applications of the present invention, apparatus for use with a radiographic imaging device, an output device, and an instrument having a straight radiopaque component, the apparatus including:
at least one computer processor configured to:
receive from the radiographic image device, a radiographic image in which at least a portion the straight radiopaque component of the instrument is visible,
identify the straight radiopaque component of the instrument within the radiographic image, by means of image processing,
at least partially correct distortion in at least a portion of the radiographic image by deforming the portion of the radiographic image, such that the straight radiopaque component of the instrument within the radiographic image appears straight, and
generate an output on the output device, in response thereto.

In some applications, the at least one computer processor is further configured, based upon the correction applied to a portion of the image within which the straight radiopaque component of the instrument appeared, to correct an additional portion of the image.

In some applications, the at least one computer processor is further configured to register the corrected radiographic image to 3D image data. In some applications, the radiographic image includes the straight radiopaque component of the instrument and a portion of a body of a subject, and the at least one computer processor is configured to register the corrected radiographic image to the 3D image data, by: generating a plurality of 2D projections of the portion of the subject's body from the 3D image data, and identifying a 2D projection that matches the portion of the subject's body within the radiographic image.

There is further provided, in accordance with some applications of the present invention, apparatus for use with a procedure in which interventions are performed with respect to at least first and second vertebrae of a spine of a subject, a display, and an imaging device configured to acquire imaging data of the subject's spine, the apparatus including:
at least one computer processor configured to:
receive the imaging data from the imaging device,
generate, upon the display, a spinal roadmap image of at least a portion of the spine that contains the first and second vertebra,
automatically label vertebra within the spinal roadmap image,
determine that an intervention has been performed with respect to the first vertebra, such that an appearance of the first vertebra has changed, and
automatically update the spinal roadmap to reflect the change in the appearance of the first vertebra, such that the updated spinal roadmap is displayed while the intervention is performed with respect to the second vertebra.

In some applications, the imaging device includes an imaging device configured to acquire 3D imaging data, and the at least one computer processor is configured to generate the spinal roadmap image by generating a 3D spinal roadmap image. In some applications, the imaging device includes an imaging device configured to acquire 2D imaging data, and the at least one computer processor is configured to generate the spinal roadmap image by generating a 2D spinal roadmap image.

In some applications, the at least one computer processor is configured to determine that an intervention has been performed with respect to the first vertebra, such that an appearance of the first vertebra has changed by determining that a tool has been inserted into the first vertebra, and the at least one computer processor is configured to update the spinal roadmap by updating the spinal roadmap to display the tool inside the vertebra.

There is further provided, in accordance with some applications of the present invention, apparatus for use during a medical intervention in which a tool is used with respect to a portion of a body of a subject, and an imaging device that is used to acquire a plurality of images of the tool and the subject's body, during the intervention, the apparatus including:

at least one computer processor configured to determine a location of the tool with respect to the subject's body, by analyzing the plurality of images;

a motion detection sensor configured to be disposed upon the subject's body and to detect motion of at least the portion of the subject's body by detecting that its own motion has occurred relative to a prior position of itself, the motion detection sensor being configured to detect that, between acquisitions of two or more images, motion of at least a portion of the subject's body that exceeds a threshold amount has occurred; and an output device configured to generate an alert indicating that the motion has occurred, in response to the motion detection sensor detecting that motion of at least the portion of the subject's body that exceeds the threshold amount has occurred.

In some applications, the motion detection sensor is configured to drive the output device to generate the alert. In some applications, the at least one computer processor is configured to receive a signal from the sensor indicating that the motion of at least the portion of the subject's body that exceeds the threshold amount has occurred, and to drive the output device to generate the alert in response thereto. In some applications, the output device is configured to generate an output indicating that one or more images should be reacquired, in response to the motion detection sensor detecting that motion of at least the portion of the subject's body that exceeds the threshold amount has occurred.

There is further provided, in accordance with some applications of the present invention, apparatus for performing a procedure using a tool configured to be advanced into a given vertebra within a body of a subject along a longitudinal insertion path, and for use with:

(a) a 3D imaging device configured to acquire 3D image data of the skeletal portion, (b) a 2D x-ray imaging device that is unregistered with respect to the subject's body and configured to acquire one or more 2D x-ray images of at least at least a portion of the tool and the skeletal portion from a single view, while the 2D x-ray imaging device is disposed at a first pose with respect to the subject's body, and while a tip of the tool is disposed at a given location along the longitudinal insertion path, and (c) a display, the apparatus including:

at least one computer processor configured to:

receive the 3D image data of the skeletal portion from the 3D imaging device, receive the one or more 2D x-ray images of the skeletal portion from the 2D x-ray imaging device, register one of the one or more 2D x-ray images that were acquired from the single view to the 3D image data, the registering including:

generating a plurality of 2D projections from the 3D image data, and identifying a 2D projection that matches the one of the one or more 2D x-ray images of the skeletal portion that were acquired from the single view, identify a location of the tip of the tool with respect to the skeletal portion within the one of the one or more 2D x-ray images, by means of image processing, based upon the identified location of the tip of tool with respect to the skeletal portion within the one of the one or more 2D x-ray images, and the registration of the one of the one or more 2D x-ray images to the 3D image data, determine a location of the tip of the tool with respect to the 2D projection that matches the one of the one or more 2D x-ray images of the skeletal portion, and in response thereto, drive the display to display a cross-section of the skeletal portion, the cross-section being derived from the 3D image data, and corresponding to the location of the tool tip with respect to the 2D projection that matches the one of the one or more 2D x-ray images of the skeletal portion.

In some applications, the at least one computer processor is further configured to drive the display to display a line upon the cross-section, the line indicating that the location of the tool tip within the cross-section is somewhere along the line.

There is further provided, in accordance with some applications of the present invention, apparatus for use during a medical intervention in which a tool is used with respect to a portion of a body of a subject, and for use with:

(a) a 3D imaging device configured to acquire 3D image data of the portion of the subject's body, (b) a 2D x-ray imaging device that is unregistered with respect to the subject's body and configured to sequentially:

acquire a first 2D x-ray image of a distal portion of the tool and the portion of the subject's body from a first view, while the 2D x-ray imaging device is disposed at a first pose with respect to the subject's body, be moved to a second pose with respect to the subject's body, and while the 2D x-ray imaging device is at the second pose, acquire a second 2D x-ray image of the distal portion of the tool and the portion of the subject's body from a second view, and (c) a display, the apparatus including:

at least one computer processor configured to:

calculate a location of the proximal portion of the tool that is disposed outside the subject's body, based upon the calculated position of the proximal portion of the tool, derive a location of the distal portion of the tool with respect to the portion of the subject's body with respect to the 3D image data, based upon the derived location, drive the display to display an indication of the location of the distal portion of the tool with respect to the portion of the subject's body with respect to the 3D image data, subsequently:

receive from the 2D x-ray imaging device the first and second 2D x-ray images of the distal portion of the tool and the portion of the subject's body, register the portion of the subject's body within the first and second 2D x-ray images to the portion of the subject's body within the 3D image data, identify a location of at least the distal portion of the tool with respect to the portion of the subject's body within the first and second 2D x-ray images, by means of image processing, based upon the registration of the portion of the subject's body within the first and second 2D x-ray images to the portion of the subject's body within the 3D image data, and the identified location of at least the distal portion of the tool within the first and second 2D x-ray images, determine the location of at least the distal portion of the tool with respect to the portion of the subject's body with respect to the 3D image data, and based upon the determined location of at least the distal portion of the tool, drive the display to update the indication of the location of the distal portion of the tool with respect to the portion of the subject's body with respect to the 3D image data.

In some applications, the at least one computer processor is configured to register the portion of the subject's body within the first and second 2D x-ray images to the portion of the subject's body within the 3D image data, the registering including: generating a plurality of 2D projections of the portion of the subject's body from the 3D image data, and identifying respective first and second 2D projections that match the portion of the subject's body within the first and second 2D x-ray images of the portion of the subject's body.

In some applications, the apparatus further includes one or more location sensors coupled to the proximal portion of the tool, and the at least one computer processor is configured to calculate the location of the proximal portion of the tool that is disposed outside the subject's body by means of the one or more location sensors that are coupled to the proximal portion of the tool. In some applications, the at least one computer processor is configured to calculate the location of the proximal portion of the tool that is disposed outside the subject's body by video tracking the proximal portion of the tool. In some applications, the apparatus further includes a robot, the proximal portion of the tool being coupled to a portion of the robot, and the at least one computer processor is configured to calculate the location of the proximal portion of the tool that is disposed outside the subject's body by means of tracking the portion of the robot relative to a prior known position of the portion of the robot.

The present invention will be more fully understood from the following detailed description of embodiments thereof, taken together with the drawings, in which:

BRIEF DESCRIPTION OF THE DRAWINGS

FIG. 1B is a schematic illustration of a system for use with procedures that are performed on skeletal anatomy, in accordance with some applications of the present invention;

FIGS. 5A, 5B, 5C, 5D, and 5E are schematic illustration of sets of radiopaque markers which are placed upon a subject, in accordance with some applications of the present invention;

FIG. 8A shows a vertebra designated upon cross-sectional images of a subject's spine that are derived from 3D image data, in accordance with some applications of the present invention;

FIG. 8B shows an example of a 3D CT image of a subject's spine displayed alongside a combined radiographic image of the subject's spine, in accordance with some applications of the present invention;

FIG. 10 shows an example of a 2D radiographic (e.g., x-ray) image displayed alongside a cross-sectional image of a subject's vertebra that is derived from 3D image data of the vertebra, in accordance with some applications of the present invention;

FIGS. 11A and 11B show examples of respectively AP and lateral x-ray images of a Jamshidi™ needle being inserted into a subject's spine, in accordance with some applications of the present invention;

FIGS. 13A, 13B, and 13C are schematic illustrations that demonstrate the relationship between a 3D image of an object (which in the example shown in FIG. 13A is a cone) and side-to-side (FIG. 13B) and bottom-to-top (FIG. 13C) 2D projection images of the object, such a relationship being utilized, in accordance with some applications of the present invention;

DETAILED DESCRIPTION OF EMBODIMENTS

Figure 1A:
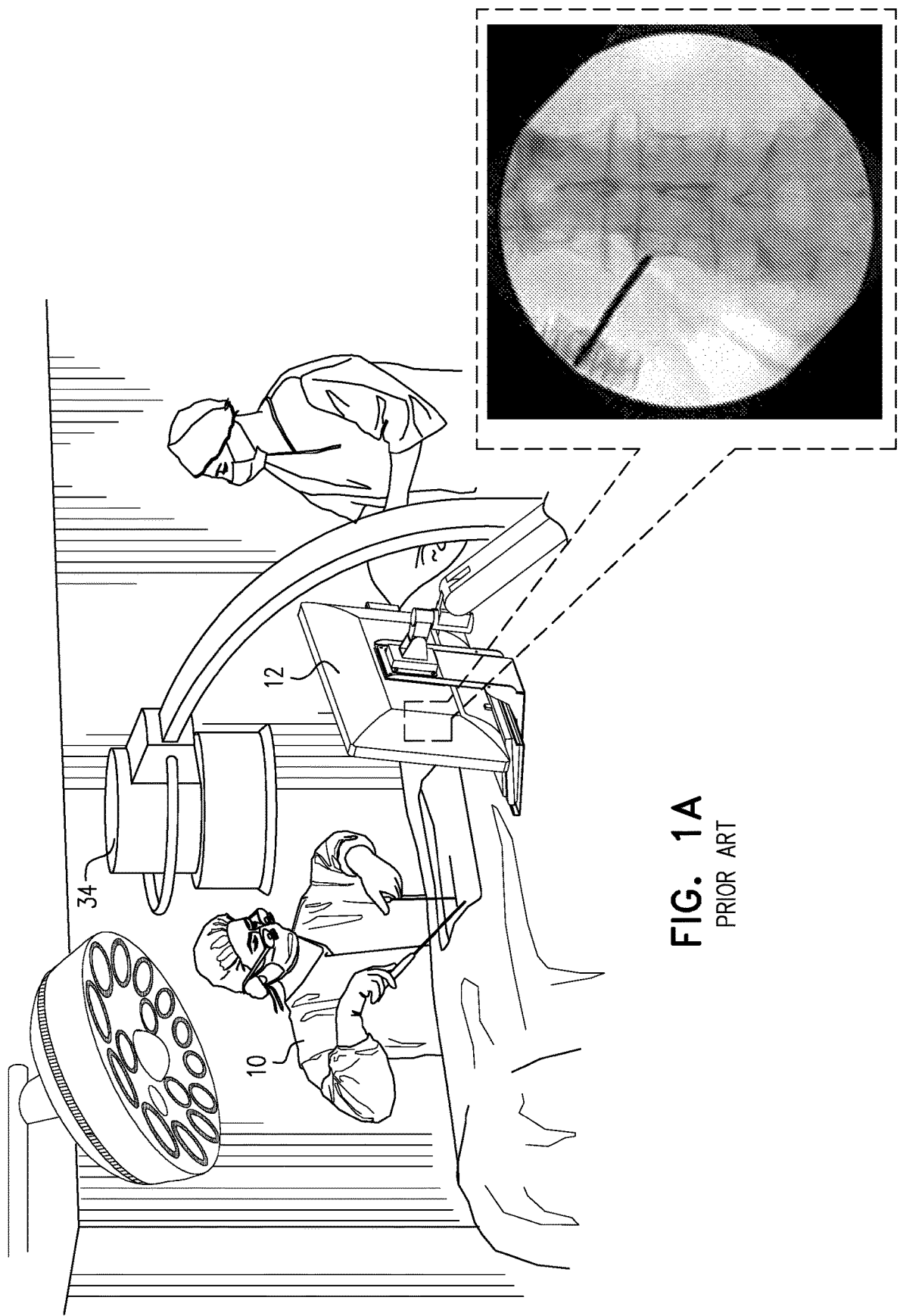
FIG. 1A is a schematic illustration of an orthopedic operating room, as used in prior art techniques.

Reference is now made to FIG. 1B, which is a schematic illustration of a system 20 for use with procedures that are performed on skeletal anatomy, in accordance with some applications of the present invention. For some applications, the system is used for a procedure that is performed on one or more vertebrae of a subject's spine. However, the scope of the present invention includes applying any of the apparatus and methods described herein to procedures performed on other portions of a subject's skeletal anatomy, mutatis mutandis. Such procedures may include joint (e.g., shoulder, knee, hip, and/or ankle) replacement, joint repair, fracture repair (e.g., femur, tibia, and/or fibula), a procedure that is performed on a rib (e.g., rib removal, or rib resection), and/or other interventions in which 3D image data are acquired prior to the intervention and 2D images are acquired during the intervention.

System 20 typically includes a computer processor 22, which interacts with a memory 24, and one or more user interface device 26. Typically, the user interface devices include one or more input devices, such as a keyboard 28 (as shown), and one or more output devices, e.g., a display 30, as shown. Inputs to, and outputs from, the computer processor that are described herein are typically performed via the user interface devices. For some applications, the computer processor as well as the memory and the user interface devices, are incorporated into a single unit, e.g., a tablet device, and/or a laptop computer.

For some applications, the user interface devices include a mouse, a joystick, a touchscreen device (such as a smartphone or a tablet computer), a touchpad, a trackball, a voice-command interface, and/or other types of user interfaces that are known in the art. For some applications, the output device includes a head-up display and/or a head-mounted display, such as Google Glass®. For some applications, the computer processor generates an output on a different type of visual, text, graphics, tactile, audio, and/or video output device, e.g., speakers, headphones, a smartphone, or a tablet computer. For some applications, a user interface device acts as both an input device and an output device. For some applications, computer processor 22 generates an output on a computer-readable medium (e.g., a non-transitory computer-readable medium), such as a disk or a portable USB drive. For some applications, the computer processor comprises a portion of a picture archiving and communication system (PACS), and is configured to receive inputs from other components of the system, e.g., via memory 24. Alternatively or additionally, the computer processor is configured to receive an input on a computer-readable medium (e.g., a non-transitory computer-readable medium), such as a disk or a portable USB drive. It is noted that, for some applications, more than one computer processor is used to perform the functions described herein as being performed by computer processor 22.

Typically, 3D image data are acquired before the subject is in the operating room for the procedure, or when the subject is in the operating room, but before an intervention has commenced. For example, 3D CT image data of the portion of the skeletal anatomy upon which the procedure is to be performed (and/or neighboring portions of the anatomy) may be acquired using a CT scanner 32. Alternatively or additionally, 3D MRI image data of the portion of the skeletal anatomy upon which the procedure is to be performed (and/or neighboring portions of the anatomy) may be acquired using an MRI scanner. For some applications, 3D x-ray data are acquired. Typically, the 3D image data are transferred to memory 24, and are retrieved from the memory by computer processor 22. It is noted that for illustrative purposes, FIG. 1B shows the CT scanner, the C-arm, and system 20 together with one another. However, in accordance with the above description, for some applications, the CT scanner is not disposed in the same room as system 20, and/or C-arm 34.

During the procedure, real time 2D images are acquired by a radiographic imaging device, e.g., a C-arm 34 (as shown), which acquires 2D x-ray images. For some applications, the 2D images are captured in real time by a frame grabber of system 20 that is connected to an output port of the C-arm. Alternatively or additionally, system 20 and the C-arm are connected to one another via a PACS network to which system 20 and C-arm 34 are connected, and the 2D images are transferred, once acquired, to system 20 via the PACS network (e.g., via memory 24). Alternatively or additionally, the C-arm sends image files, for example in DICOM format, directly to system 20 (e.g., via memory 24).

Typically, the interventional part of a procedure that is performed on skeletal anatomy, such as the spine, commences with the insertion of a tool, such as a Jamshidi™ needle 36. A Jamshidi™ needle typically includes an inner tube and an outer tube. The Jamshidi™ needle is typically inserted to a target location, at which point other tools and/or implants are inserted using the Jamshidi™ needle. Typically, in open surgery, for lower-diameter tools and/or implants, the inner tube of the Jamshidi™ needle is removed, and the tool and/or implant is inserted via the outer tube of the Jamshidi™ needle, while for larger-diameter tools and/or implants, the tool and/or implant is inserted by removing the inner tube of the Jamshidi™ needle, inserting a stiff wire through the outer tube, removing the outer tube, and then inserting the tool and/or implant along the stiff wire. For minimally-invasive surgery, the aforementioned steps (or similar steps thereto) are typically performed via small incisions.

It is noted that, in general throughout the specification and the claims of the present application, the term "tool" should be interpreted as including any tool or implant that is inserted into any portion of the skeletal anatomy during a procedure that is performed upon the skeletal anatomy. Such tools may include flexible, rigid and/or semi-rigid probes, and may include diagnostic probes, therapeutic probes, and/or imaging probes. For example, the tools may include Jamshidi™ needles, other needles, k-wires, pedicle markers, screws, nails, other implants, implant delivery probes, drills, endoscopes, probes inserted through an endoscope, tissue ablation probes, laser probes, balloon probes, injection needles, tissue removal probes, drug delivery probes, stimulation probes, dilators, etc. Typically, such procedures include spinal stabilization procedures, such as vertebroplasty (i.e., injection of synthetic or biological cement in order to stabilize spinal fractures), kyphoplasty (i.e., injection of synthetic or biological cement in order to stabilize spinal fractures, with an additional step of inflating a balloon within the area of the fracture prior to injecting the cement), fixation (e.g., anchoring two or more vertebrae to each other by inserting devices such as screws into each of the vertebrae and connecting the screws with rods), fixation and fusion (i.e., fixation with the additional step of an implant such as a cage placed in between the bodies of the vertebrae), and/or endoscopy (i.e., inserting an endoscope toward a vertebra and/or a disc, for example, in order to remove tissue (e.g., disc tissue, or vertebral bone) that compresses nerves).

Figure 2:
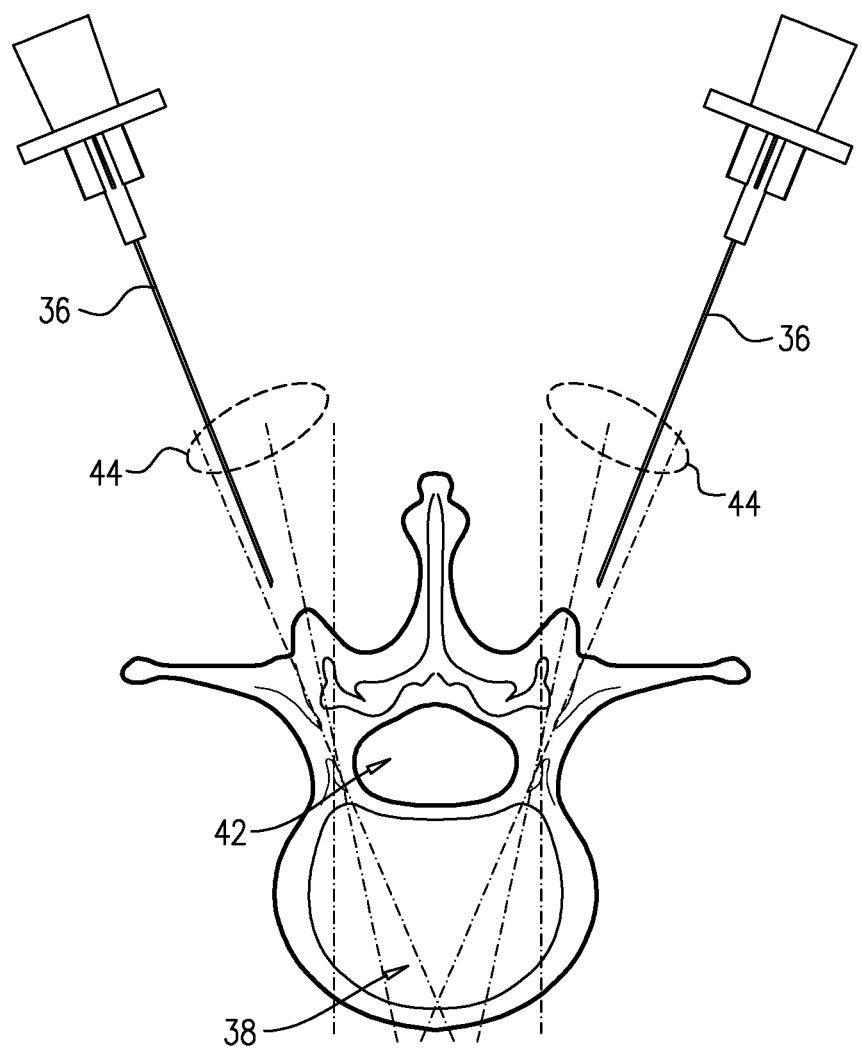
FIG. 2 is a schematic illustration of two tools (e.g., Jamshidi™ needles) being inserted into a vertebra and the desired insertion windows for the insertion of such tools, as used in prior art techniques.

Reference is now made to FIG. 2, which is a schematic illustration of two Jamshidi™ needles 36 being inserted into a vertebra 38, as used in prior art techniques. Typically, a spinal intervention aimed at a vertebral body is performed with tools being aimed at 10-11 o'clock and 1-2 o'clock insertion windows with respect to the subject's spine. Tool insertion into a vertebra must avoid the spinal cord 42, and additionally needs to avoid exiting the vertebra from the sides, leaving only two narrow insertion windows 44, on either side of the vertebra. As described hereinbelow with reference to FIGS. 3A-4B, typically the most important images for determining the locations of the insertion windows are those derived from 3D image data, and are not available from the real time 2D images that are typically acquired during the intervention.

Figure 3A:
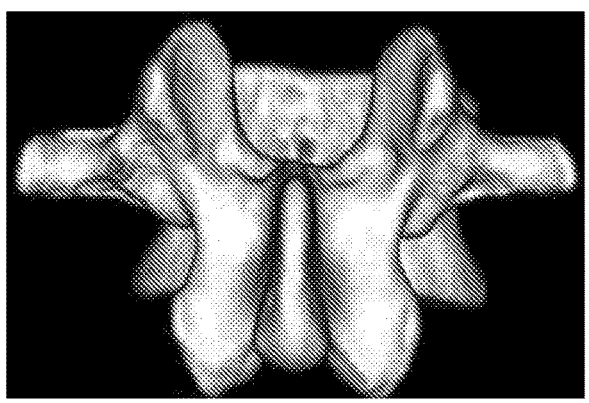
FIGS. 3A and 3B are schematic illustrations of a 3D CT image of a vertebra (FIG. 3A), as well as a 2D axial slice that is derived from the 3D CT image (FIG. 3B), as used in prior art techniques.
Figure 3B:
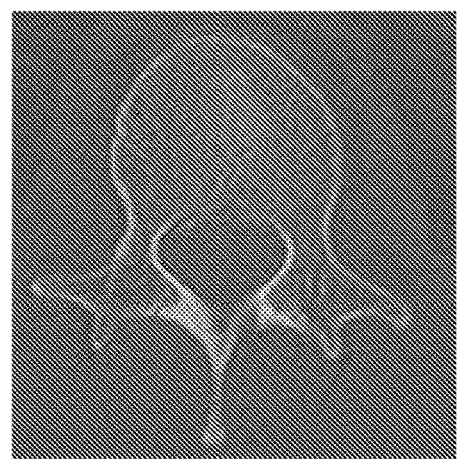
Figure 4A:
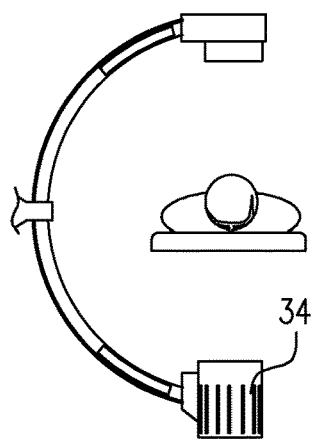
FIGS. 4A and 4B show a C-arm being used to acquire an anterior-posterior ("AP") 2D radiographic image and a resultant AP image (FIG. 4A), and the C-arm being used to acquire a lateral 2D radiographic image and a resultant lateral image (FIG. 4B), as used in prior art techniques.
Figure 4A:
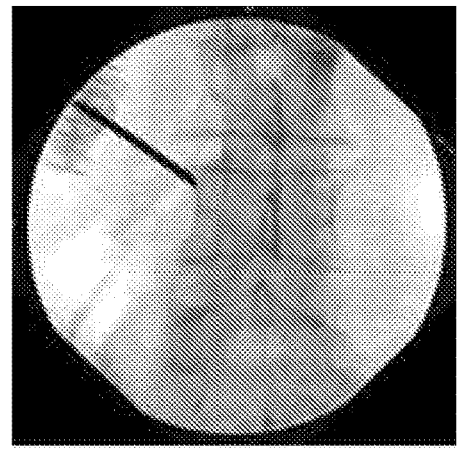
Figure 4B:
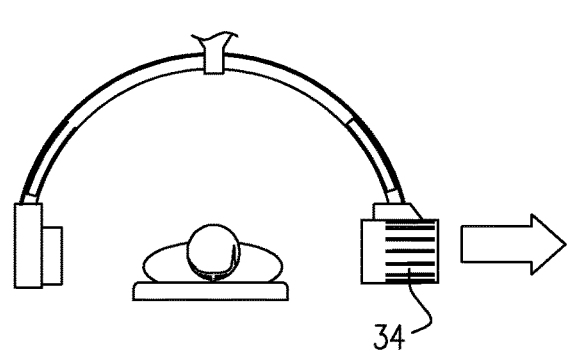

Reference is now made to FIGS. 3A and 3B, which are schematic illustrations of a 3D CT image of a vertebra (FIG. 3A), as well as a 2D axial slice that is derived from the 3D CT image (FIG. 3B), such images being used in prior art techniques. Reference is also made to FIGS. 4A and 4B, which show C-arm 34 being used to acquire an anterior-posterior ("AP") 2D radiographic image and a resultant AP image (FIG. 4A), and C-arm 34 being used to acquire a lateral 2D radiographic image and a resultant lateral image (FIG. 4B), as used in prior art techniques.

As may be observed, the view of the vertebra that is important for determining the entry point, insertion direction, and insertion depth of the tool is shown in the axial 2D image slice of FIG. 3B. By contrast, the 2D radiographic images that are acquired by the C-arm are summations of 3D space, and do not show cross-sectional views of the vertebra. As described hereinabove, Computer Aided Surgery (CAS) systems typically make use of CT and/or MRI images, generated before the subject has been placed in the operating room, or once the subject has been placed in the operating room but typically before an intervention has commenced. However, such procedures are typically more expensive than non-CAS procedures (such non-CAS procedures, including open procedures, mini-open procedures, and minimally-invasive procedures), limit tool selection to those fitted with location sensors as described above, and require such tools to be individually identified and calibrated at the beginning of each surgery.

In accordance with some applications of the present invention, the intra-procedural location of a tool is determined with respect to 3D image data (e.g., a 3D image, a 2D cross-section derived from 3D image data, and/or a 2D projection image derived from 3D image data), in a non-CAS procedure (e.g., in an open, mini-open and/or minimally-invasive procedure). The techniques described herein are typically practiced without requiring the fitting of location sensors (such as infrared transmitters or reflectors, or magnetic or electromagnetic sensors) to the tool or to the subject, and without requiring identification and/or calibration of tools prior to the procedure. The techniques described herein typically do not require tracking the location of the subject's body or the applicable portion of the subject's body, and do not assume any knowledge of the location coordinates of the subject's body in some reference frame. The techniques described herein typically do not require location sensors that rely upon tracking technologies (e.g., electromagnetic or IR tracking technologies) that are not typically used in an orthopedic operating room. Further typically, the techniques described herein are practiced without requiring knowledge of the precise parameters of any individual pose of the 2D radiographic imaging device (e.g., C-arm 34), and without requiring poses of the 2D radiographic imaging device (e.g., C-arm 34) to be tracked relative to each other, and/or relative to the position of the subject. For some applications, 2D radiographic images (e.g., 2D x-ray images) are acquired from two or more views, by moving a radiographic imaging device to respective poses between acquisitions of the images of respective views. Typically, a single x-ray source is used for acquisition of the 2D x-ray images, although, for some applications, multiple sources are used. In general, where views of the 2D radiographic imaging device are described herein as being AP, lateral, oblique, etc., this should not be interpreted as meaning that images must be acquired from precisely such views, rather acquiring images from generally such views is typically sufficient. Typically, the techniques described herein are tool-neutral, i.e., the techniques may be practiced with any applicable tool and typically without any modification and/or addition to the tool.

It is noted that although some applications of the present invention are described with reference to 3D CT imaging, the scope of the present invention includes using any 3D imaging, e.g., MRI, 3D x-ray imaging, and/or other modalities of 3D imaging, mutatis mutandis. Such imaging may be performed prior to, at the commencement of, and/or at some point during, an intervention. For example, the 3D imaging may be performed before the subject has been placed within the operating room, when the subject is first placed within the operating room, or at some point when the subject is in the operating room, but prior to the insertion of a given tool into a given target portion. Similarly, although some applications of the present invention are described with reference to 2D radiographic or x-ray imaging, the scope of the present invention includes using any 2D imaging, e.g., ultrasound and/or other modalities of 2D imaging, mutatis mutandis. Although some applications of the present invention are described with reference to procedures that are performed on skeletal anatomy and/or vertebrae of the spine, the scope of the present invention includes applying the apparatus and methods described herein to other orthopedic interventions (e.g., a joint (e.g., shoulder, knee, hip, and/or ankle) replacement, joint repair, fracture repair (e.g., femur, tibia, and/or fibula), a procedure that is performed on a rib (e.g., rib removal, or rib resection), vascular interventions, cardiovascular interventions, neurovascular interventions, abdominal interventions, therapeutic irradiations, and/or interventions performed on other portions of a subject, including interventions in which 3D image data are acquired prior to the intervention and 2D images are acquired during the intervention, mutatis mutandis.

Reference is now made to FIGS. 5A, 5B, 5C, 5D, and 5E, which are schematic illustration of sets 50 of radiopaque markers 52 which are typically placed on a subject, in accordance with some applications of the present invention. For some applications, the sets of markers are disposed on a drape 53, as shown. Drape 53 is typically sterile and disposable. For some applications, the set of markers includes an authentication and/or an anti-copying element, such as RFID, bar code(s), etc.

Figure 5E:
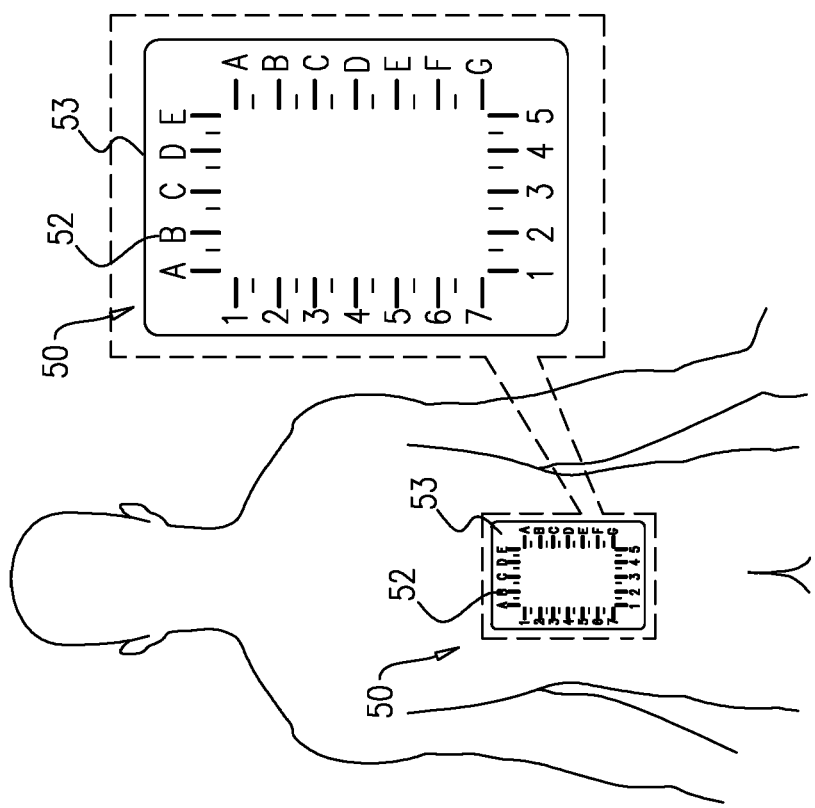
Figure 5D:
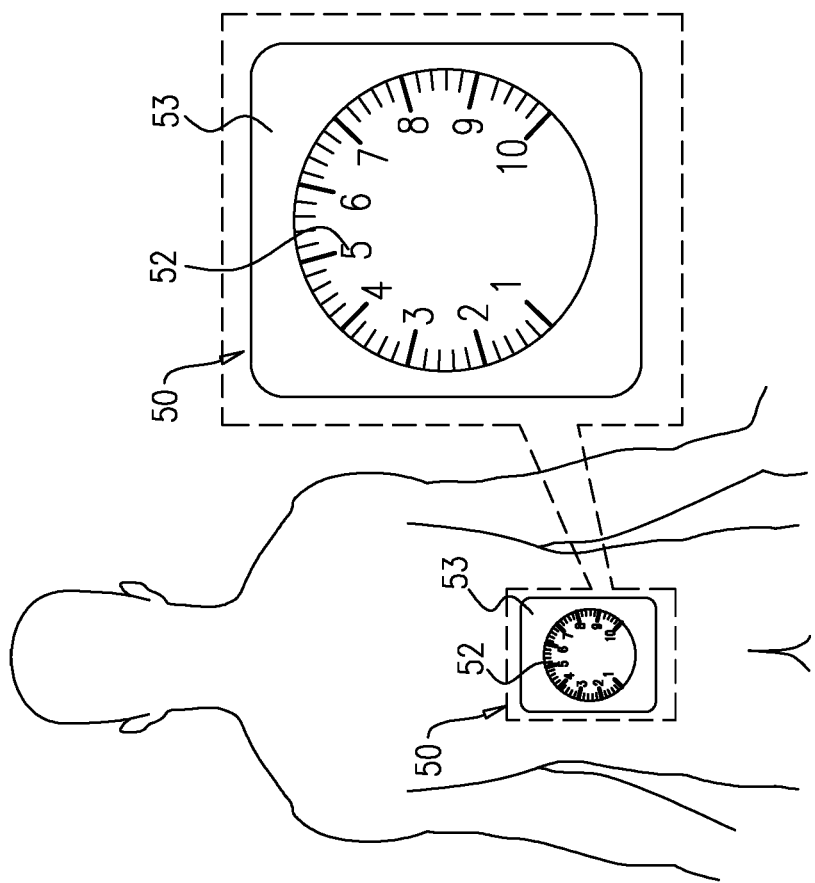

Typically, sets 50 of markers 52 are placed on or near the subject in a vicinity of a site at which an intervention is to be performed, and such that at least some of the markers appear in 2D radiographic images that are acquired of the intervention site from typical imaging views for such an intervention. For example, for a procedure that is performed on the subject's spine, the markers are typically placed on the subject's back in a vicinity of the site of the spinal intervention, such that at least some of the markers appear in 2D radiographic images that are acquired of the intervention site from AP imaging views (as shown in FIGS. 5B, 5C, 5D, and 5E). For some applications, the markers are placed on the subject's side in a vicinity of the site of the spinal intervention, such that at least some of the markers appear in 2D radiographic images that are acquired of the intervention site from a lateral imaging view (FIG. 5A). For some applications, the markers are placed on the subject's back, such that at least some of the markers are level with the subject's sacrum. As shown the markers may be arranged in a line (e.g., like a ruler, FIG. 5A), a grid (FIG. 5B), a pair of parallel lines (FIG. 5C), a frame around a surgical site (e.g., a circle (FIG. 5D), or a rectangle (FIG. 5E)), and/or any other shape. For some applications, the markers include one or more meshes, and/or a set of discrete elements that are connected (virtually or physically) into one or more meshes.

For some applications, the set of markers comprises an arrangement wherein portions thereof are visible from different image views, for example, the arrangement may include two rulers one of which is positioned on the subject's back (e.g., as shown in FIG. 5C), such as to be visible in an image acquired from an AP view, and the other one of which is positioned on the subject's side (e.g., as shown in FIG. 5A), such as to be visible in an image acquired from a lateral view. For some applications (not shown), the set of markers is a rigid arrangement of identifiable radiopaque features, for example, a notched radiopaque ruler, placed on or attached to the surgical table.

Typically, surgery on skeletal anatomy commences with attaching a sterile surgical drape at and around the surgical site. In the case of spinal surgery, the surgical approach may be anterior, posterior, lateral, oblique, etc., with the surgical drape placed accordingly. For such applications, sets 50 of markers 52 are typically placed above the surgical drape. Alternatively, sets of markers are placed on the subject's skin (e.g., if no surgical drape is used). For some applications, sets of markers are placed under the subject's body, on (e.g., attached to) the surgical table, and/or such that some of the markers are above the surgical table in the vicinity of the subject's body. For some applications, a plurality of sets of markers are used. For example, multiple sets of markers may be placed adjacently to one another. Alternatively or additionally, one or more sets of markers may be placed on the subject's body such that at least some markers are visible in each of a plurality of x-ray image views, e.g., on the back or stomach and/or chest for the AP or PA views, and on the side of the body for the lateral view. For some applications, a single drape 53 with markers disposed thereon extends, for example, from the back to the side, such that markers are visible in both AP and lateral x-ray image views.

Figure 6A:
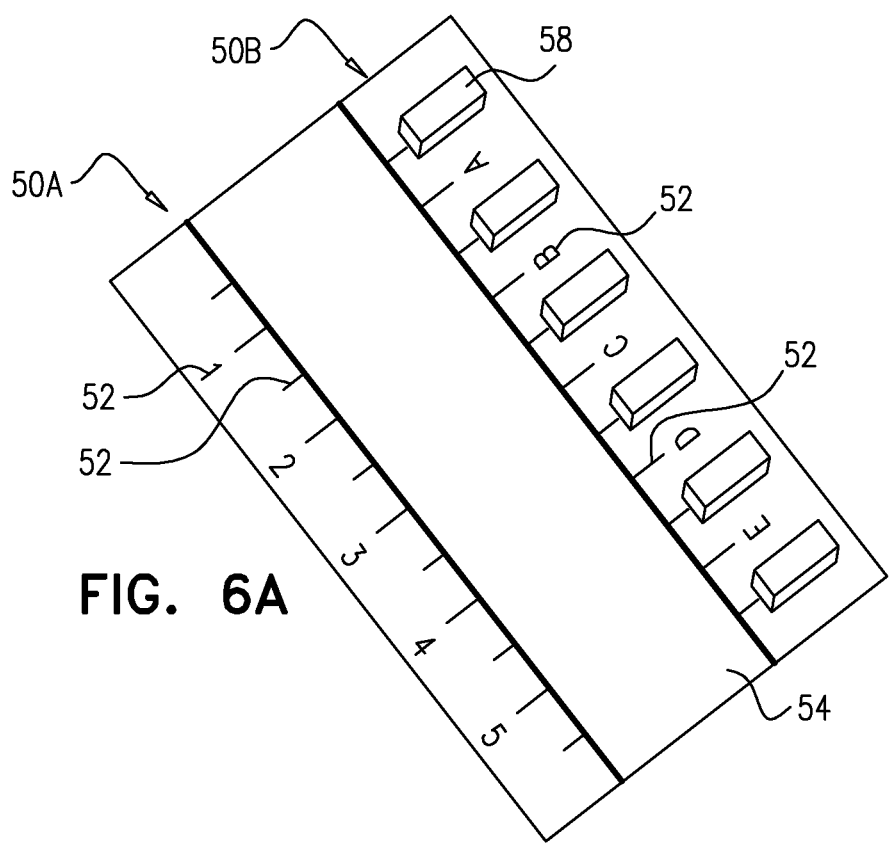
FIGS. 6A and 6B are schematic illustrations of first and second sets of radiopaque markers configured to be placed on a subject, in accordance with some applications of the present invention.
Figure 6B:
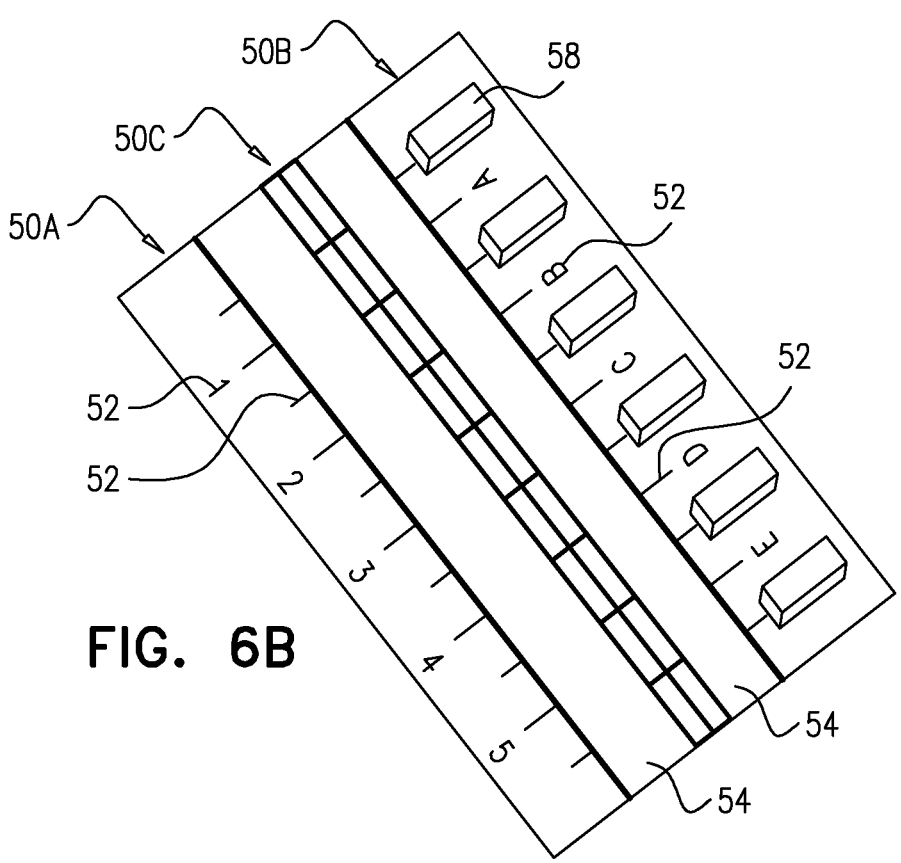

Reference is also made to FIGS. 6A and 6B, which are schematic illustrations of first and second sets 50A and 50B of radiopaque markers 52 configured to be placed on a subject, in accordance with some applications of the present invention. For some applications, the first and second sets of radiopaque markers are coupled to one another via the one or more surfaces 54. For example, the one or more surfaces may comprise a portion of drape 53. The one or more surfaces are configured to position the first and second sets of markers on respective sides of the subject's spine, in predefined positions with respect to one another (e.g., parallel and/or with one or both ends of each of the sets aligned with one another), by the one or more surfaces being placed over a portion of the subject's spine upon which the procedure is to be performed. Subsequent to positioning the first and second set of markers on the respective sides of the subject's spine, the one or more surfaces are configured to be removable from the subject's body (for example, the surfaces may be peeled off), such as to facilitate performance of the procedure upon the portion of the subject's spine over which the one or more surfaces were placed, while leaving the first and second sets of markers on the respective sides of the subject's spine, in their predefined positions with respect to one another.

Typically, the sets of markers are thereby positioned in a desired relationship with respect to one another (e.g., parallel and/or with one or both ends of each of the sets aligned with one another). However, by virtue of removing surface(s) 54, fragments of the surface(s) are prevented from entering the body, and/or interfering with the intervention. Typically, the sets of markers are positioned on either side of the subject's spine such that even in oblique x-ray image views of the intervention site (and neighboring portions of the spine), at least markers belonging to one of the sets of markers are visible. Further typically, the sets of markers are positioned on either side of the subject's spine such that even in zoomed-in views acquired from the direction of the tool insertion, or in views that are oblique (i.e., diagonal) relative to the direction of tool insertion, at least markers belonging to one of the sets of markers are visible. Typically, the sets of radiopaque markers are placed on the subject, such that the radiopaque markers do not get in the way of either AP or lateral x-ray images of vertebrae, such that the radiopaque markers do not interfere with the view of the surgeon during the procedure, and do not interfere with registration of 2D and 3D image data with respect to one another (which, as described hereinbelow, is typically based on geometry of the vertebrae).

Typically, the sets of markers as shown in FIG. 6A are used in open-surgery procedures. For such procedures, a relatively large central window is required for performing the procedure between the two sets of markers.

Typically, minimally-invasive spinal interventions are performed via small incisions aimed at 10-11 o'clock and 1-2 o'clock insertion windows. For some such applications, an additional marker set 50C is placed along a site that is between the 11 o'clock and 1 o'clock positions, as shown in FIG. 6B. The additional set of markers is positioned with respect to the first and second sets of markers, such that the additional set of markers is placed along a center of the subject's spine, when the first and second sets of markers are placed along respective sides of the spine. For such applications, when surfaces 54 are removed, an intervention is typically performed via incisions aimed at 10-11 o'clock and 1-2 o'clock insertion windows, which are disposed, respectively, between marker sets 50A and 50C, and between marker sets 50B and 50C.

Radiopaque markers 52 typically include markings (e.g., lines, notches, numbers, characters, shapes) that are visible to the naked eye as well as to the imaging that is applied. Typically, the markers are radiopaque such that the markers are visible in radiographic images. Further typically, markers that are placed at respective locations with respect to the subject are identifiable. For example, as shown in FIGS. 6A and 6B respective radiopaque alphanumeric characters are disposed at respective locations. For some applications, markers placed at respective locations are identifiable based upon other features, e.g., based upon the dispositions of the markers relative to other markers. Using a radiographic imaging device (e.g., C-arm 34), a plurality of radiographic images of the set of radiopaque markers are acquired, respective images being of respective locations along at least a portion of the subject's spine and each of the images including at least some of the radiopaque markers.

As shown in FIGS. 6A-6B, typically, each of the sets of markers includes radiopaque notches. For some applications, to facilitate interpretation of the images and, for example, to avoid confusion when only one ruler is visible, each of the sets of markers is additionally marked with a respective set of radiopaque characters, the sets being different from one another. For example, as shown, set 50A is marked with numbers and set 50B is marked with letters.

Typically, drape 53 is made of a flexible material that is configured to generally conform to contours of the subject's body. For some applications, at least some of radiopaque markers 52 are rigid and have respective known dimensions. For example, markers 58 shown in FIGS. 6A and 6B may be rigid. The rigid radiopaque markers are disposed upon the flexible material, such that, typically, rigidity of the rigid markers does not prevent the flexible material from generally conforming to the contours of the subject's body. Typically, computer processor 22 identifies, by means of image processing, at least one of the rigid radiopaque markers within a radiographic image of the spine acquired by the radiographic imaging device (e.g., C-arm 34), and based upon the identified rigid radiopaque markers, determines dimensions of features within the radiographic image (e.g., features that were automatically identified, and/or features designated by an operator of system 20), by means of image processing. In accordance with respective applications, the rigid markers are 2D or 3D, and are radiopaque in whole or in part.

For some applications, rigid radiopaque markers (and/or a rigid radiopaque jig) that appear in a plurality of different in x-ray image views of the subject are used to aid registering x-ray images to one another, in general accordance with techniques described herein. For some applications, rigid radiopaque markers (and/or a rigid radiopaque jig) that appear in a plurality of different in x-ray image views of the subject are used to aid registering x-ray images to 3D image data (e.g., to CT image data) and/or to one another, in general accordance with techniques described herein.

For some applications, an arrangement similar to the arrangement shown and described with reference to FIG. 6A is applied to first and second sets of radiopaque markers, the first set 50A being positioned such that it is visible from the intended direction of intervention (for example, dorsal) corresponding to a first anticipated view of the x-ray imaging (for example, AP) and the second set 50B being positioned such that it is visible from a secondary direction (for example, lateral) corresponding to a second anticipated view of the x-ray imaging (for example, a left lateral view or a right lateral view). The spatial relationship of the marker sets to one another is known, for example, it may be defined by the one or more surfaces 54 via which the marker sets are coupled to each other. (For some applications, such surfaces are removable as described hereinabove.) Once applied to the subject, the two marker sets 50A and 50B typically facilitate the association of specific vertebrae, as seen in one x-ray view (for example, an AP view), with same vertebrae as seen in a second x-ray view (for example, a left lateral or a right lateral view). For some applications, such association is performed manually by the surgeon referring to the radiopaque markers, e.g., by the surgeon identifying markers that have a known association with one another in the x-ray images, e.g., via matching of alphanumeric characters. Alternatively or additionally, the association is performed automatically by computer processor 22 of system 20 by means of image processing, such as by identifying markers that have a known association with one another in the x-ray images, e.g., via pattern matching, or via optical character recognition.

For some applications, sets 50 of markers 52, and/or a rigid radiopaque jig, as described hereinabove, are used to facilitate any one of the following functionalities:

Vertebra level verification, as described hereinbelow.

Arriving at a desired vertebra intra-procedurally, without requiring needles to be stuck into the patient, and/or counting along a series of non-combined x-rays.

Displaying a 3D image of the spine that includes indications of vertebra thereon, using vertebral level verification.

Determining the correct incision site(s) prior to actual incision(s).

Providing a reference scale with some known dimensions/intervals, e.g., by using rigid markers 58 to provide reference dimensions, and/or by comparing known shapes and/or sizes, e.g. of rigid markers 58, to what is seen in an image (e.g., in order to determine the extent of foreshortening in the image).

Performing measurements on images of the subject, e.g., by using the rigid markers to provide reference dimensions, and/or by comparing known shapes and/or sizes, e.g. of the rigid markers 58, to what is seen in an image (e.g., in order to determine the extent of foreshortening in the image).

Registration of 2D radiographic images to 3D image data. In this regard, it is noted that if the 3D image data were acquired in the operating room, then markers 52 and rigid markers 58 may be observable in the 3D image data and at least some of the 2D images, which typically further facilitates registration. If the 3D image data were acquired previously, the 3D imaging data typically includes some built-in dimensions, which the 2D image data typically do not. Rigid markers 58 provide reference dimensions in the 2D images, which for some applications may be used as an additional input to register the 2D images to the 3D image data.

Identifying changes in a pose of the 2D imaging device (e.g., the x-ray C-arm) and/or a position of the patient. Typically, if the position of the 2D imaging device relative to the subject, or the position of the subject relative to the 2D imaging device, has changed, then in the 2D images there would be a visible change in the appearance of the markers 52 relative to the anatomy within the image. For some applications, in response to detecting such a change, the computer processor generates an alert. Alternatively or additionally, the computer processor may calculate the change in position, and account for the change in position, e.g., in the application of algorithms described herein. Further alternatively or additionally, the computer processor assists the surgeon in returning the 2D imaging device to a previous position relative to the subject. For example, the computer processor may generate directions regarding where to move an x-ray C-arm, in order to replicate a prior imaging position, or the computer processor may facilitate visual comparison by an operator.

Providing a reference for providing general orientation to the surgeon throughout a procedure.

Providing information to the computer processor regarding the orientation of image acquisition and/or tool insertion, e.g., anterior-posterior ("AP") or posterior-anterior ("PA"), left lateral or right lateral, etc.

Generating and updating a visual roadmap of the subject's spine, as described in further detail hereinbelow.

For some applications, at least some of the functionalities listed above as being facilitated by use of sets 50 of markers 52, and/or a rigid jig are performed by computer processor 22 even in the absence of sets 50 of markers 52, and/or a rigid jig, e.g., using techniques as described herein. Typically, sets 50 of markers 52, and/or a rigid jig are used for level verification, the determination of a tool entry point or an incision site, performing measurements using rigid markers as a reference, identifying changes in a relative pose of the 2D imaging device (e.g., the x-ray C-arm) and of the subject, and providing general orientation. All other functionalities of system 20 (such as registration of 2D images to 3D image data and other functionalities that are derived therefrom) typically do not necessarily require the use of sets 50 of markers 52, and/or a rigid jig. The above-described functionalities may be performed automatically by computer processor 22, and/or manually.

Applications of the present invention are typically applied, in non-CAS spinal surgery, to one or more procedural tasks including, without limitation:

Applying pre-operative 3D visibility (e.g., from CT and/or MRI) during the intervention. It is noted that 3D visibility provides desired cross-sectional images (as described in further detail hereinbelow), and is typically more informative and/or of better quality than that provided by intraoperative 2D images. (It is noted that, for some applications, intraoperative 3D imaging is performed.)

Confirming the vertebra(e) to be operated upon.

Determining the point(s) of insertion of one or more tools.

Determining the direction of insertion of one or more tools.

Monitoring tool progression, typically relative to patient anatomy, during insertion.

Reaching target(s) or target area(s).

Exchanging tools while repeating any of the above steps.

Determining tool/implant position within the anatomy, including in 3D.

Generating and updating a visual roadmap of the subject's spine, as described in further detail hereinbelow.

Figure 7:
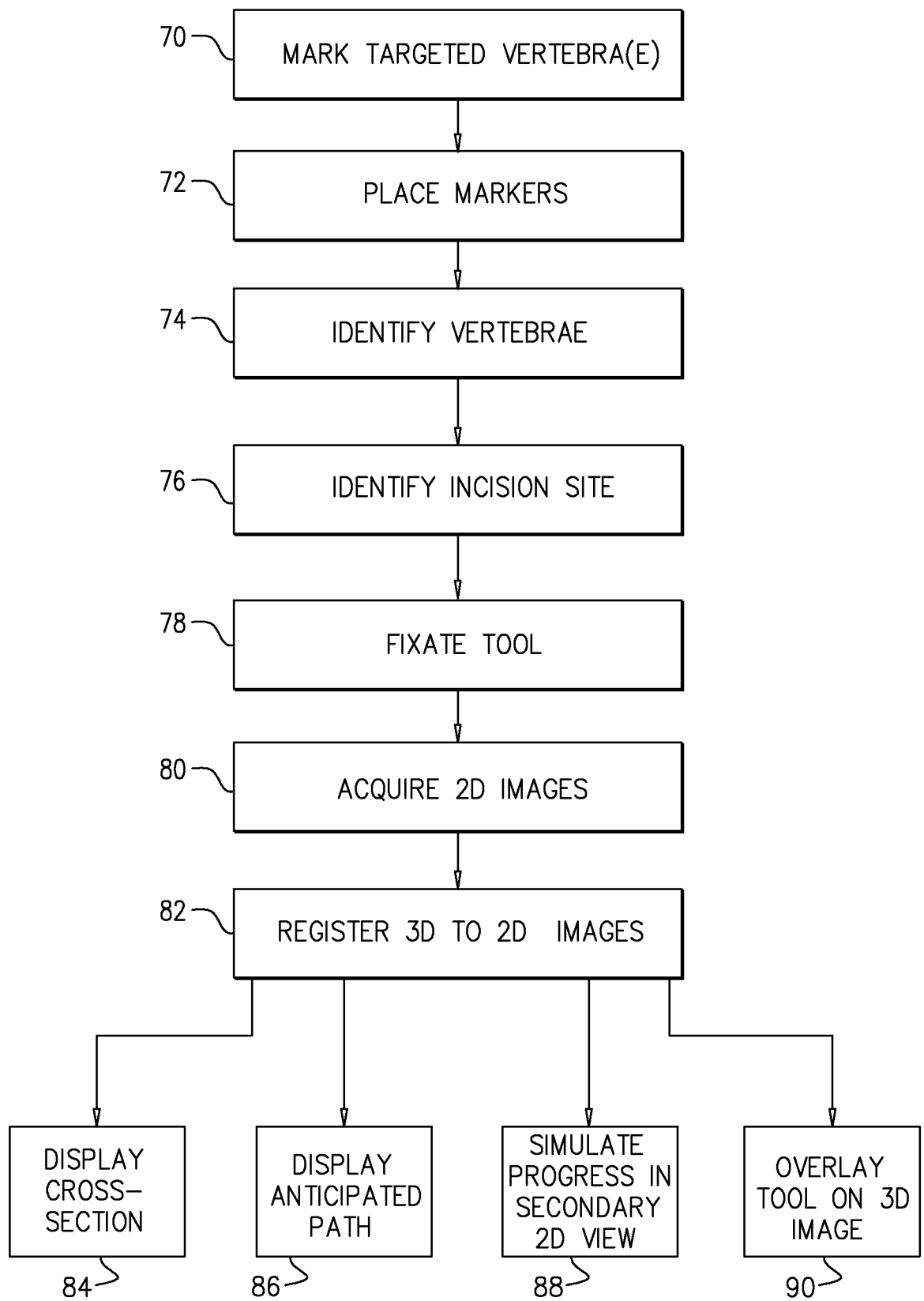
FIG. 7 is a flowchart showing steps that are typically performed using the system of FIG. 1B, in accordance with some applications of the present invention.

Reference is now made to FIG. 7, which is a flowchart showing steps that are typically performed using system 20, in accordance with some applications of the present invention. It is noted that some of the steps shown in FIG. 7 are optional, and some of the steps may be performed in a different order to that shown in FIG. 7. In a first step 70, targeted vertebra(e) are marked by an operator with respect to 3D image data (e.g., a 3D image, a 2D cross-section derived from 3D image data, and/or a 2D projection image derived from 3D image data) of the subject's spine. For some applications, in a second step 72, sets 50 of markers 52 are placed on the subject, underneath the subject, on the surgical table, or above the surgical table in a vicinity of the subject. For some applications, step 72 is performed prior to step 70. Typically, in a third step 74, vertebrae of the spine are identified in order to verify that the procedure is being performed with respect to the correct vertebra (a step which is known as "level verification"), using radiographic images of the spine and the markers to facilitate the identification. In a fourth step 76, an incision site (in the case of minimally-invasive surgery) or a tool entry point (in the case of open surgery) is determined. In a fifth step 78, the first tool in the sequence of tools (which is typically a needle, e.g., a Jamshidi™ needle) is typically inserted into the subject (e.g., in the subject's back), and is slightly fixated in the vertebra. In a sixth step 80, two or more 2D radiographic images are acquired from respective views that typically differ by at least 10 degrees (and further typically by 30 degrees or more), and one of which is typically from the direction of insertion of the tool. Typically, generally-AP and generally-lateral images are acquired. Alternatively or additionally, images from different views are acquired. In a seventh step 82, computer processor 22 of system 20 typically registers the 3D image data to the 2D images.

Subsequent to the registration of the 3D image data to the 2D images additional features of system 20 as described in detail hereinbelow may be applied by computer processor 22. For example, in step 84, the computer processor drives display 30 to display a cross-section derived from the 3D image data at a current location of the tip of a tool as identified from a 2D image, and, optionally, to show a vertical line on the cross-sectional image indicating a line within the cross-sectional image somewhere along which the tip of the tool is currently disposed.

It is noted, that, as described in further detail hereinbelow, for some applications, in order to perform step 84, the computer processor need acquire one or more 2D x-ray images of a tool at a first location inside the vertebra from only a single x-ray image view, and the one or more 2D x-ray images are registered to the 3D image data by generating a plurality of 2D projections from the 3D image data, and identifying a 2D projection that matches the 2D x-ray images of the vertebra. In response to registering the one or more 2D x-ray images acquired from the single x-ray image view to the 3D image data, the computer processor drives a display to display a cross-section derived from the 3D image data at a the first location of a tip of the tool, as identified from the one or more 2D x-ray images, and optionally to show a vertical line on the cross-sectional image indicating a line within the cross-sectional image somewhere along which the first location of the tip of the tool is disposed. Typically, when the tip of the tool is disposed at an additional location with respect to the vertebra, further 2D x-ray images of the tool at the additional location are acquired from the same single x-ray image view, or a different single x-ray image view, and the above-described steps are repeated. Typically, for each location of the tip of the tool to which the above-described technique is applied, 2D x-ray images need only be acquired from a single x-ray image view, which may stay the same for the respective locations of the tip of the tool, or may differ for respective locations of the tip of the tool. Typically, two or more 2D x-rays are acquired from respective views, and the 3D image data and 2D x-ray images are typically registered to the 3D image data (and to each other) by identifying a corresponding number of 2D projections of the 3D image data that match respective 2D x-ray images. In step 86, the computer processor drives display 30 to display the anticipated (i.e., extrapolated) path of the tool with reference to a target location and/or with reference to a desired insertion vector. In step 88, the computer processor simulates tool progress within a secondary 2D imaging view, based upon observed progress of the tool in a primary 2D imaging view. In step 90, the computer processor overlays an image of the tool, a representation thereof, and/or a representation of the tool path upon the 3D image data (e.g., a 3D image, a 2D cross-section derived from 3D image data, and/or a 2D projection image derived from 3D image data), the location of the tool or tool path having been derived from current 2D images.

Reference is now made to FIG. 8A, which shows a vertebra 91 designated upon a coronal cross-sectional image 92 and upon a sagittal cross-sectional image 94 of a subject's spine, the cross-sectional images being derived from 3D image data, in accordance with some applications of the present invention. As described hereinabove with reference to step 70 of FIG. 7, typically prior to the subject being placed into the operating room, or while the subject is in the operating room but before an intervention has commenced, an operator marks the targeted vertebra(e) with respect to the 3D image data (e.g., a 3D image, a 2D cross-section derived from 3D image data, and/or a 2D projection image derived from 3D image data). For some applications, in response to the operator marking one vertebra, the computer processor designates additional vertebra(e). For some applications, the operator marks any one of, or any combination of, the following with respect to the 3D image data: a specific target within the vertebra (such as a fracture, a tumor, etc.), desired approach directions/vectors for tool insertion, and/or desired placement locations of implants (such as pedicle screws). For some applications, the operator marks the targeted vertebra with respect to a 2D x-ray image that has a sufficiently large field of view to encompass an identifiable portion of the anatomy (e.g., the sacrum) and the targeted vertebra(e). For some applications, more than one targeted vertebra is marked, and for some applications, two or more vertebra(e) that are not adjacent to one another are marked.

For some applications, the computer processor automatically counts the number of vertebrae on the image from an identifiable anatomical reference (e.g., the sacrum) to the marked target vertebra(e). It is then known that the targeted vertebra(e) is vertebra N from the identifiable anatomical reference (even if the anatomical labels of the vertebra(e) are not known). For some applications, the vertebra(e) are counted automatically using image-processing techniques. For example, the image-processing techniques may include shape recognition of anatomical features (of vertebrae as a whole, of traverse processes, and/or of spinous processes, etc.). Or, the image-processing techniques may include outer edge line detection of spine (in a 2D image of the spine) and then counting the number of bulges along the spine (each bulge corresponding to a vertebra). For some applications, the image-processing techniques include techniques described in US 2010-0161022 to Tolkowsky, which is incorporated herein by reference.

Referring to step 72 of FIG. 7 in more detail, for some applications, in which a procedure is performed on a given vertebra of the subject's spine, one or more sets 50 of radiopaque markers 52 are placed upon or near the subject, such that markers that are placed at respective locations with respect to the subject are identifiable, e.g., as shown in FIGS. 5A-E and 6A-B. For example, as shown in FIGS. 6A and 6B respective radiopaque alphanumeric characters are disposed at respective locations. For some applications, markers placed at respective locations are identifiable based upon other features, e.g., based upon the dispositions of the markers relative to other markers. Using a radiographic imaging device (e.g., C-arm 34), a plurality of radiographic images of the set of radiopaque markers are acquired, respective images being of respective locations along at least a portion of the subject's spine and each of the images including at least some of the radiopaque markers. Using computer processor 22, locations of the radiopaque markers within the radiographic images are identified, by means of image processing. At least some of the radiographic images are combined with respect to one another based upon the identified locations of the radiopaque markers within the radiographic images. Typically, such combination of images is similar to stitching of images. However, the images are typically not precisely stitched such as to stitch portions of the subject's anatomy in adjacent images to one another. Rather, the images are combined with sufficient accuracy to be able to determine a location of the given vertebra within the combined radiographic images.

For some applications, based upon the combined radiographic images, the computer processor automatically determines a location of the given vertebra (e.g., the previously-marked targeted vertebra) within the combined radiographic images. For some applications, the computer processor automatically determines location of the given vertebra within the combined radiographic images by counting the number of vertebrae on said image from an identifiable anatomical reference (e.g., the sacrum). For some applications, the counting is performed until the aforementioned N. For some applications, the counting is performed until a value that is defined relative to the aforementioned N. For some applications, the vertebra(e) are counted automatically using image-processing techniques. For example, the image-processing techniques may include shape recognition of anatomical features (of vertebrae as a whole, of traverse processes, and/or of spinous processes, etc.). Or, the image-processing techniques may include outer edge line detection of spine (in a 2D image of the spine) and then counting the number of bulges along the spine (each bulge corresponding to a vertebra). For some applications, the image-processing techniques include techniques described in US 2010-0161022 to Tolkowsky, which is incorporated herein by reference. For some applications, the computer processor facilitates manual determination of the location of the given vertebra within the combined radiographic images by displaying the combined radiographic images.

Based upon the location of the given vertebra within the combined radiographic images, a location of the given vertebra in relation to the set of radiopaque markers that is placed on or near the subject is determined, as described in further detail hereinbelow.

For some applications, a similar technique to that described hereinabove with respect to vertebrae is performed with respect to a subject's ribs. For example, a set of radiopaque markers is placed upon or near the subject, such that markers that are placed at respective locations with respect to the subject are identifiable. Using a radiographic imaging device (e.g., C-arm 34), a plurality of radiographic images of the set of radiopaque markers are acquired, respective images being of respective locations along at least a portion of the subject's ribcage and each of the images including at least some of the radiopaque markers. Using the computer processor, locations of the radiopaque markers within the radiographic images are identified, by means of image processing, and at least some of the radiographic images are combined with respect to one another based upon the identified locations of the radiopaque markers within the radiographic images.

For some applications, based upon the combined radiographic image, the computer processor automatically determines a location of the given rib (e.g., a targeted rib previously marked and counted within CT image data, MRI image data, and/or an x-ray image with a sufficiently large field of view) within the combined radiographic images. For some applications, the computer processor automatically determines location of the given rib within the combined radiographic images by counting the number of ribs on the image from an identifiable anatomical reference. For some applications, the ribs are counted automatically using image-processing techniques. For example, the image-processing techniques may include shape recognition of ribs. For some applications, the image-processing techniques include techniques described in US 2010-0161022 to Tolkowsky, which is incorporated herein by reference. For some applications, the computer processor facilitates manual determination of the location of the given rib within the combined radiographic images by displaying the combined radiographic images. Based upon the location of the given rib within the combined radiographic images, a location of the given rib is determined in relation to the set of radiopaque markers that is placed on or near the subject.

It is noted that in the absence of sets 50 of markers 52, the typical methodology for determining the location of a given vertebra includes acquiring a series of x-rays along the patient's spine from the sacrum, and sticking radiopaque needles into the subject in order to match the x-rays to one another. Typically, in each x-ray spinal image only 3-4 vertebrae are within the field of view, and multiple, overlapping images must be acquired, such as to enable human counting of vertebra using the overlapping images. This technique may involve switching back and forth between AP and lateral x-ray images. This method sometimes results in wrong-level surgery, as described, for example, in "Wrong-Site Spine Surgery: An Underreported Problem? AAOS Now," American Association of Orthopedic Surgeons, March 2010.

Reference is now made to FIG. 8B which shows an example of a 3D CT image 95 of a subject's spine displayed alongside a combined radiographic image 96 of the subject's spine, in accordance with some applications of the present invention. In accordance with some applications of the present invention, set 50 of markers 52 is placed upon or near the subject, such that the bottom of the set of markers is disposed over, or in the vicinity of, the sacrum. A sequence of x-ray images from generally the same view as one another are acquired along the spine, typically, but not necessarily, with some overlap between adjacent images. The sequence of x-ray images is typically acquired from a generally-AP view, but may also be acquired from a different view, such as a generally-lateral view. Using computer processor 22, locations of the radiopaque markers within the radiographic images are identified, by means of image processing. At least some of the radiographic images are combined with respect to one another based upon the identified locations of the radiopaque markers within the radiographic images. For example, combined radiographic image 96 is generated by combining (a) a first x-ray image 97 acquired from a generally-AP view and which starts at the subject's sacrum and which includes markers H-E of the right marker set and markers 8-5 of the left marker set with (b) second x-ray image 98 acquired from a generally similar view to the first view (but one which is not exactly the same) and which includes markers E-B of the right marker set and markers 5-2 of the left marker set.

(It is noted that in FIG. 8B the alphanumeric markers appear as white in the image. In general, the markers may appear as generally white or generally black, depending on (a) the contrast settings of the image (e.g., do radiopaque portions appear as white on a black background, or vice versa), and (b) whether the markers are themselves radiopaque, or the markers constitute cut-outs from a radiopaque backing material, as is the case, in accordance with some applications of the present invention.)

Typically, the combination of images is similar to stitching of images. However, the images are typically not precisely stitched such as to stitch portions of the subject's anatomy in adjacent images to one another. Rather, the images are combined with sufficient accuracy to facilitate counting vertebrae along the spine within the combined image. The physical location of a given vertebra is then known by virtue of it being adjacent to, or in the vicinity of, or observable in the x-ray images relative to, a given one of the identifiable markers. It is noted that in order to combine the radiographic images to one another, there is typically no need to acquire each of the images from an exact view (e.g., an exact AP or an exact lateral view), or for there to be exact replication of a given reference point among consecutive images. Rather, generally maintaining a given imaging direction, and having at least some of the markers generally visible in the images is typically sufficient.

As described hereinabove, for some applications, the computer processor automatically counts (and, for some applications, labels, e.g., anatomically labels, and/or numerically labels) vertebrae within the combined radiographic images in order to determine the location of the previously-marked target vertebra(e), or other vertebra(e) relative to the previously marked vertebra. Alternatively, the computer processor drives the display to display the combined radiographic images such as to facilitate determination of the location of the previously-marked target vertebra(e)

by an operator. The operator is able to count to the vertebra within the combined radiographic images, to determine, within the combined images, which of the radiopaque markers are adjacent to or in the vicinity of the vertebra, and to then physically locate the vertebra within the subject by locating the corresponding physical markers.

Figure 8C:
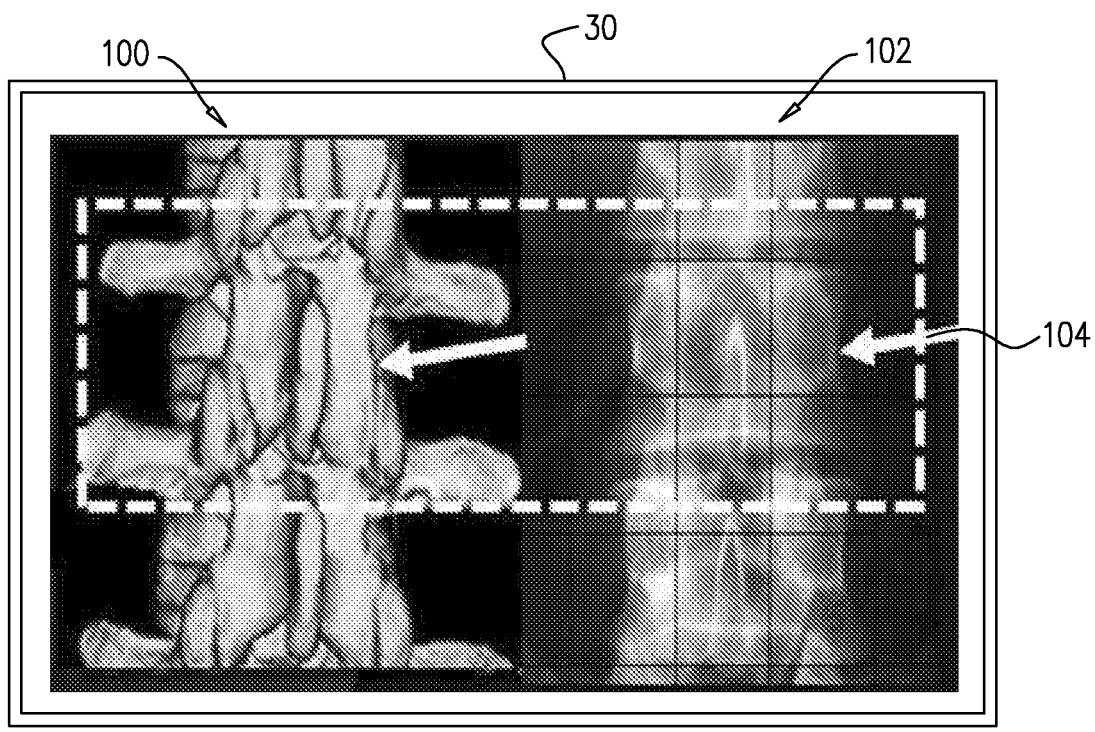
FIG. 8C shows the designated vertebra indicated on a 3D CT image and on a 2D x-ray image, the CT image and x-ray image being displayed alongside one another, in accordance with some applications of the present invention.

Reference is now made to FIG. 8C, which shows an example of a 3D CT image 100 of the subject's spine displayed alongside a 2D radiographic image 102 of the subject's spine, in accordance with some applications of the present invention. As shown, markers 52 appear on the combined radiographic image. As shown, vertebra 91, which was identified by an operator with respect to the 3D image data (as described hereinabove with reference to FIG. 8A), has been identified within the 2D radiographic image using the above-described techniques, and is denoted by cursor 104.

For some applications, based upon counting and/or labeling of the vertebrae in the combined radiographic image, computer processor 22 of system 20 counts and/or labels vertebrae within the 3D image data (e.g., a 3D image, a 2D cross-section derived from 3D image data, and/or a 2D projection image derived from 3D image data). For some applications, the computer processor drives the display to display the labeled vertebrae while respective corresponding 2D images are being acquired and displayed. Alternatively or additionally, the computer processor drives the display to display the labeled vertebrae when the combined radiographic image has finished being generated and/or displayed. It is noted that, typically, the computer processor counts, labels, and/or identifies vertebrae on the 3D image data and on the 2D radiographic images without needing to determine relative scales of the 3D image data and 2D images. Rather, it is sufficient for the computer processor to be able to identify individual vertebrae at a level that is sufficient to perform the counting, labeling, and/or identification of vertebrae.

It is noted that the above-described identification of vertebrae that is facilitated by markers 52 is not limited to being performed by the computer processor at the start of an intervention. Rather, the computer processor may perform similar steps at subsequent stages of the procedure. Typically, it is not necessary for the computer processor to repeat the whole series of steps at the subsequent stages, since the computer processor utilizes knowledge of an already-identified vertebra, in order to identify additional vertebrae. For example, after identifying and then performing a procedure with respect to a first vertebra, the computer processor may utilize the combined radiographic image to derive a location of a further target vertebra (which may be separated from the first vertebra by a gap), based upon the already-identified first vertebra. For some applications, in order to derive the location of a further target vertebra, the computer processor first extends the combined radiographic image (typically, using the markers in order to do so, in accordance with the techniques described hereinabove).

For some applications, the operator labels a single vertebra (or in some applications, a plurality of vertebra) within the 3D image data of the spine. Based upon the labelling of the vertebra(e) the computer processor automatically labels other vertebrae within the 3D image data, based upon the known anatomical sequence of vertebrae along the spine. For some applications, based upon the labelling of the one or more vertebrae within the 3D image data, the computer processor labels (e.g., anatomically labels, and/or numerically labels) the vertebrae within the combined radiographic image. In this manner, a spinal roadmap is created within the 3D image data (e.g., a 3D image, a 2D cross-section derived from 3D image data, and/or a 2D projection image derived from 3D image data) and within the combined radiographic images. For some applications, the spinal roadmap is generated upon an image that is a fused combination of the 3D image data and the 2D radiographic images. For some applications, the spinal roadmap is automatically updated intraprocedurally. For example, in response to detecting a tool within a given vertebra within a 2D x-ray image, the 3D spinal roadmap may be updated to show the tool within the vertebra, using the coregistration techniques described in detail hereinbelow.

In general, the scope of the present invention includes acquiring imaging data of the subject's spine, using an imaging device (e.g., a 2D imaging device, and/or a 3D imaging device). During a procedure in which interventions are performed with respect to at least first and second vertebrae of a subject's spine, a spinal roadmap image of at least a portion of the spine that contains the first and second vertebra is generated by computer processor 22 and displayed upon display 30. The computer processor typically automatically labels vertebra within the spinal roadmap image. For some applications, the computer processor determines that an intervention has been performed with respect to the first vertebra (e.g., a tool has been inserted and/or implanted in the first vertebra), such that an appearance of the first vertebra has changed. In response thereto, the computer processor automatically updates the spinal roadmap to reflect the change in the appearance of the first vertebra, such that the updated spinal roadmap is displayed while the intervention is performed with respect to the second vertebra.

Figure 9:
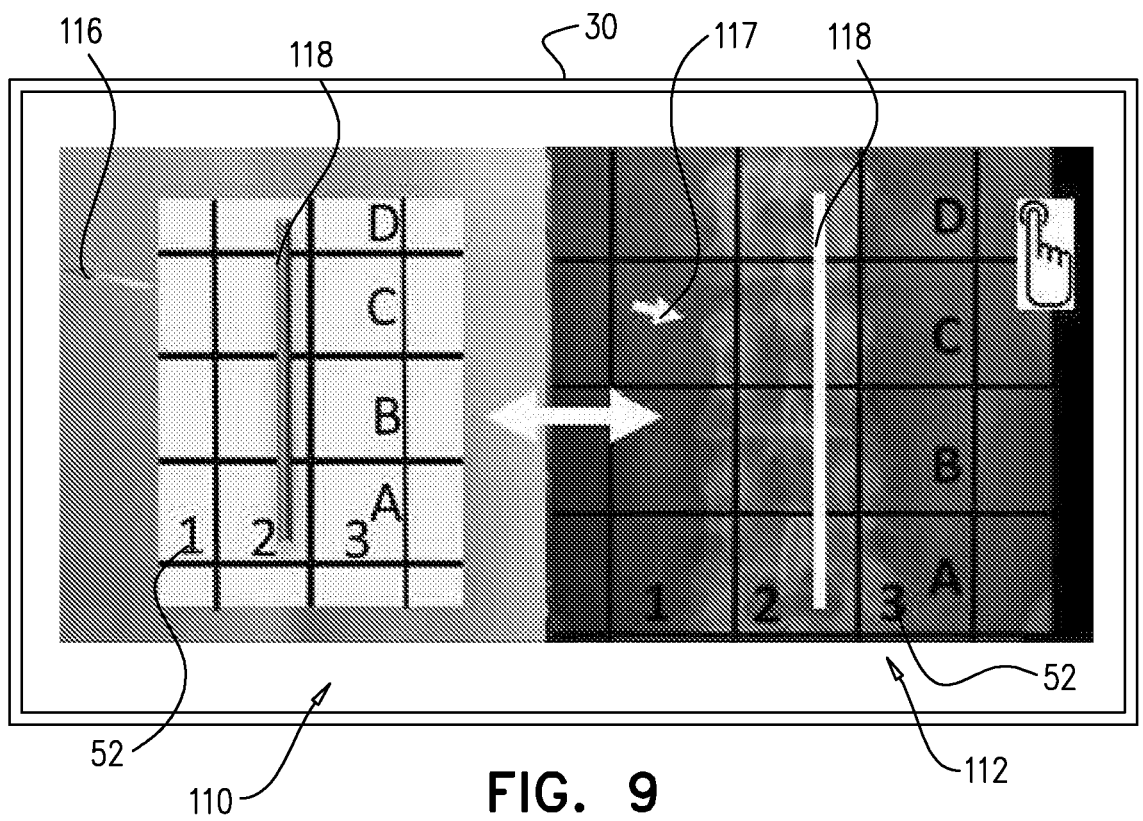
FIG. 9 shows an example of an optical image displayed alongside a 2D radiographic image, in accordance with some applications of the present invention.

Reference is now made to FIG. 9, which shows an example of an optical image 110 displayed alongside a 2D radiographic (e.g., x-ray) image 112, in accordance with some applications of the present invention. As described with reference to step 76 of FIG. 7, subsequent to identifying a target vertebra along the subject's spine, typically, the operator determines a desired site for an incision (in the case of minimally-invasive surgery) or tool insertion (in the case of open surgery). For some applications, in order to facilitate the determination of the incision site or tool insertion site, an optical camera 114 is disposed within the operating room such that the optical camera has a generally similar viewing angle to that of the 2D radiographic imaging device. For example, the camera may be disposed on x-ray C-arm 34, as shown in FIG. 1. Alternatively or additionally, the camera may be disposed on a separate arm, may be handheld, may be the back camera of a display such as a tablet or mini-tablet device, and/or may be held by another member of the operating room staff. For some applications, the camera is placed on the surgeon's head. Typically, for such applications, the surgeon uses a head-mounted display.

For some applications, a 2D radiographic image 112 of a portion of the subject's body is acquired in a radiographic imaging modality, using the 2D radiographic imaging device (e.g., C-arm 34), and an optical image 110 of the subject's body is acquired in optical imaging modality, using optical camera 114 (shown in FIG. 1). Computer processor 22 of system 20 identifies radiopaque markers (e.g., markers 52) in the radiographic image and in the optical image, by means of image processing. By way of example, in FIG. 9, radiopaque gridlines (as shown in FIG. 5B), and alphanumeric radiopaque markers associated with the radiopaque gridlines (also as shown in FIG. 5B), are visible in both the radiographic and the optical image. Based upon the identification of the radiopaque markers in the radiographic image and in the optical image, the computer processor bidirectionally maps the radiographic image and the optical image with respect to one another. It is noted that acquisition of the radiographic image and the optical image from generally-similar views (but not necessarily identical views) is typically sufficient to facilitate the bidirectional mapping of the images to one another, by virtue of the radiopaque markers that are visible in both of the images.

As shown in FIG. 9, for some applications, the computer processor drives display 30 to display the radiographic image and the optical image separately from one another, upon one or more displays. Subsequently, in response to receiving an input indicating a location in a first one of the radiographic and the optical images, the computer processor generates an output indicating the location in the other one of the radiographic and the optical images. For example, in response to a line or a point being marked on 2D x-ray image 112, the computer processor indicates a corresponding lines or points overlaid on the optical image 110. Similarly, in response to a line or a point being marked on optical image 110, the computer processor indicates a corresponding lines or points overlaid on the 2D x-ray image 112. Further similarly, in response to a line or a point being marked on, or an object such as a k-wire or incision knife laid upon, the subject's body (e.g., back in the case of a planned dorsal tool insertion) as seen in a then-current optical image 110, the computer processor identifies such line, point or object (or applicable portion thereof) and indicates a corresponding lines or points overlaid on the 2D x-ray image 112. For some applications, a line or point is drawn on the subject's body (e.g., on the subject's back in the case of a planned dorsal tool insertion) using radiopaque ink.

Traditionally, in order to determine the location of an incision site, a radiopaque wire is placed on the subject's back at a series of locations, and the x-rays are taken of the wire at the locations, until the incision site is determined. Subsequently, a knife is placed at the determined incision site, and a final x-ray image is acquired for verification. By contrast, in accordance with the technique described herein, initially a single x-ray image may be acquired and bidirectionally mapped to the optical image. Subsequently the wire is placed at a location, and the corresponding location of the wire with respect to the x-ray image can be observed (using the bidirectional mapping) without requiring the acquisition of a new x-ray image. Similarly, when an incision knife is placed at a location, the corresponding location of an applicable portion of the knife (typically, its distal tip) with respect to the x-ray image can be observed (using the bidirectional mapping) without requiring the acquisition of a new x-ray image. Alternatively or additionally, a line can be drawn on the x-ray image (e.g., a vertical line that passes along the vertebral centers, anatomically along the spinous processes of the vertebrae) and the corresponding line can be observed in the optical image overlaid on the patient's back.

For some applications, a surgeon places a radiopaque knife 116 (or another radiopaque tool or object) at a prospective incision site (and/or places a tool at a prospective tool insertion location) and verifies the location of the incision site (and/or tool insertion location) by observing the location of the tip of the knife (or portion of another tool) with respect to the x-ray (e.g., via cursor 117), by means of the bi-directional mapping between the optical image and the x-ray image. For some applications, the functionalities described hereinabove with reference to FIG. 9, and/or with reference other figures, are performed using markers (which are typically sterile), other than markers 52. For example, a radiopaque shaft 118, ruler, radiopaque notches, and/or radiopaque ink may be used.

Reference is now made to FIG. 10, which shows an example of a 2D radiographic (e.g., x-ray) image 120 displayed alongside a cross-sectional image 122 of a subject's vertebra that is derived from a 3D image data of the vertebra, in accordance with some applications of the present invention. For some applications, even prior to registering the 2D images to the 3D image data (as described hereinbelow), the following steps are performed. X-ray image 120 of a given view the subject's spine (e.g., AP, as shown) is acquired. A point is indicated upon the image, e.g., the point indicated by cursor 124 in FIG. 10. Computer processor 22 of system 20 automatically identifies the end plates of the vertebra, and calculates the relative distance of indicated point from end plates. (It is noted that the computer processor typically does not calculate absolute distances in order to perform this function.) From the 3D (e.g., CT) image of the same vertebra, the computer processor generates and displays a cross-section of a given plane (which is typically axial) at the indicated location (e.g. image 122). For some applications, upon the cross-section, the computer processor drives the display to show a line 126 (e.g., a vertical line) within the cross-section, the line indicating that the indicated location falls somewhere along the line. For some applications, the line is drawn vertically upon an axial cross-section of the vertebra as shown. The computer processor determines where to place the line according to distance of the indicated point from left and right edges of the vertebra, and/or according to the position of the indicated point relative to visible features (e.g., spinous process, traverse processes, pedicles) in the x-ray image. Typically, the cross-sectional image with the line, and coupled with the surgeon's tactile feel of how far from the vertebra the skin is (and/or deriving such information from a 3D image), assists the surgeon in calculating the desired insertion angle of a tool.

Referring again to step 78 of FIG. 7, the first tool in the sequence of tools (which is typically a needle, e.g., a Jamshidi™ needle) is inserted into the subject (e.g., in the subject's back), and is slightly fixated in the vertebra. Subsequently, in step 80, two or more 2D radiographic images are acquired from respective views that typically differ by at least 10 degrees (e.g., 30 degrees or more), and one of which is typically from the direction of insertion of the tool. Common combinations of such views include AP and left or right lateral, AP with left or right oblique, left oblique with left lateral, and right oblique with right lateral. It is noted that, as described in further detail hereinbelow, with reference to FIG. 15A, for some applications, 2D radiographic images of the tool and the vertebra are acquired from only a single x-ray image view.

Reference is now made to FIGS. 11A and 11B, which show examples of respectively AP and lateral x-ray images of a Jamshidi™ needle 36 being inserted into a subject's spine, in accordance with some applications of the present invention. As shown, sets 50 of markers 52 typically appear at least in the AP image.

Figure 12A:
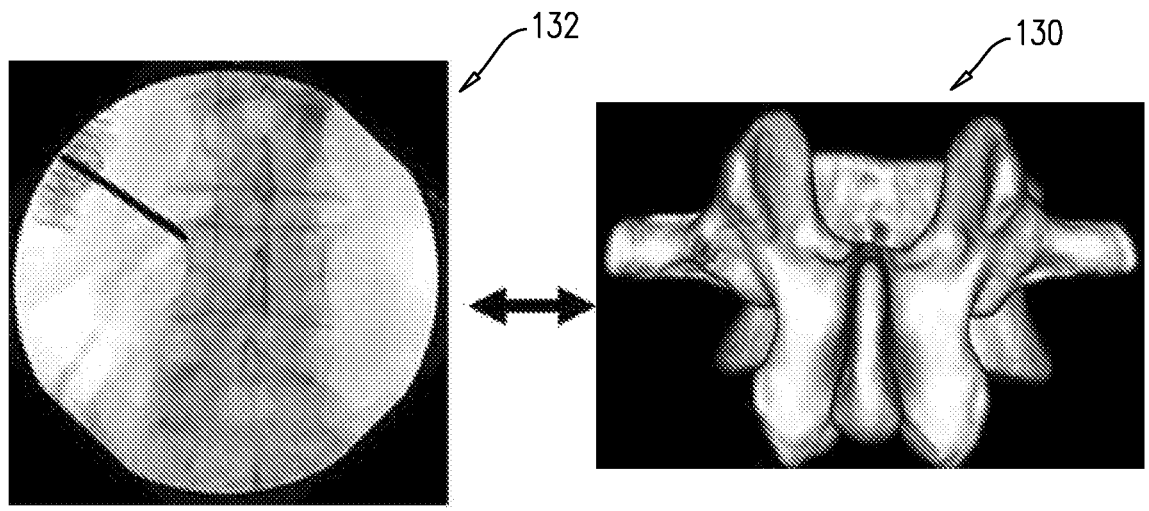
FIGS. 12A and 12B show examples of correspondence between respective views of a 3D image a vertebra, with corresponding respective first and second x-ray images of the vertebra, in accordance with some applications of the present invention.
Figure 12B:
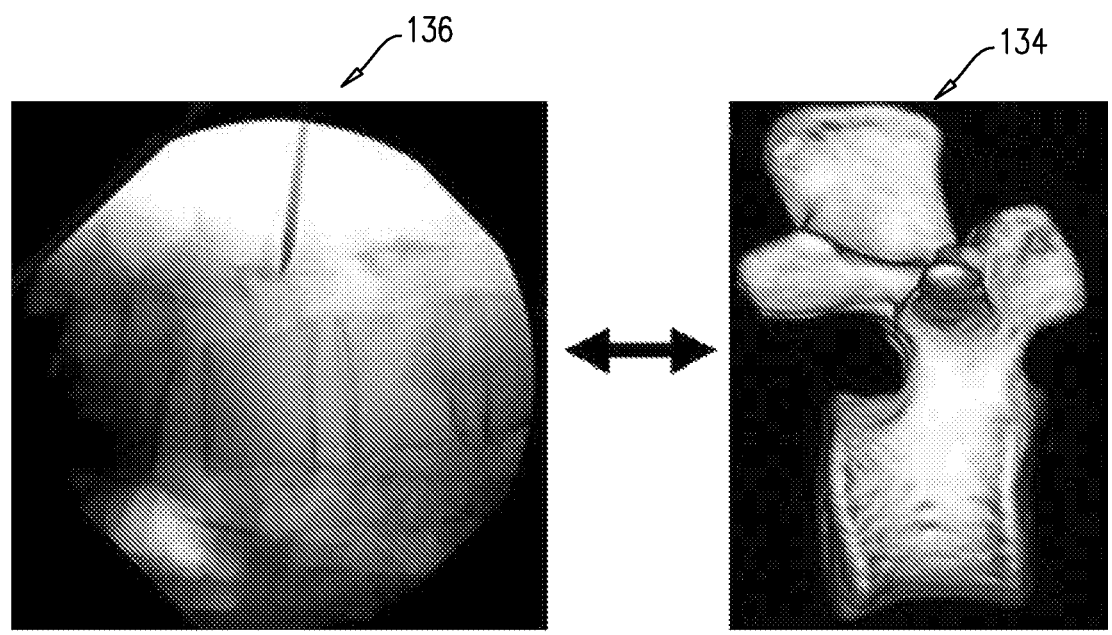

Reference is now made to FIGS. 12A and 12B, which show examples of correspondence between views of a 3D image of a vertebra, with, respectively, first and second 2D x-ray images 132 and 136 of the vertebra, in accordance with some applications of the present invention. In FIG. 12A the correspondence between a first view 130 of a 3D image of a vertebra with an AP x-ray image of the vertebra is shown, and in FIG. 12B the correspondence between a second view 134 of a 3D image of a vertebra with a lateral x-ray image of the vertebra is shown.

For some applications, subsequent to the fixation of the tool in the subject's vertebra, the 3D image data and 2D images are registered to each other, in accordance with step 82 of FIG. 7. However, it is noted that the registration of the 3D image data and the 2D images to each other may be performed even in the absence of a tool within the images, in accordance with the techniques described hereinbelow. Typically, the 3D image data and 2D images are registered to each other by generating a plurality of 2D projections from the 3D image data, and identifying respective first and second 2D projections that match the first and second 2D x-ray images of the vertebra, as described in further detail hereinbelow. (For some applications, 2D x-ray images from more than two 2D x-ray image views are acquired and the 3D image data and 2D x-ray images are registered to each other by identifying a corresponding number of 2D projections of the 3D image data that match respective 2D x-ray images.) Typically, the first and second 2D x-ray images of the vertebra are acquired using an x-ray imaging device that is unregistered with respect to the subject's body, by (a) acquiring a first 2D x-ray image of the vertebra (and at least a portion of the tool) from a first view, while the x-ray imaging device is disposed at a first pose with respect to the subject's body, (b) moving the x-ray imaging device to a second pose with respect to the subject's body, and (c) while the x-ray imaging device is at the second pose, acquiring a second 2D x-ray image of at least the portion of the tool and the skeletal portion from a second view.

For some applications, the 3D imaging that is used is CT imaging, and the following explanation of the registration of the 3D image data to the 2D images will focus on CT images. However, the scope of the present invention includes applying the techniques describe herein to other 3D imaging modalities, such as MRI and 3D x-ray, mutatis mutandis.

X-ray imaging and CT imaging both apply ionizing radiation to image an object such as a body portion or organ. 2D x-ray imaging generates a projection image of the imaged object, while a CT scan makes use of computer-processed combinations of many x-ray images taken from different angles to produce cross-sectional images (virtual "slices") of the scanned object, allowing the user to see inside the object without cutting. Digital geometry is used to generate a 3D image of the inside of the object from a large series of 2D images.

Reference is now made to FIGS. 13A, 13B, and 13C, which demonstrate the relationship between a 3D image of an object (which in the example shown in FIG. 13A is a cone) and side-to-side (FIG. 13B) and bottom-to-top (FIG. 13C) 2D images of the object, such relationship being utilized, in accordance with some applications of the present invention. As shown, for the example of the cone, the bottom-to-top 2D image (which is analogous to an AP x-ray image of an object acquired by C-arm 34, as schematically indicated in FIG. 13C) is a circle, while the side-to-side image (which is analogous to a lateral x-ray image of an object, acquired by C-arm 34, as schematically indicated in FIG. 13C) is a triangle. It follows that, in the example shown, if the circle and the triangle can be registered in 3D space to the cone, then they also become registered to one another in that 3D space. Therefore, for some applications, 2D x-ray images of a vertebra from respective views are registered to one another and to 3D image data of the vertebra by generating a plurality of 2D projections from the 3D image data, and identifying respective first and second 2D projections that match the 2D x-ray images of the vertebra.

In the case of 3D CT images, the derived 2D projections are known as Digitally Reconstructed Radiographs (DRRs). If one considers 3D CT data and a 2D x-ray image of the same vertebra, then a simulated x-ray camera position (i.e., viewing angle and viewing distance) can be virtually positioned anywhere in space relative to a 3D image of the vertebra, and the corresponding DRR that this simulated camera view would generate can be determined. At a given simulated x-ray camera position relative to the 3D image of the vertebra, the corresponding DRR that this simulated camera view would generate is the same as the 2D x-ray image. For the purposes of the present application, such a DRR is said to match an x-ray image of the vertebra. Typically, 2D x-ray images of a vertebra from respective views are registered to one another and to 3D image data of the vertebra by generating a plurality of DRRs from 3D CT image data, and identifying respective first and second DRRs (i.e., 2D projections) that match the 2D x-ray images of the vertebra. By identifying respective DRRs that match two or more x-ray images acquired from respective views, the x-ray images are registered to the 3D image data, and, in turn, the x-ray images are registered to one another via their registration to the 3D image data.

For some applications, in order to register the 2D images to the 3D image data, additional registration techniques are used in combination with the techniques described herein. For example, intensity based methods, feature based methods, similarity measures, transformations, spatial domains, frequency domains, etc., may be used to perform the registration.

Typically, by registering the x-ray images to the 3D image data using the above-described technique, the 3D image data and 2D x-ray images are brought into a common reference frame to which they are all aligned and scaled. It is noted that the registration does not require tracking the subject's body or a portion thereof (e.g., by fixating one or more location sensors, such as an IR light, an IR reflector, an optical sensor, or a magnetic or electromagnetic sensor, to the body or body portion, and tracking the location sensors).

Typically, between preprocedural 3D imaging (e.g., 3D imaging performed prior to entering the operating room, or prior to performing a given intervention) and intraprocedural 2D imaging, the position and/or orientation of a vertebra relative to the subject's body and to neighboring vertebrae is likely to change. For example, this may be due to the patient lying on his/her back in preprocedural imaging but on the stomach or on the side for intraprocedural imaging, or the patient's back being straight in preprocedural imaging, but being folded (e.g., on a Wilson frame) in intraprocedural imaging. In addition, in some cases, due to anesthesia the position of the spine changes (e.g. sinks), and once tools are inserted into a vertebra, that may also change its positioning relative to neighboring vertebrae. However, since a vertebra is a piece of bone, its shape typically does not change between the preprocedural 3D imaging and the intraprocedural 2D imaging. Therefore, registration of the 3D image data to the 2D images is typically performed with respect to individual vertebrae. For some applications, registration of the 3D image data to the 2D images is performed on a per-vertebra basis even in cases in which segmentation of a vertebra in the 3D image data leaves some elements, such as portions of the spinous processes of neighboring vertebrae, within the segmented image of the vertebra. In addition, for some applications, registration of the 3D image data to the 2D images is performed with respect to a spinal segment comprising several vertebrae. For example, registration of 3D image data to the 2D images may be performed with respect to a spinal segment in cases in which the 3D image data were acquired when the subject was already in the operating room and positioned upon the surgical table for the intervention.

As described hereinabove, typically, during a planning stage, an operator indicates a target vertebra within the 3D image data of the spine or a portion thereof (e.g., as described hereinabove with reference to FIG. 8A). For some applications, the computer processor automatically identifies the target vertebra in the x-ray images, by means of image processing, e.g., using the techniques described hereinabove. For some applications, the registration of the 3D image data to the 2D images is performed with respect to an individual vertebra that is automatically identified, by the computer processor, as corresponding to a target vertebra as indicated by the operator with respect to the 3D image data of the spine or a portion thereof (e.g., as described hereinabove with reference to FIGS. 8A-C).

Typically, and since the registration is performed with respect to an individual vertebra, the registration is not affected by motion of the vertebra that occurs between the acquisition of the two x-ray images (e.g., due to movement of the subject upon the surgical table, motion due to respiration, etc.), since both motion of the C-arm and of the vertebra may be assumed to be rigid transformations (and thus, if both motions occur in between the acquisition of the two x-ray images, a chaining of two rigid transformations may be assumed).

For some applications, motion of the patient is detected in order to serve as an input for some functionalities of computer processor 22. For example, a motion detection sensor 56 may be coupled to a set 50 of markers 52 (e.g., by being coupled to drape 53, as shown, by way of example, in FIG. 5A), and/or to a portion of the subject's body. It is noted that the motion detection sensor is typically not a location sensor, the motion of which is tracked by a tracker, or a tracker that is configured to track the motion of a location sensor situated elsewhere. Typically, the motion detection sensor detects that a portion of the subject's body has undergone motion in a standalone manner (i.e., the motion detection sensor detects that its motion has occurred relative to a prior position of itself (as opposed to detecting that its motion has occurred relative to an external element)). Furthermore, typically, the motion detection sensor is configured to detect that motion has occurred, but not necessarily that a specific motion has occurred. For example, the motion detection sensor may be configured to detect motion that is greater than a threshold. For some applications, an accelerometer is used. For example, the accelerometer could be configured to detect motion that is abrupt. In response to detecting that motion has occurred, the motion detection sensor may communicate a signal to the computer processor. For some applications, in response to receiving an input indicating that the subject has undergone motion, the computer processor generates an alert, and/or generates an output indicating that one or more images should be reacquired. Alternatively or additionally, the motion detection sensor is independently powered and is configured to generate an alert, e.g., a visual or an audio alert (e.g., via a light or buzzer attached thereto), in response to detecting that motion has occurred.

In general, the scope of the present invention includes acquiring a sequence of two or more images of a subject's body, in order to determine the location of a tool with respect to the body, during a medical intervention. For some applications, during such a procedure, a motion detection sensor is configured to detect that motion of the subject (or a portion of the subject) that is greater than a given threshold has occurred, for example, the motion detection sensor may be configured to detect that such motion has occurred between the acquisitions of two or more of the images. Typically, the motion detection sensor detects that a portion of the subject's body has undergone motion in a standalone manner (i.e., the motion detection sensor detects that its motion has occurred relative to a prior position of itself (as opposed to detecting that its motion has occurred relative to an external element)). In response thereto, the motion sensor generates an alert indicating to a user that such motion has occurred. For some applications, the motion detection sensor generates an output by driving an output device itself. Alternatively or additionally, in response to receiving an input from a motion detection sensor indicating that such motion has occurred, a computer processor (e.g., computer processor 22) generates an alert indicating to a user that such motion has occurred. For some applications, the computer processor generates an output advising the user to acquire additional images (e.g., to reacquire an image from a given imaging view).

As described hereinabove, typically, 2D x-ray images of a vertebra from respective views are registered to one another and to a 3D image data of the vertebra by generating a plurality of DRRs from a 3D CT image, and identifying respective first and second DRRs that match the 2D x-ray images of the vertebra. By identifying respective DRRs that match two or more x-ray images acquired from respective views, the x-ray images are registered to the 3D image data, and, in turn, the x-ray images are registered to one another via their registration to the 3D image data.

For some applications, in order to avoid double solutions when searching for a DRR that matches a given x-ray image, computer processor 22 first determines whether the x-ray image is, for example, AP, PA, left lateral, right lateral, left oblique, or right oblique, and/or from which quadrant a tool is being inserted. The computer processor may determine this automatically, e.g., by means of sets 50 of markers 52, using techniques described herein. Alternatively, such information may be manually inputted into the computer processor.

For some applications, in order to identify a DRR that matches a given x-ray image, computer processor 22 first limits the search space within which to search for a matching DRR, e.g., by using techniques such as those described in U.S. Pat. No. 9,240,046 to Carrell, which is incorporated herein by reference.

For some applications, the steps of generating a plurality of DRRs from a 3D CT image, and identifying respective first and second DRRs that match the 2D x-ray images of the vertebra are aided by deep-learning algorithms. In general, for such applications, during a learning stage, many sets of 3D CT images of vertebra and x-ray images of those same vertebra are inputted into a computer processor which functions as a deep learning engine. The registered outcome for each set, i.e., the DRRs that match the x-rays, are determined. The results of the deep learning are then inputted to computer processor 22. Subsequently, intraprocedurally, computer processor 22 uses the results of the deep learning stage to facilitate the matching of DRRs from the CT image of the subject's vertebra to x-ray images.

For some applications, deep-learning techniques are performed as part of the processing of images of a subject's vertebra, as described in the following paragraphs. By performing the deep-learning techniques, the search space for DRRs of the subject's vertebra that match the x-ray images is limited, which reduces the intraprocedural processing requirement, reduces the time taken to performing the matching, and/or reduces cases of dual solutions to the matching.

For some applications, in a first deep-learning phase, a moderate number (e.g., fewer than 10,000, or fewer than 1000, which is moderate relative to much larger data sets that are typically required for deep learning) spinal CT scans are processed, each of the CT scans comprising multiple vertebrae, for example, above 20. For each vertebra, a large number of pairs (or triplets, or greater multiples) of DRRs are generated, each pair being generated from simulated viewing distances and simulated camera angles that are typically at least 10 degrees apart. The simulated camera angles are those that are typically used in x-ray acquisition during spinal surgery, such as generally-AP, generally-left-oblique, generally-right-oblique, generally-left-lateral, and/or generally-right-lateral. All of these sets, each comprising, typically, a 3D CT and a DRR pair and the simulated camera viewing distances and angles from which the DRRs were generated, are fed into a deep-learning analytical engine. Thus, the engine learns, given a vertebral 3D CT and a pair of DRRs, to suggest simulated camera viewing distances and angles that correspond to those DRRs. Subsequently, the deep-learning data is fed as an input to computer processor 22 of system 20. Intraprocedurally, in order to register the 2D x-ray images to the 3D image data, computer processor uses the deep-learning data in order to limit the search space in which DRRs of the 3D image data that match the x-ray images should be searched for. Computer processor 22 then searches for the matching DRRs only within the search space that was prescribed by the deep-learning data.

Alternatively or additionally, during the deep-learning phase, a large database of 2D x-ray images and (at least some of) their known parameters relative to vertebra are inputted to a deep-learning engine. Such parameters typically include viewing angle, viewing distance, and optionally additional camera parameters. For some applications, the aforementioned parameters are exact. Alternatively, the parameters are approximate parameters. The parameters may be recorded originally when generating the images, or annotated by a radiologist. Thus, the engine learns, given a certain 2D projection image, to suggest simulated camera viewing distances and angles that correspond to that projection image. Subsequently, the deep-learning data is fed as an input to computer processor 22 of system 20. Intraprocedurally, in order to register the 2D x-ray images to the 3D image data, computer processor uses the deep-learning data in order to limit the search space in which DRRs of the 3D image data that match the x-ray images should be searched for. Computer processor 22 then searches for the matching DRRs only within the search space that was prescribed by the deep-learning data.

Figure 14A:
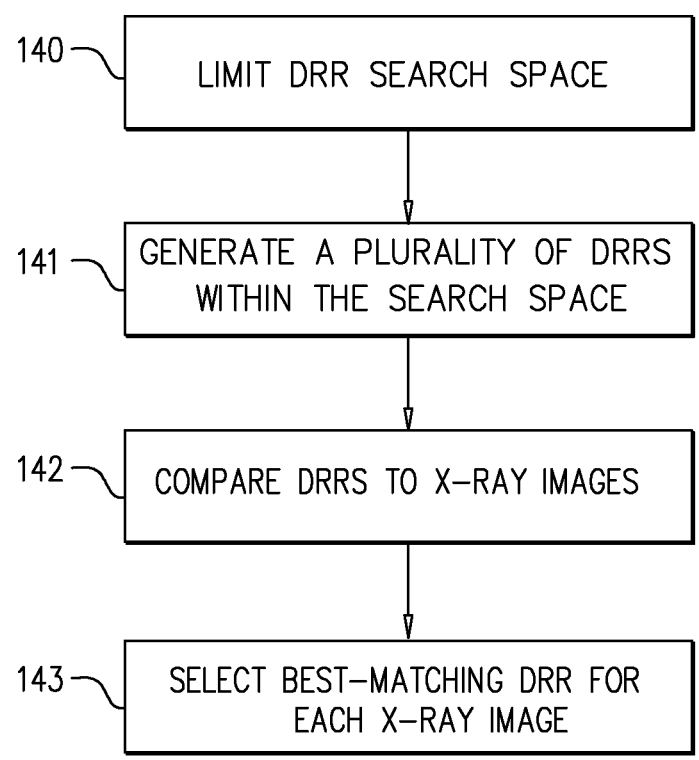
FIGS. 14A and 14B are flowcharts showing steps that are typically performed using the system of FIG. 1B, in accordance with some applications of the present invention.

The above-described registration steps are summarized in FIG. 14A, which is a flowchart showing steps that are performed by computer processor, in order to register 3D image data of a vertebra to two or more 2D x-ray images of the vertebra.

In a first step 140, the search space for DRRs that match respective x-ray images is limited, for example, using deep-learning data, and/or using techniques such as those described in U.S. Pat. No. 9,240,046 to Carrell, which is incorporated herein by reference. Alternatively or additionally, in order to avoid double solutions when searching for a DRR that matches a given x-ray image, the computer processor determines whether the x-ray images are, for example, AP, PA, left lateral, right lateral, left oblique, or right oblique, and/or from which quadrant a tool is being inserted.

In step 141, a plurality of DRRs are generated within the search space.

In step 142, the plurality of DRRs are compared with the x-ray images from respective views of the vertebra.

In step 143, based upon the comparison, the DRR that best matches each of the x-ray images of the vertebra is selected. Typically, for the simulated camera position that would generate the best-matching DRR, the computer processor determines the viewing angle and viewing distance of the camera from the 3D image of the vertebra.

It is noted that the above steps are performed separately for each of the 2D x-ray images that is used for the registration. For some applications, each time one or more new 2D x-ray images are acquired, the image(s) are automatically registered to the 3D image data using the above described technique. The 2D to 3D registration is thereby updated based upon the new 2D x-ray acquisition(s).

Figure 14B:
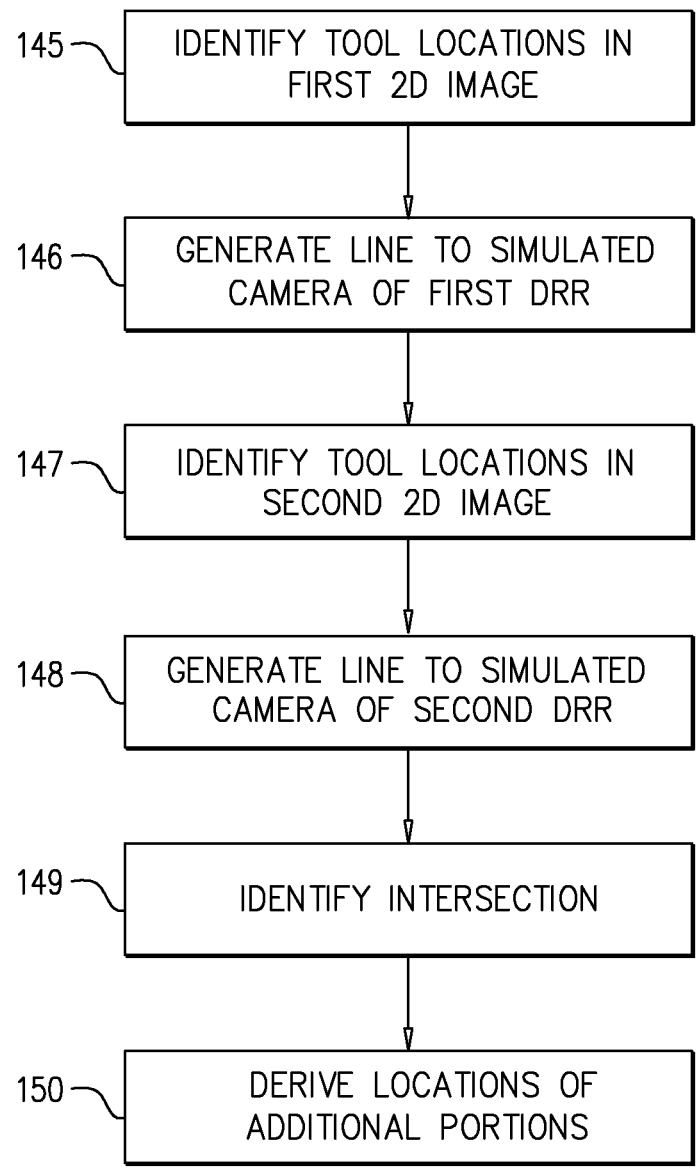

Reference is now made to FIG. 14B, which is a flowchart showing steps of an algorithm that is performed by computer processor 22 of system 20, in accordance with some applications of the present invention.

As described hereinabove, for each of the x-ray images (denoted X1 and X2), the computer processor determines a corresponding DRR from a simulated camera view (the simulated cameras being denoted C1 for X1 and C2 for X2).

The 3D scan and two 2D images are now co-registered, and the following 3D-2D bi-directional relationship generally exists:

Geometrically, a point P3D in the 3D scan of the body portion (in three coordinates) is at the intersection in 3D space of two straight lines
i. A line drawn from simulated camera C1 through the corresponding point PX1 (in two image coordinates) in 2D image X1.
ii. A line drawn from simulated camera C2 through the corresponding point PX2 (in two image coordinates) in 2D image X2.

Therefore, referring FIG. 14B, for some applications, for a portion of a tool that is visible in the 2D images, such as the tool tip or a distal portion of the tool, the computer processor determines its location within the 3D image data (denoted TP3D), using the following algorithmic steps:

Step 145: Identify, by means of image processing, the tool's tip TPX1 in image X1 (e.g., using the image processing techniques described hereinabove). For some applications, to make the tool tip point better defined, the computer processor first generates a centerline for the tool and then the tool's distal tip TPX1 is located upon on that centerline.

In general, the computer processor identifies the locations of a tool or a portion thereof in the 2D x-ray images, typically, solely by means of image processing. For example, the computer processor may identify the tool by using a filter that detects pixel darkness (the tool typically being dark), using a filter that detects a given shape (e.g., an elongated shape), and/or by using masks. For some applications, the computer processor compares a given region within the image to the same region within a prior image. In response to detecting a change in some pixels within the region, the computer processor identifies these pixels as corresponding to a portion of the tool. For some applications, the aforementioned comparison is performed with respect to a region of interest in which the tool is likely to be inserted, which may be based upon a known approach direction of the tool. For some applications, the computer processor identifies the portion of the tool in the 2D images, solely by means of image processing, using algorithmic steps as described in US 2010-0161022 to Tolkowsky, which is incorporated herein by reference.

Step 146: Generate a typically-straight line L1 from C1 to TPX1. (It is noted that, as with other steps described as being performed by the computer processor, the generation of a line refers to a processing step that is the equivalent of drawing a line, and should not be construed as implying that a physical line is drawn. Rather the line is generated as a processing step).

Step 147: Identify, by means of image processing, the tool's tip TPX2 in image X2 (e.g., using the image processing techniques described hereinabove). For some applications, to make the tool tip point better defined, the computer processor first generates a centerline for the tool and then the tool's distal tip TPX2 is located upon on that centerline. The image processing techniques that are used to tool's tip TPX2 in image X2 are generally similar to those described above with reference to step 145.

Step 148: Generate a typically-straight line L2 from C2 to TPX2.

Step 149: Identify the intersection of L1 and L2 in 3D space as the location of the tool's tip relative to the 3D scan data.

Step 150: Assuming that the shape of the tool is known (e.g., if the tool is a rigid or at least partially rigid tool, or if the tool can be assumed to have a given shape by virtue of having been placed into tissue), the computer processor derives the locations of additional portions of the tool within 3D space. For example, in case of a tool with straight shaft in whole or in its distal portion, or one that may be assumed to be straight once inserted into bone, or at least straight in its distal portion once inserted into bone, then this shaft, or at least its distal portion, resides at the intersection of two planes, each extending from the simulated camera to the shaft (or portion thereof) in the corresponding 2D image. For some applications, the direction of the shaft from its tip to proximal and along the intersection of the two planes is determined by selecting a point proximally to the tool's tip on any of the x-ray images and observing where a line generated between such point and the corresponding simulated camera intersects the line of intersection between the two planes.

It is noted that, since the coregistration of the 3D image data to the 2D images is bidirectional, for some applications, the computer processor identifies features that are identifiable within the 3D image data, and determines the locations of such features with respect to the 2D x-rays, as described in further detail hereinbelow. The locations of each such feature with respect to any of the 2D x-rays are typically determined by (a) generating a typically-straight line from the simulated camera that was used to generate the DRR corresponding to such x-ray image and through the feature within the 3D image data and (b) thereby determining the locations of the feature with respect to the x-ray images themselves.

For some applications, the locations of such features with respect to the 2D x-ray images are determined by determining the locations of the features within the DRRs that match the respective x-ray images, and assuming that the features will be at corresponding locations within the matching x-ray images.

For some applications, based upon the registration, 3D image data is overlaid upon a 2D image. However, typically, the 3D image data (e.g., a 3D image, a 2D cross-section derived from 3D image data, and/or a 2D projection image derived from 3D image data) are displayed alongside 2D images, as described in further detail hereinbelow.

Figure 15A:
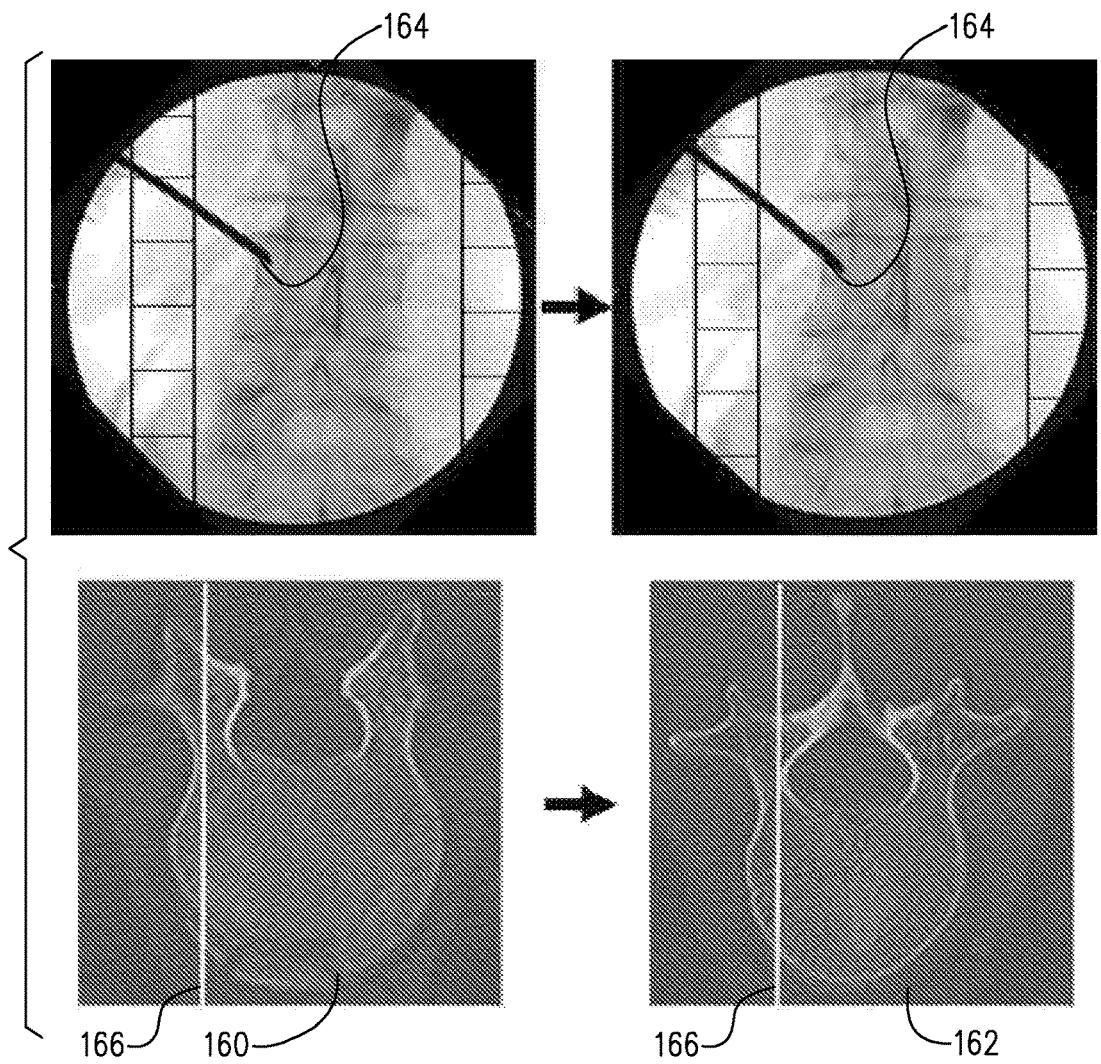
FIG. 15A shows an example of axial cross-sections of a vertebra corresponding, respectively, to first and second locations of a tip of a tool that is advanced into the vertebra along a longitudinal insertion path, as shown on corresponding 2D x-ray images that are acquired from a single x-ray image view, in accordance with some applications of the present invention.

Reference is now made to FIG. 15A, which shows an example of cross-sections 160 and 162 of a vertebra corresponding, respectively, to first and second locations of a tip 164 of a tool that is advanced into the vertebra along a longitudinal insertion path, as shown on corresponding 2D x-ray images, in accordance with some applications of the present invention. Typically, the tool has a straight shaft in whole or in its distal portion, and/or may be assumed to be straight once inserted into bone, or at least straight in its distal portion once inserted into bone. Referring also to step 84 of FIG. 7, for some applications, based upon the identified location of the tip of tool with respect to one or more 2D x-ray image of the vertebra that are acquired from a single image view, and the registration of an x-ray from the single 2D x-ray image view to the 3D image data (e.g., by matching a DRR from the 3D image data to the 2D x-ray image), computer processor 22 determines a location of the tip of the tool with respect to a DRR that is derived from the 3D image data (e.g., the DRR that was determined to match the 2D x-ray image), and in response thereto, drives the display to display a cross-section of the vertebra, the cross-section being derived from the 3D image data, and corresponding to the location of the tool tip. The cross-section is typically of a given plane at the identified location. Typically, the cross-section is an axial cross-section, but for some applications, the cross-section is a sagittal cross-section, a coronal cross-section, and/or a cross-section that is perpendicular to or parallel with the direction of the tool insertion.

For some applications, upon the cross-section, the computer processor drives the display to show a line 166 (e.g., a vertical line), indicating that the location of the tip of the tool is somewhere along that line. For some applications, the line is drawn vertically upon an axial cross-section of the vertebra, as shown. For some applications, the surgeon is able to determine the likely location of the tool along the line based upon their tactile feel. Alternatively or additionally, based on the 3D image data, the computer processor drives the display to display how deep below the skin the vertebra is disposed, which acts as a further aid to the surgeon in determining the location of the tool along the line.

As noted above, typically it is possible to generate an output as shown in FIG. 15A, by acquiring one or more 2D x-ray images from only a single x-ray image view of the tool and the vertebra, and registering one of the 2D x-ray images to the 3D image data using the registration techniques described herein. Typically, by registering the 2D x-ray image acquired from the single image view to the 3D image data, computer processor 22 determines, with respect to 3D image data (e.g., with respect to the DRR that was determined to match the 2D x-ray image), (a) a plane in which the tip of the tool is disposed, and (b) a line within the plane, somewhere along which the tip of the tool is disposed, as shown in FIG. 15A. As described hereinabove, typically, when the tip of the tool is disposed at an additional location with respect to the vertebra, further 2D x-ray images of the tool at the additional location are acquired from the same single x-ray image view, or a different single x-ray image view, and the above-described steps are repeated. Typically, for each location of the tip of the tool to which the above-described technique is applied, 2D x-ray images need only be acquired from a single x-ray image view, which may stay the same for the respective locations of the tip of the tool, or may differ for respective locations of the tip of the tool.

Figure 15B:
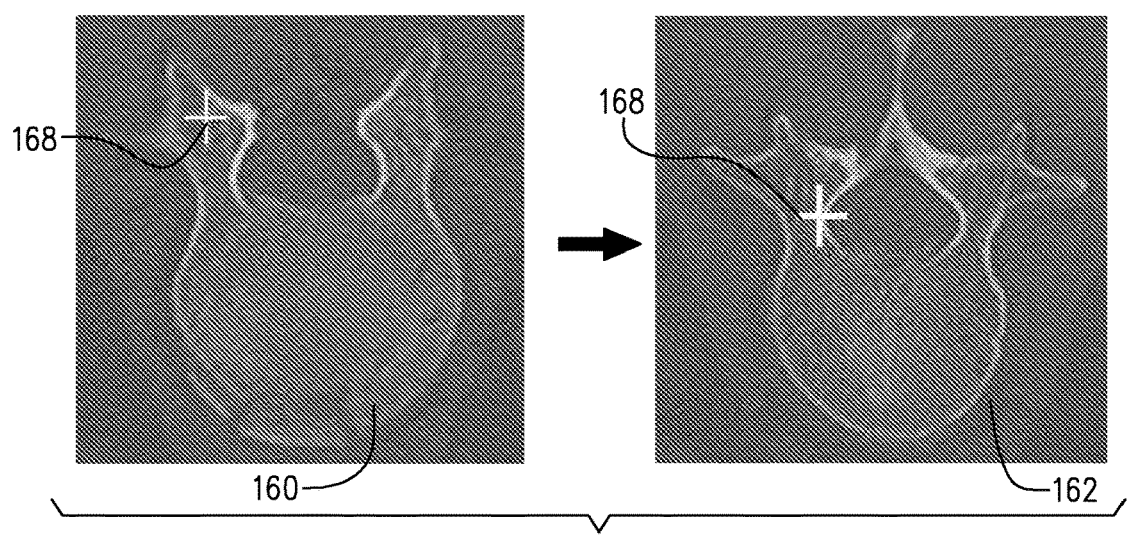
FIG. 15B shows an example of axial cross-sections of a vertebra upon which, respectively, first and second locations of a tip of a tool that is advanced into the vertebra along a longitudinal insertion path are displayed, the locations being derived using x-ray images acquired from two or more x-ray image views, in accordance with some applications of the present invention.

Reference is now made to FIG. 15B, which is a schematic illustration of the location of the tool tip 168 denoted by cross-hairs upon cross-sections 160 and 162 of the vertebra corresponding, respectively, to first and second locations of a tip 164 of a tool that is advanced into the vertebra along a longitudinal insertion path (as shown in FIG. 15A), in accordance with some applications of the present invention. For some applications, by initially registering two or more 2D x-ray images of the tool and the vertebra that were acquired from respective 2D x-ray image views, to the 3D image data, the precise location of the tip of the tool within a cross-section derived from the 3D image data is determined and indicated upon the cross-section, as shown in FIG. 15B. As described hereinbelow, with reference to FIGS. 19A-19B, for some applications, after initially determining the location of the tip of the tool with respect to the 3D image data using two or more 2D x-ray images of the tool and the vertebra that were acquired from respective 2D x-ray image views, subsequent locations of the tip of the tool are determined with respect to the 3D image data by acquiring further x-ray images from only a single x-ray image view.

Figure 16A:
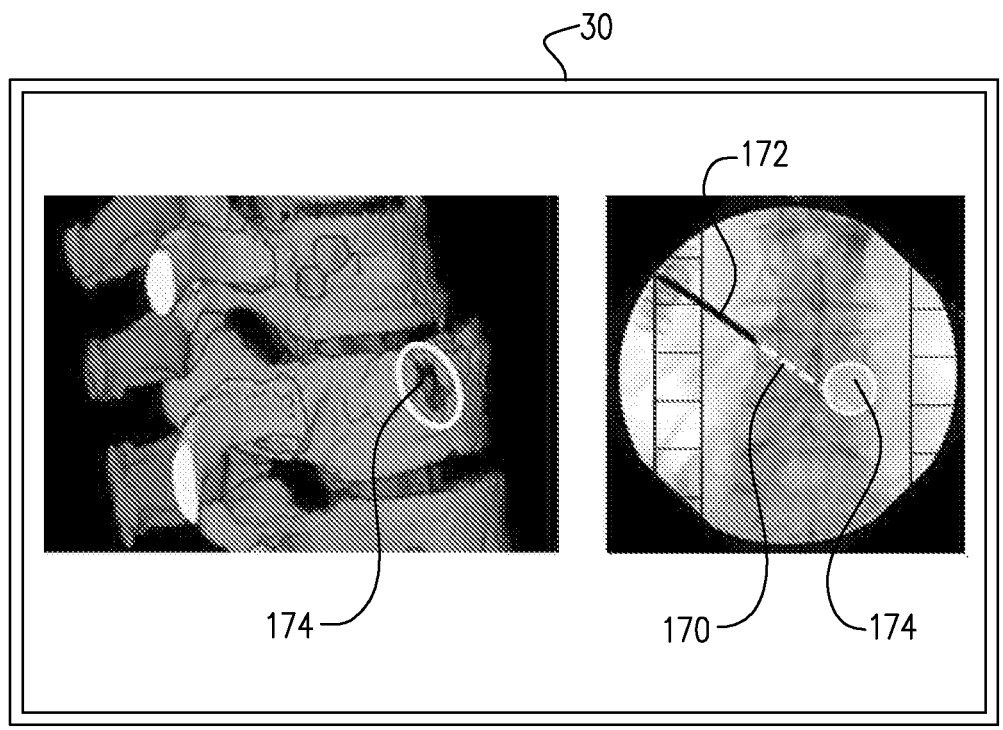
FIGS. 16A and 16B show examples of a display showing a given location designated upon 3D (e.g., CT or MRI) image data and a relationship between an anticipated longitudinal insertion path of a tool and the given location upon, respectively, AP and lateral 2D x-ray images, in accordance with some applications of the present invention.
Figure 16B:
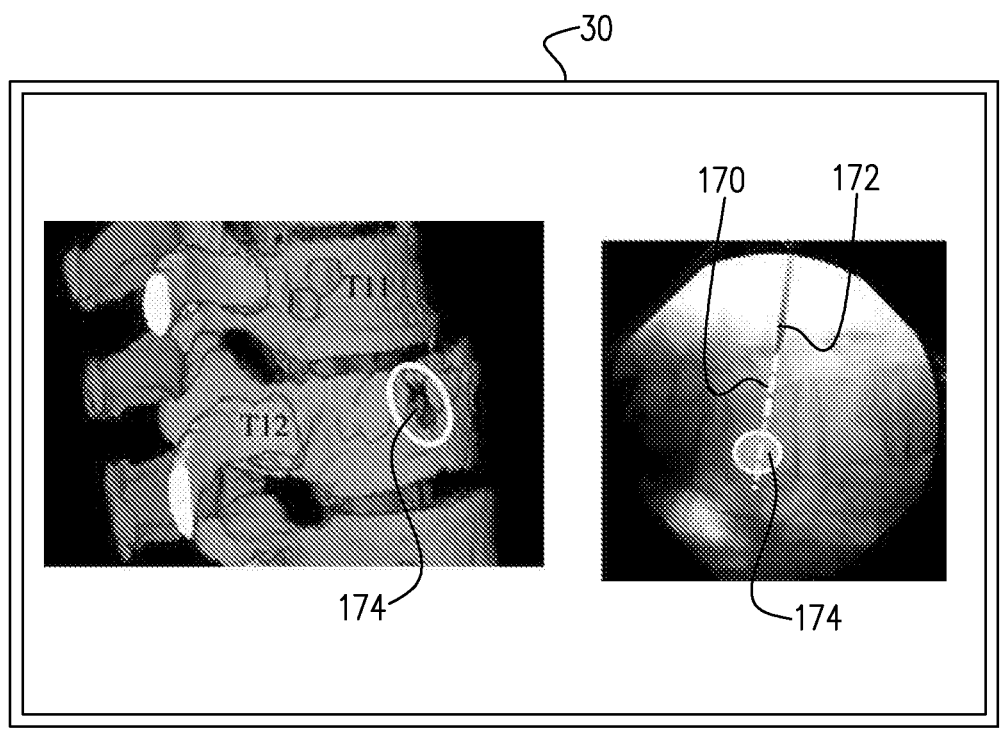

Reference is now made to FIGS. 16A and 16B, which show examples of a display showing a relationship between an anticipated longitudinal insertion path 170 of a tool 172 and a designated location 174 upon, respectively, AP and lateral 2D x-ray images, in accordance with some applications of the present invention. Reference is also made to step 86 of FIG. 7.

For some applications, a location within a vertebra is designated within the 3D image data. For example, an operator may designate a target portion (e.g. a fracture, a tumor, a virtual pedicle screw, etc.), and/or a region which the tool should avoid (such as the spinal cord) upon the 3D image data (e.g., a 3D image, a 2D cross-section derived from 3D image data, and/or a 2D projection image derived from 3D image data). Alternatively or additionally, the computer processor may identify such a location automatically, e.g., by identifying the portion via image processing. Based upon the registration of the first and second 2D x-ray images to the 3D image data, the computer processor derives a position of the designated location within at least one of the x-ray images, using the techniques described hereinabove. In addition, the computer processor determines an anticipated path of the tool within the x-ray image. Typically, the computer processor determines the anticipated path by determining a direction of an elongate portion of the tool (and/or a center line of the elongate portion) within the x-ray image. Since the tool is typically advanced along a longitudinal insertion path, the computer processor extrapolates the anticipated path by extrapolating a straight line along the determined direction.

For some applications, the computer processor performs a generally similar process, but with respect to a desired approach vector (e.g., for insertion and implantation of a screw) that, for example, is input into the computer processor manually, and/or is automatically derived by the processor. For example, such an approach vector may have been generated during a planning phase, typically upon the 3D image data, and based upon the insertion of a simulated tool into the vertebra. Typically, such an approach vector is one that reaches a desired target, while avoiding the spinal cord or exiting the vertebra sideways.

For some applications, in response to the above steps, the computer processor generates an output indicating a relationship between the anticipated longitudinal insertion path of the tool and the designated location. For some applications, the computer processor generates an output on the display, e.g., as shown in FIGS. 16A and 16B. Alternatively or additionally, the computer processor may generate instructions to the operator to redirect the tool. Further alternatively or additionally, the computer processor may generate an alert (e.g., an audio or visual alert) in response to detecting that the tool is anticipated to enter a region that should be avoided (such as the spinal cord), or is anticipated to exit the vertebra sideways in the other direction.

Referring again to step 90 of FIG. 7, for some applications, computer processor 22 determines a location of a portion of the tool with respect to the vertebra, within the x-ray images, by means of image processing, as described hereinabove. Based upon the identified location of the portion of the tool within the x-ray images, and the registration of the first and second 2D x-ray images to the 3D image data, the computer processor determines the location of the portion of the tool with respect to the 3D image data. For some applications, in response thereto, the computer processor shows an image of the tool itself, or a symbolic representation thereof, overlaid upon the 3D image data. Alternatively or additionally, the computer processor derives a relationship between the location of the portion of the tool with respect to the 3D image data and a given location within the 3D image data, and generates an output that is indicative of the relationship. As described hereinabove, the registration of the 2D images to the 3D image data is typically performed with respect to individual vertebrae. Therefore, even is the subject has moved between the acquisition of the 3D image data and the acquisitions of the 2D images, the techniques described herein are typically effective.

For some applications, the computer processor generates an output that is indicative of the distance of the tip of the tool from the spinal cord and/or outer vertebral border, e.g., using numbers or colors displayed with respect to the 3D image data. For some applications, the computer processor outputs instructions (e.g., textual, graphical, or audio instructions) indicating that the tool should be redirected. For some applications, as an input to this process, the computer processor determines or receives a manual input indicative of a direction or orientation from which the tool is inserted (e.g., from top or bottom, or left or right).

Figure 17A:
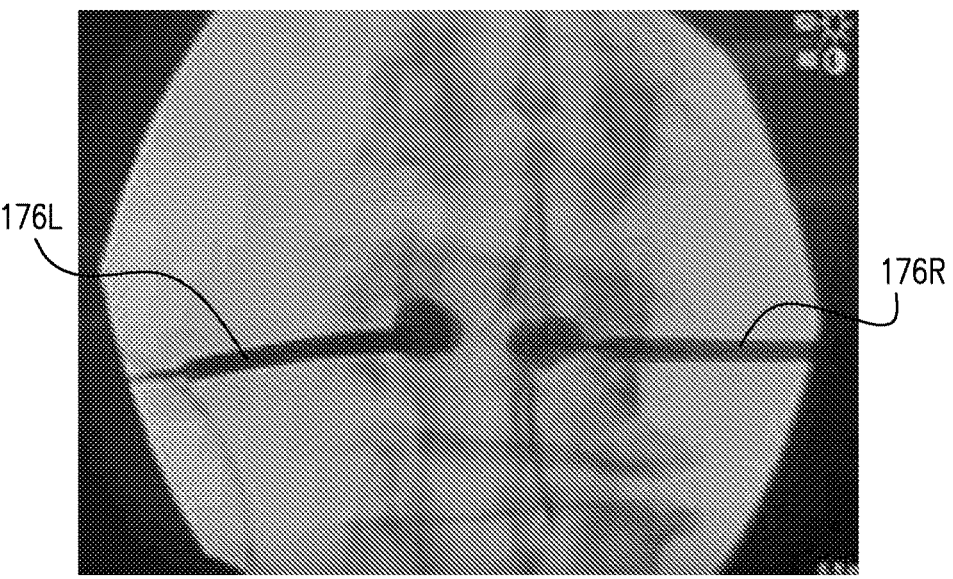
FIG. 17A shows an AP x-ray of two tools being inserted into a vertebra through, respectively, 10-11 o'clock and 1-2 o'clock insertion windows, the AP x-ray being generated using prior art techniques.
Figure 17B:
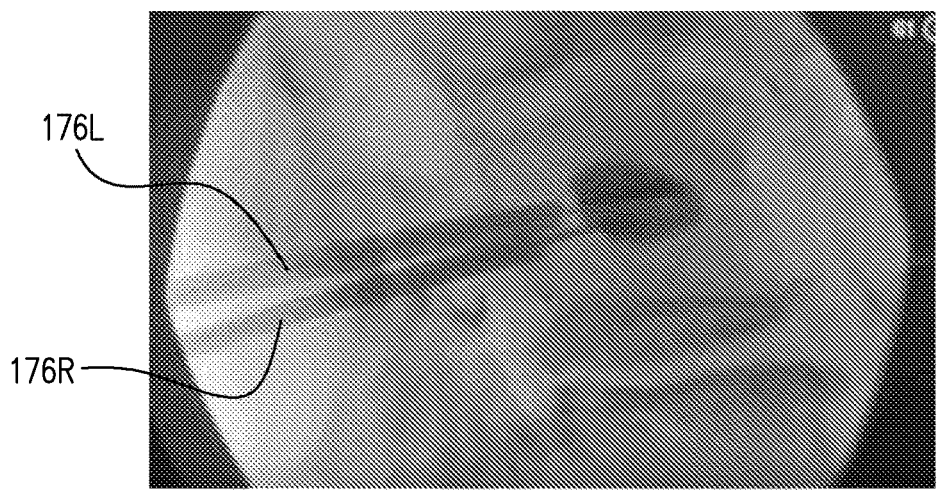
FIG. 17B shows a corresponding lateral x-ray image to FIG. 17A, the lateral x-ray being generated using prior art techniques.

Reference is now made to FIG. 17A shows an AP x-ray of two tools 176L and 176R being inserted into a vertebra through, respectively, 10-11 o'clock and 1-2 o'clock insertion windows, and to FIG. 17B, which shows a corresponding lateral x-ray image to FIG. 17A, the images being acquired in accordance with prior art techniques. As described hereinabove, in many cases, during spinal surgery, two or more tools are inserted into a vertebra, for example, from the 10 o'clock to 11 o'clock insertion window and from the 1 o'clock to 2 o'clock insertion window, with the process repeated, as applicable, for one or more further vertebrae. Within the AP x-ray view, the tools inserted into respective windows are typically discernible from one another, as shown in FIG. 17A. Furthermore, with reference to FIGS. 6A-B, for some applications, within the AP view, the computer processor discerns between tool inserted via the respective insertion windows based upon the arrangements of marker sets 50A and 50B (and in some cases 50C). However, if the tools are of identical or similar appearance, then from some imaging directions it is challenging to identify which tool is which. In particular, it is challenging to identify which tool is which in lateral x-ray views, as may be observed in FIG. 17B. In general, it is possible to discern between tools in images acquired along the direction of insertion, and more difficult to discern between tools in images acquired along other directions.

For some applications, as a solution to the above-described challenge, the computer processor provides the operator with an interface to identify one or more of the tools within an x-ray image, e.g., by matching tools within a first image that was acquired from a view in which the tools are discernable from one another (e.g., the AP view) to tools within a second image that was acquired from a view in which the tools are not discernable from one another (e.g., the lateral view). Alternatively or additionally, since the tools are typically inserted sequentially and all of the tool insertions are performed under x-ray imaging, when the first tool is inserted, images are acquired from both a first image view in which tools are discernable from one another (e.g., the AP view) and a second image view in which tools are not discernable from one another (e.g., the lateral view) are acquired. The computer processor thereby identifies the tool as being the first tool, even in the image acquired from the second image view in which tools are not discernable from one another. Subsequently, when the second tool is inserted and the images (from the same, or similar, two views) are reacquired, the computer processor is able to identify the second tool, even in images acquired from the second image view in which tools are not discernable from one another, since the identification of the first tool has already been performed. The computer processor then keeps track of which tool is which along the sequence of x-ray images. For some applications, once the computer processor has determined which tool is which, the computer processor indicates which tool is which at all relevant stages throughout the procedure (e.g., by color-coding or labelling the tools), with respect to all x-ray views, and/or with respect to the 3D image data.

Referring again to step 90 of FIG. 7, for some applications, rather than displaying the tool, a representation thereof, and/or a path thereof upon a 3D image, the computer processor drives the display to display the tool, a representation thereof, and/or a path thereof upon a 2D cross-section of the vertebra that is derived from the 3D image. For some applications, the computer processor determines the location of the centerline of the tool shaft, by means of image processing. For example, the computer processor may use techniques for automatically identifying a centerline of an object as described in US 2010-0161022 to Tolkowsky, which is incorporated herein by reference. For some applications, the computer processor drives the display to display the centerline of the tool upon the 3D image data, the end of the centerline indicating the location of the tool tip within the 3D image data. Alternatively or additionally, the computer processor drives the display to display an extrapolation of the centerline of the tool upon the 3D image data, the extrapolation of the centerline indicating an anticipated path of the tool with respect to the 3D image data. For some applications, the computer processor drives the display to display a dot at the end of the extrapolated centerline upon the 3D image data, the dot representing the anticipated location of the tip of the tool.

For some applications, the computer processor drives the display to display in a semi-transparent format a 3D image of the vertebra with the tool, a representation thereof, and/or a path thereof disposed inside the 3D image. Alternatively or additionally, the computer processor drives the display to rotate the 3D image of the vertebra automatically (e.g., to rotate the 3D image back-and-forth through approximately 30 degrees). For some applications, the computer processor retrieves an image of a tool of the type that is being inserted from a library and overlays the image upon the derived centerline upon the 3D image data. Typically, the tool is placed along the centerline at an appropriate scale with the dimensions being derived from the 3D image data. For some applications, a cylindrical representation of the tool is overlaid upon the derived centerline upon the 3D image data. For some applications, any one of the above representations is displayed relative to a predesignated tool path, as derived automatically by processor 22, or as input manually by the surgeon during a planning stage.

Referring again to FIG. 2, tool insertion into a vertebra must avoid the spinal cord 42, and at the same time needs to avoid exiting the vertebra from the sides, leaving only two narrow tool insertion windows 44, on either side of the vertebra. Typically, the greater the level of protrusion of a tool or implant into the spinal cord, the worse the clinical implications. For some applications, volumes within the 3D image of the vertebra (and/or a cross-sectional image derived therefrom) are color coded (e.g., highlighted) to indicate the level of acceptability (or unacceptability) of protrusion into those volumes. For some applications, during the procedure, the computer processor determines the location of the tool with respect to the 3D image data, and in response thereto, the computer processor drives the display to highlight a vertebral volume into which there is a protrusion that is unacceptable. For some applications, the computer processor drives the display to display a plurality (e.g., 2-6) of, typically concentric, cylinders within the 3D image of the vertebra, the cylinders indicating respective levels of acceptability of protrusion of a tool into the volumes defined by the cylinders. During the procedure, the computer processor determines the location of the tool with respect to the 3D image data, and in response thereto, the computer processor drives the display to highlight the cylinder in which the tool or a portion thereof is disposed, and/or is anticipated to enter. For some applications, the computer processor performs the above-described functionalities, but not with respect to the tool that is currently being inserted (which may be a narrow tool, such as a needle), rather with respect to the eventual implant (e.g., a pedicle screw, which typically has a larger diameter) that will be positioned later using the current tool. For some applications, the computer processor performs the above-described steps with respect to a 2D cross-sectional image that is derived from the 3D image data. For such cases, rectangles, rather than cylinders are typically used to represent the respective levels of acceptability of protrusion of a tool into the areas defined by the rectangles.

For some applications, the processor allows a 3D image of the vertebra with the tool, a representation of the tool, and/or a path of the tool indicated within the image to be rotated, or the processor rotates the image automatically, in order for the user to better understand the 3D placement of the tool. It is noted that, since the images of the vertebra and the tool were input from different imaging sources, the segmented data of what is the tool (or its representation) and what is the vertebra is in-built (i.e., it is already known to the computer processor). For some applications, the computer processor utilizes this in-built segmentation to allow the operator to virtually manipulate the tools with respect to the vertebra. For example, the operator may virtually advance the tool further along its insertion path, or retract the tool and observe the motion of the tool with respect to the vertebra. For some applications, the computer processor automatically virtually advances the tool further along its insertion path, or retracts the tool with respect to the vertebra in the 3D image data.

For some applications, accuracy of determining the position of the portion of the tool within the 3D image data is enhanced by registering three 2D x-ray images to the 3D image data, the images being acquired from respective, different views from one another. Typically, for such applications, an oblique x-ray image view is used in addition to AP and lateral views. For some applications, accuracy of determining the position of the portion of the tool within the 3D image data is enhanced by using x-ray images in which multiple portions of the tool, or portions of multiple tools, are visible and discernible from one another in the x-ray images. For some applications, the tools are discerned from one another based on a manual input by the operator, or automatically by the computer processor. For some applications, accuracy of determining the position of the portion of the tool within the 3D image data is enhanced by referencing the known shapes and/or dimensions of radiopaque markers 52 as described hereinabove.

Figure 18:
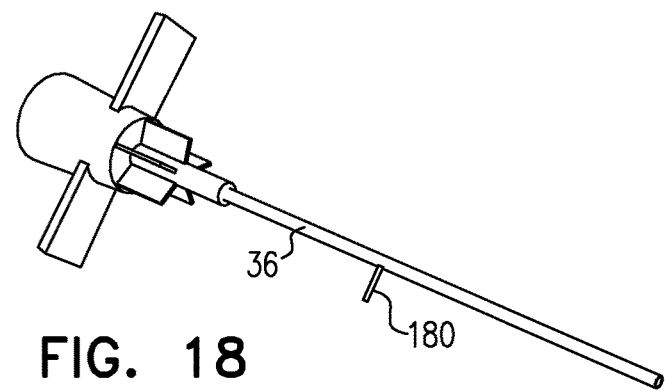
FIG. 18 is a schematic illustration of a Jamshidi™ needle with a radiopaque clip attached thereto, in accordance with some applications of the present invention.

Reference is now made to FIG. 18, which is a schematic illustration of Jamshidi™ needle 36 with a radiopaque clip 180 attached thereto, in accordance with some applications of the present invention. For some applications, accuracy of determining the position of the portion of the tool within the 3D image data is enhanced by adding an additional radiopaque element to the tool (such as clip 180), such that the tool has at least two identifiable features in each 2D image, namely, its distal tip and the additional radiopaque element. For some applications, the additional radiopaque element is configured to be have a defined 3D arrangement such that the additional radiopaque element provides comprehension of the orientation of the tool. For example, the additional radiopaque element may include an array of radiopaque spheres. For some applications, the additional radiopaque element facilitates additional functionalities, e.g., as described hereinbelow. For some applications, the tool itself includes more than one radiopaque feature that is identifiable in each 2D x-ray image. For such applications, an additional radiopaque element (such as clip 180) is typically not attached to the tool.

For some applications, the imaging functionalities described above with reference to the 3D image data are performed with respect to the 2D x-ray images, based upon the coregistration of the 2D images to the 3D image data. For example, the tool may be color-coded in the x-ray images according to how well the tool is placed. For some applications, if the tool is placed incorrectly, the computer processor drives the display to show how the tool should appear when properly placed, within the 2D x-ray images.

Figure 19A:
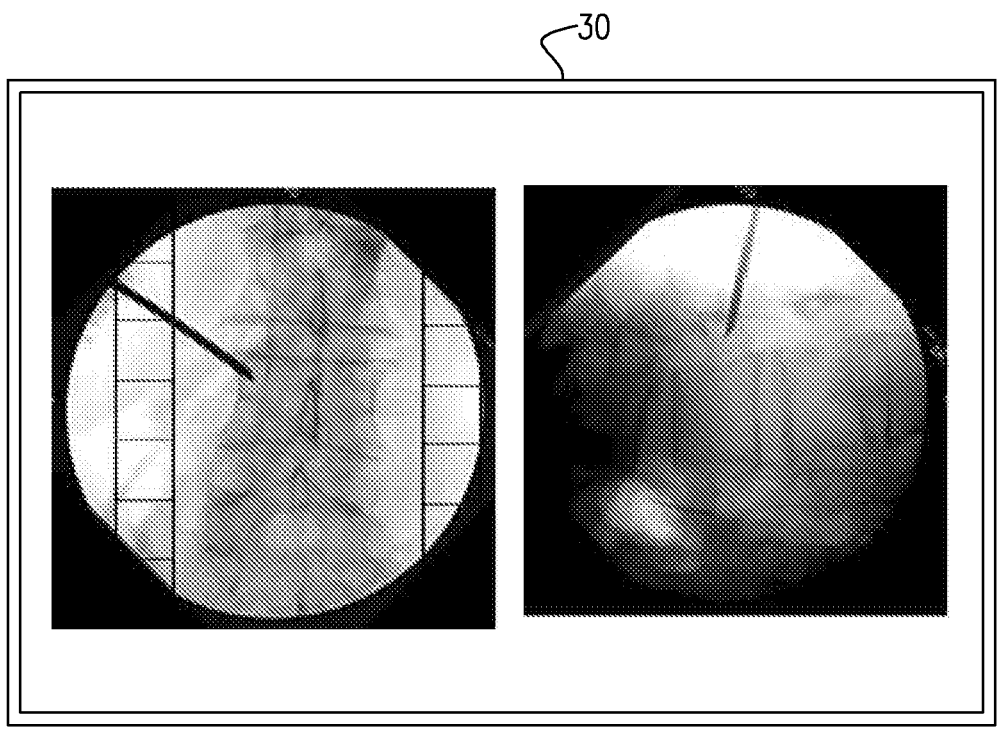
FIG. 19A shows an AP x-ray image and a corresponding lateral x-ray image of a vertebra, at a first stage of the insertion of a tool into the vertebra, in accordance with some applications of the present invention.
Figure 19B:
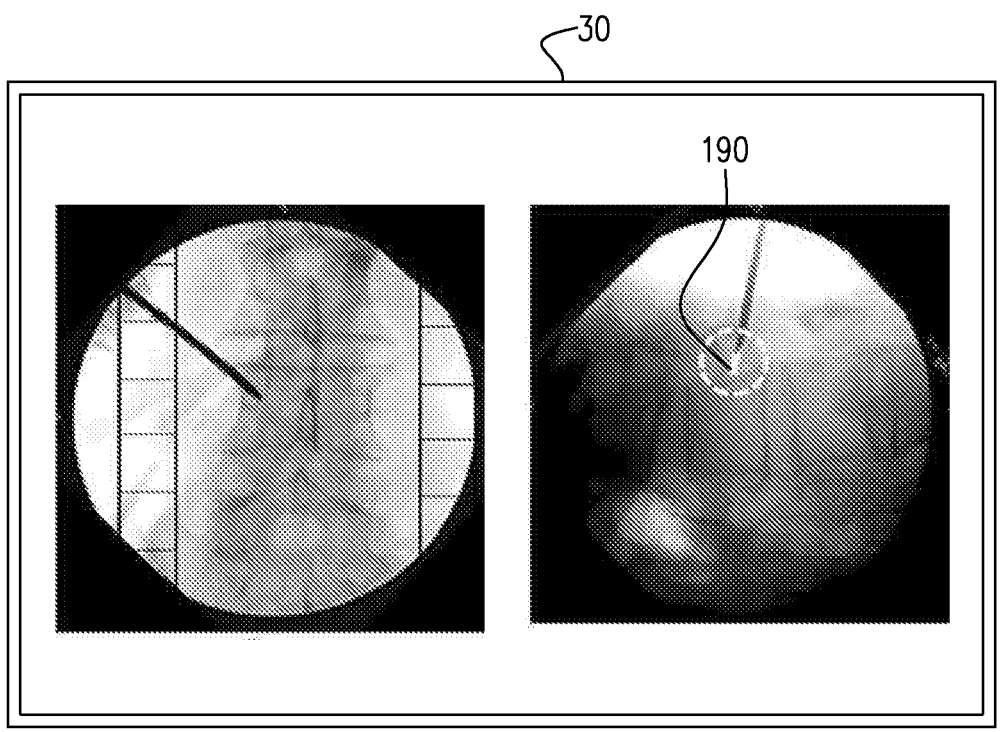
FIG. 19B shows an AP x-ray image of the vertebra, at a second stage of the insertion of the tool into the vertebra, and an indication of the derived current location of the tool tip displayed upon a lateral x-ray image of the vertebra, in accordance with some applications of the present invention.

Reference is now made to FIGS. 19A and 19B, which show examples of AP x-ray images and corresponding lateral x-ray images of a vertebra, at respective stages of the insertion of a tool into the vertebra, in accordance with some applications of the present invention. Reference is also made to step 88 of FIG. 7. A common practice in spinal surgery that is performed under x-ray is to use two separate c-arm poses (typically any two of AP, lateral and oblique) to gain partial 3D comprehension during tool insertion and/or manipulation. This typically requires moving the C-arm back and forth, and exposes the patient to a high radiation dose.

For some applications of the present invention, images are initially acquired from two poses, which correspond to respective image views. For example, FIG. 19A shows examples of AP and lateral x-ray images of a tool being inserted dorsally into a vertebra. Subsequently, the C-arm is maintained at a single pose for repeat acquisitions during tool insertion and/or manipulation, but the computer processor derives the position of the tool with respect to the vertebra in additional x-ray imaging views, and drives the display to display the derived position of the tool with respect to the vertebra in the additional x-ray image views. For example, FIG. 19B shows an example of an AP image of the tool and the vertebra of FIG. 19A, but with the tool having advanced further into the vertebra relative to FIG. 19A. Based upon the AP image in which the tool has advanced the computer processor derives the new, calculated position of the tool with respect to the lateral x-ray imaging view, and drives the display to display a representation 190 of the new tool position upon the lateral image.

Typically, the new, calculated tool position is displayed upon the lateral image, in addition to the previously-imaged position of the tool tip within the lateral image, as shown in FIG. 19B. Typically, the computer processor derives the location of portion of the tool with respect to one of the two original 2D x-ray image views, based upon the current location of the portion of the tool as identified within a current 2D x-ray image, and a relationship that is determined between images that were acquired from the two original 2D x-ray image views, as described in further detail hereinbelow.

For some applications, the repeat acquisitions are performed from a 2D x-ray image view that is the same as one of the original 2D x-ray image views, while for some applications the repeat acquisitions are performed from a 2D x-ray image view that is different from both of the original 2D x-ray image views. For some applications, in the subsequent step, the tool within the vertebra is still imaged periodically from one or more additional 2D x-ray image views, in order to verify the accuracy of the position of the tool within the additional views that was derived by the computer processor, and to correct the positioning of the tool within the additional 2D x-ray image views if necessary. For some applications, the C-arm is maintained at a single pose (e.g., AP) for repeat acquisitions during tool insertion and/or manipulation, and the computer processor automatically derives the location of portion of the tool with respect to the 3D image data of the vertebra, and updates the image of the tool (or a representation thereof) within the 3D image data.

Typically, applications as described with reference to FIGS. 19A-B are used with a tool that is inserted into the skeletal anatomy along a longitudinal (i.e., a straight-line, or generally-straight-line) insertion path. For some applications, the techniques are used with a tool that is not inserted into the skeletal anatomy along a straight-line insertion path. For such cases, the computer processor typically determines the non-straight line anticipated path of progress of the tool by analyzing prior progress of the tool, and/or by observing anatomical constraints along the tool insertion path and predicting their effect. For such applications, the algorithms described hereinbelow are modified accordingly.

For some applications, the techniques described with reference to FIGS. 19A-B are performed with respect to a primary x-ray imaging view which is typically from the direction along which the intervention is performed (and typically sets 50 of markers 52 are placed on or near the subject such that the markers appear in this imaging view), and a secondary direction from which images are acquired to provide additional 3D comprehension. In cases in which interventions are performed dorsally, the primary x-ray imaging view is typically generally AP, while the secondary view is typically generally lateral.

For some applications, computer processor 22 uses one of the following algorithms to perform the techniques described with reference to FIGS. 19A-B.

Algorithm 1:
1. The original two 2D x-ray images X1 and X2 are registered to 3D image data using the techniques described hereinabove.
2. Based upon the registration, a generally-straight-line of the tool TL (e.g., the centerline, or tool shaft), as derived from the 2D x-ray images, is positioned with respect to the 3D image data as TL-3D.
3. The generally-straight-line of the tool with respect to the 3D image data is extrapolated to generate a forward line F-TL3D with respect to the 3D image data.
4. When the tool is advanced, a new 2D x-ray X1^ is acquired from one of the prior poses only, e.g., from the same pose from which the original X1 was acquired. (Typically, to avoid moving the C-arm, this is the pose at which the most recent of the two previous 2D x-rays was acquired.)

For some applications, the computer processor verifies that there has been no motion of the C-arm with respect to the subject, and/or vice versa, between the acquisitions of X1 and X1^, by comparing the appearance of markers 52 in the two images. For some applications, if there has been movement, then Algorithm 2 described hereinbelow is used.

5. The computer processor identifies, by means of image processing, the location of the tool's distal tip in image X1^. This is denoted TPX1^.
6. The computer processor registers 2D x-ray image X1^ to the 3D image data using the DRR that matches the first x-ray view. It is noted that since pose did not change between the acquisitions of X1 and X1^, the DRR that matches x-ray X1^ is same as for x-ray X1. Therefore, there is no need to re-search for the best DRR to match to x-ray X1^.
7. The computer processor draws a line with respect to the 3D image data from C1 through TPX1^.
8. The computer processor identifies the intersection of that line with the F-TL3D line as the new location of the tip, with respect to the 3D image data. It is noted that in cases in which the tool has been retracted, the computer processor identifies the intersection of the line with the straight-line of the tool with respect to the 3D image data TL-3D, rather than with forward line F-TL3D with respect to the 3D image data.
9. The computer processor drives the display to display the tool tip (or a representation thereof) at its new location with respect to the 3D image data, or with respect to x-ray image X2.

Algorithm 2:
1. The original two 2D x-ray images X1 and X2 are registered to 3D image data using the techniques described hereinabove.
2. Based upon the registration, a generally-straight-line TL of the tool (e.g., the centerline, or tool shaft) as derived from the x-ray images is positioned with respect to the 3D image data as TL-3D.
3. The generally-straight-line of the tool with respect to the 3D image data is extrapolated to generate a forward line F-TL3D with respect to the 3D image data.
4. When the tool is advanced, a new 2D x-ray X3 is acquired from, typically, any pose, and not necessarily one of the prior two poses.
5. The computer processor identifies, by means of image processing, the location of the tool's distal tip in image X3. This is denoted TPX3.
6. The computer processor registers 2D x-ray image X3 to the 3D image data of the vertebra by finding a DRR that best matches 2D x-ray image X3, using the techniques described hereinabove. The new DRR has a corresponding simulated camera position C3.
7. The computer processor draws a line with respect to the 3D image data from C3 through TPX3.
8. The computer processor identifies the intersection of that line with the F-TL3D line as the new location of the tip, with respect to the 3D image data. It is noted that in cases in which the tool has been retracted, the computer processor identifies the intersection of the line with the straight-line of the tool with respect to the 3D image data TL-3D, rather than with forward line F-TL3D with respect to the 3D image data.
9. The computer processor drives the display to display the tool tip (or a representation thereof) at its new location with respect to the 3D image data, or with respect to x-ray image X1 and/or X2.

Figure 20:
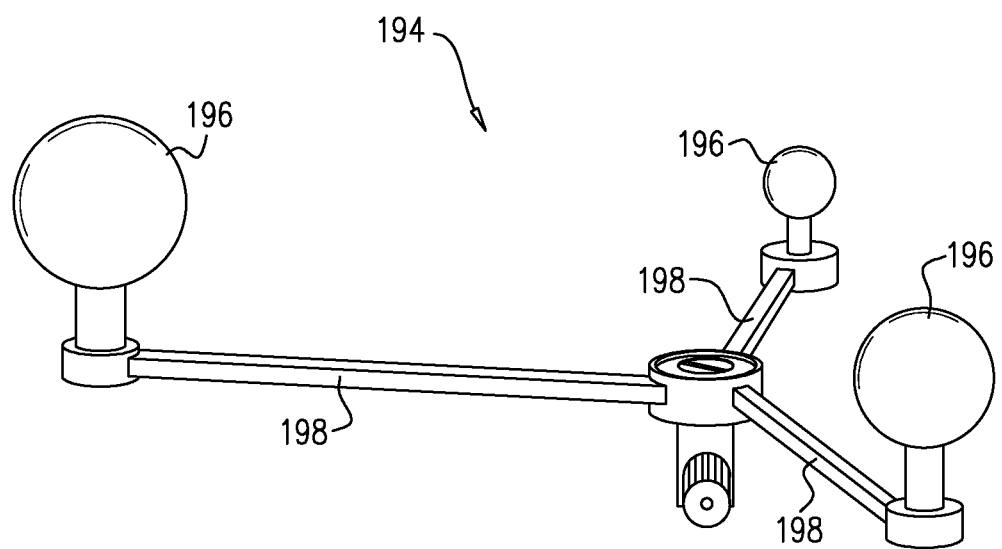
FIG. 20 is a schematic illustration of a three-dimensional rigid jig that comprises at least portions thereof that are radiopaque and function as radiopaque markers, the radiopaque markers being disposed in a predefined three-dimensional arrangement, in accordance with some applications of the present invention.

Algorithm 3:
Reference is now made to FIG. 20, which is a schematic illustration of a three-dimensional rigid jig 194 that comprises at least portions 196 thereof that are radiopaque and function as radiopaque markers, the radiopaque markers being disposed in a predefined three-dimensional arrangement, in accordance with some applications of the present invention. For some applications, as shown, radiopaque portions 196 are radiopaque spheres (which, for some applications, have different sizes to each other, as shown), and the spheres are coupled to one another by arms 198 that are typically radiolucent. Typically, the spheres are coupled to one another via the arms, such that the spatial relationships between the spheres are known precisely.

The following algorithm is typically implemented by computer processor 22 even in cases in which the x-ray images are not registered with 3D image data of the vertebra. Typically, this algorithm is for use with a three-dimensional radiopaque jig, such as jig 194, sufficient portions of which are visible in all applicable x-ray images and can be used to relate them to one another. For some applications, the jig includes a 3D array of radiopaque spheres, as shown in FIG. 20. For example, the jig may be attached to the surgical table.

1. The original two 2D x-ray images X1 and X2 are registered to one another, using markers of the jig as an anchor to provide a 3D reference frame.
2. When the tool is advanced, a new x-ray X1^ is acquired from one of the prior poses, e.g., from the same pose from which the original X1 was acquired. (Typically, to avoid moving the C-arm, this is the pose at which the most recent of the two-previous x-ray was acquired.)

For some applications, the computer processor verifies that there has been no motion of the C-arm with respect to the subject, and/or vice versa, between the acquisitions of X1 and X1^, by comparing the appearance of markers 52 (typically, relative to the subject's visible skeletal portion), and/or portions 196 of jig 194 (typically, relative to the subject's visible skeletal portion), in the two images. For some applications, if there has been movement, then one of the other algorithms described herein is used.

3. The computer processor identifies, by means of image processing, the location of the tool's distal tip in image X1^. This is denoted TPX1^.
4. The computer processor registers 2D x-ray image X1^ with X2 using the jig.
5. The computer processor calculates the new location of the tool tip upon X2, based upon the registration.

6. The computer processor drives the display to display the tool tip (or a representation thereof) at its new location with respect to x-ray image X2.

Algorithm 4:

The following algorithm is typically implemented by computer processor 22 even in cases in which the x-ray images are not registered with 3D image data of the vertebra. Typically, this algorithm is for use with a tool that has two or more identifiable points in each 2D x-ray image. For example, this algorithm may be used with a tool to which a clip, or another radiopaque feature is attached as shown in FIG. 18.

1. Within the original two 2D x-ray images X1 and X2, the computer processor identifies, by means of image processing, the two identifiable points of the tool, e.g., the distal tip and the clip.
2. The computer processor determines a relationship between X1 and X2, in terms of image pixels. For example:
    a. In X1, the two-dimensional distances between the tool tip and the clip are dx1 pixels horizontally and dy1 pixels vertically.
    b. In X2, the two-dimensional distances between the tool tip and the clip are dx2 pixels horizontally and dy2 pixels vertically
    c. Thus, the computer processor determines a 2D relationship between the two images based upon the ratios dx2:dx1 and dy2:dy1.
3. When the tool is advanced, a new x-ray X1^ is acquired from one of the prior poses, e.g., from the same pose from which the original x-ray X1 was acquired. (Typically, to avoid moving the C-arm, this will be the pose at which the most recent of the previous x-rays was acquired.)

For some applications, the computer processor verifies that there has been no motion of the C-arm with respect to the subject, and/or vice versa, between the acquisitions of X1 and X1^, by comparing the appearance of markers 52 in the two images. For some applications, if there has been movement, then one of the other algorithms described herein is used.

4. The computer processor identifies, by means of image processing, the tip of the tool in image X1^.
5. The computer processor determines how many pixels the tip has moved between the acquisitions of images X1 and X1^.
6. Based upon the 2D relationship between images X1 and X2, and the number of pixels the tip has moved between the acquisitions of images X1 and X1^, the computer processor determines the new location of the tip of the tool in image X2.
7. The computer processor drives the display to display the tool tip (or a representation thereof) at its new location with respect to x-ray image X2.

With reference to FIGS. 19A and 19B, in general, the scope of the present invention includes acquiring 3D image data of a skeletal portion, and acquiring first and second 2D x-ray images, from respective x-ray image views, of the skeletal portion and a portion of a tool configured to be advanced into the skeletal portion along a longitudinal insertion path, while the portion of the tool is disposed at a first location with respect to the insertion path. The location of a portion of the tool with respect to the skeletal portion is identified within the first and second 2D x-ray images, by computer processor 22 of system 20, by means of image processing, and the computer processor registers the 2D x-ray images to the 3D image data, e.g., using the techniques described herein. Thus, a first location of the portion of the tool with respect to the 3D image data is determined. Subsequently, the tool is advanced along the longitudinal insertion path with respect to the skeletal portion, such that the portion of the tool is disposed at a second location along the longitudinal insertion path. Subsequent to moving the portion of the tool to a second location along the insertion path, one or more additional 2D x-ray images of at least the portion of the tool and the skeletal portion are acquired from a single image view. In accordance with respective applications, the single image view is the same as one of the original 2D x-ray image views, or is a third, different 2D x-ray image view. Computer processor 22 of system 20 identifies the second location of the portion of the tool within the one or more additional 2D x-ray images, by means of image processing, and derives the second location of the portion of the tool with respect to the 3D image data, based upon the second location of the portion of the tool within the one or more additional 2D x-ray images, and the determined first location of the portion of the tool with respect to the 3D image data. Typically, an output is generated in response thereto (e.g., by displaying the derived location of the tool relative to the x-ray image view with respect to which the location has been derived).

In accordance with some applications, first and second 2D x-ray images are acquired, from respective x-ray image views, of the skeletal portion and a portion of a tool configured to be advanced into the skeletal portion along a longitudinal insertion path, while the portion of the tool is disposed at a first location with respect to the insertion path. The location of a portion of the tool with respect to the skeletal portion is identified within the first and second 2D x-ray images, by computer processor 22 of system 20, by means of image processing, and the computer processor determines a relationship between the first and second 2D x-ray images, e.g., using any one of algorithms 1-4 described hereinabove. Subsequently, the tool is advanced along the longitudinal insertion path with respect to the skeletal portion, such that the portion of the tool is disposed at a second location along the longitudinal insertion path.

Subsequent to moving the portion of the tool to the second location along the insertion path, one or more additional 2D x-ray images of at least the portion of the tool and the skeletal portion are acquired from a single image view. In accordance with respective applications, the single image view is the same as one of the original 2D x-ray image views, or is a third, different 2D x-ray image view. Computer processor 22 of system 20 identifies the second location of the portion of the tool within the one or more additional 2D x-ray images by means of image processing, and derives the second location of the portion of the tool with respect to one of the original 2D x-ray image views, based upon the second location of the portion of the tool that was identified within the additional 2D x-ray image, and the determined relationship between the first and second 2D x-ray images. Typically, an output is generated in response thereto (e.g., by displaying the derived location of the tool relative to the x-ray image view with respect to which the location has been derived).

Some examples of the applications of the techniques described with reference to FIGS. 19A and 19B are as follows. For an intervention that is performed dorsally, initially x-rays may be acquired from lateral and AP views. Subsequent x-ray may be generally acquired from an AP view only (with optional periodic checks from the lateral view, as described hereinabove), with the updated locations of the tool with respect to the lateral view being derived and displayed. It is noted that although, in this configuration, the C-arm may disturb the intervention, the AP view provides the best indication of the location of the tool relative to the spinal cord. Alternatively, subsequent x-ray may be generally acquired from a lateral view only (with optional periodic checks from the AP view as described hereinabove), with the updated locations of the tool with respect to the AP view being derived and displayed. Typically, for such applications, sets 50 of markers 52 are placed on the patient such that at least one set of markers is visible from the lateral view. Further alternatively, subsequent x-ray may be generally acquired from an oblique view only (with optional periodic checks from the lateral and/or AP view as described hereinabove), with the updated locations of the tool with respect to the AP and/or lateral view being derived and displayed. It is noted that the above applications are presented as examples, and the scope of the present invention includes using the techniques described with reference to FIGS. 19A and 19B with interventions that are performed on any portion of the skeletal anatomy, from any direction of approach, and with any type of x-ray image views, mutatis mutandis.

For some applications, the image of the tool (a representation thereof, and/or a path thereof) as derived from the 2D images is overlaid upon the 3D image data of the vertebra as a hologram. As noted hereinabove, since, in accordance with such applications, the images of the vertebra and the tool (or a representation thereof) are input from different imaging sources, the segmented data of what is the tool (or its representation) and what is the vertebra is in-built (i.e., it is already known to the computer processor). For some applications, the computer processor utilizes this in-built segmentation to allow the operator to virtually manipulate the tool with respect to the vertebra, within the hologram. For example, the operator may virtually advance the tool further along its insertion path, or retract the tool and observe the motion of the tool with respect to the vertebra. Or, the computer processor may automatically drive the holographic display to virtually advance the tool further along its insertion path, or retract the tool. For some applications, similar techniques are applied to other tools and bodily organs, mutatis mutandis. For example, such techniques could be applied to a CT image of the heart in combination with 2D angiographic images of a catheter within the heart.

For some applications, an optical camera is used to acquire optical images of a tool. For example, optical camera 114, which is disposed on x-ray C-arm 34, as shown in FIG. 1, may be used. Alternatively or additionally, an optical camera may be disposed on a separate arm, may be handheld, may be the back camera of a display such as a tablet or mini-tablet device, may be placed on the surgeon's head, may be placed on another portion of the surgeon's body, and/or may be held by another member of the surgical staff. Typically, the computer processor derives the location of the tool with respect to the 3D image data, based upon 2D images in which the tool was observed and using the registration techniques described hereinabove. For some applications, in addition, the computer processor identifies the tool within an optical image acquired by the optical camera. For some such applications, the computer processor then overlays the 3D image data upon the optical image by aligning the location of the tool within the 3D image data and the location of the tool within the optical image. The computer processor then drives an augmented reality display to display the 3D image data overlaid upon the optical image. Such a technique may be performed using any viewing direction of the optical camera within which the tool is visible, and typically without having to track the position of the subject with respect to the optical camera.

For some applications, the location of the tool within the optical image space is determined by using two or more optical cameras, and/or one or more 3D optical cameras. For some applications, even with one 2D optical camera, the 3D image data is overlaid upon the optical image, by aligning two or more tools from each of the imaging modalities. For some applications, even with one 2D optical camera and a single tool, the 3D image data is overlaid upon the optical image, by acquiring additional information regarding the orientation (e.g., rotation) of the tool, and/or the depth of the tool below the skin. For some applications, such information is derived from 3D image data from which the location of the skin surface relative to the vertebra is derived. Alternatively or additionally, such information is derived from an x-ray image in which the tool and the subject's anatomy are visible. Alternatively or additionally, such information is derived from the marker set as seen in an x-ray image in which the tool and the subject's anatomy are visible.

As noted hereinabove, since the images of the vertebra and the tool (or a representation thereof) are input from different imaging sources, the segmented data of what is the tool (or its representation) and what is the vertebra is in-built (i.e., it is already known to the computer processor). For some applications, the computer processor utilizes this in-built segmentation to allow the operator to virtually manipulate the tool with respect to the vertebra, within an augmented reality display. For example, the operator may virtually advance the tool further along its insertion path, or retract the tool and observe the motion of the tool with respect to the vertebra. Or, the computer processor may automatically drive the augmented reality display to virtually advance the tool further along its insertion path, or retract the tool.

Although some applications of the present invention have been described with reference to 3D CT image data, the scope of the present invention includes applying the described techniques to 3D MRI image data. For such applications, 2D projection images (which are geometrically analogous to DRRs that are generated from CT images) are typically generated from the MRI image data and are matched to the 2D images, using the techniques described hereinabove. For some applications, other techniques are used for registering MRI image data to 2D x-ray images. For example, pseudo-CT image data may be generated from the MRI image data (e.g., using techniques as described in "Registration of 2D x-ray images to 3D MRI by generating pseudo-CT data" by van der Bom et al., Physics in Medicine and Biology, Volume 56, Number 4), and the DRRs that are generated from the pseudo-CT data may be matched to the x-ray images, using the techniques described hereinabove.

For some applications, MRI imaging is used during spinal endoscopy, and the techniques described herein (including any one of the steps described with respect to FIG. 7) are used to facilitate performance of the spinal endoscopy. Spinal endoscopy is an emerging procedure that is used, for example, in spinal decompression. By using an endoscope, typically, tools can be inserted and manipulated via a smaller incision relative to current comparable surgery that is used for similar purposes, such that a smaller entry space provides a larger treatment space than in traditional procedures. Typically, such procedures are used for interventions on soft tissue, such as discs. Such tissue is typically visible in MRI images, but is less, or not at all, visible in CT images or in 2D x-ray images. Traditionally, such procedures commence with needle insertion under C-Arm imaging. A series of dilators are then inserted to gradually broaden the approach path. Eventually, an outer tube having a diameter of approximately 1 cm is then kept in place and an endo scope is inserted therethrough. From this point on, the procedure is performed under endoscopic vision.

For some applications, level verification as described hereinabove is applied to a spinal endoscopy procedure in order to determine the location of the vertebra with respect to which the spinal endoscopy is to be performed. Alternatively or additionally, the entry point for the spinal endoscopy may be determined using bidirectional mapping of optical images and x-ray images, as described hereinabove. For some applications, MRI image data are registered to intraprocedural 2D x-ray images. Based upon the registration, additional steps which are generally as described hereinabove are performed. For example, the needle, dilator, and/or endoscope (and/or a representation thereof, and/or a path thereof) may be displayed relative to a target within the MRI image data (e.g., a 3D MRI image, a 2D cross-section derived from 3D MRI image data, and/or a 2D projection image derived from 3D MRI image data). For some applications, endoscopic image data are coregistered to intraprocedural 2D x-ray images. For example, respective endoscopic image data points may be coregistered with respective locations within the intraprocedural images. For some applications, the coregistered endoscopic image data are displayed with the intraprocedural images, together with an indication of the coregistration of respective endoscopic image data points with respective locations within the intraprocedural images. Alternatively or additionally, endoscopic image data are coregistered to MRI image data. For example, respective endoscopic image data points may be coregistered with respective locations within the MRI image data. For some applications, the coregistered endoscopic image data are displayed with the MRI image data, together with an indication of the coregistration of respective endoscopic image data points with respective locations within the MRI image data.

For some applications, the techniques described herein are performed in combination with using a robotic arm, such as a relatively low-cost robotic arm having 5-6 degrees of freedom. In accordance with some applications, the robotic arm is used for holding, manipulating, and/or activating a tool, and/or for operating the tool along a pre-programmed path. For some applications, computer processor 22 drives the robotic arm to perform any one of the aforementioned operations responsively to imaging data, as described hereinabove.

Figure 21A:
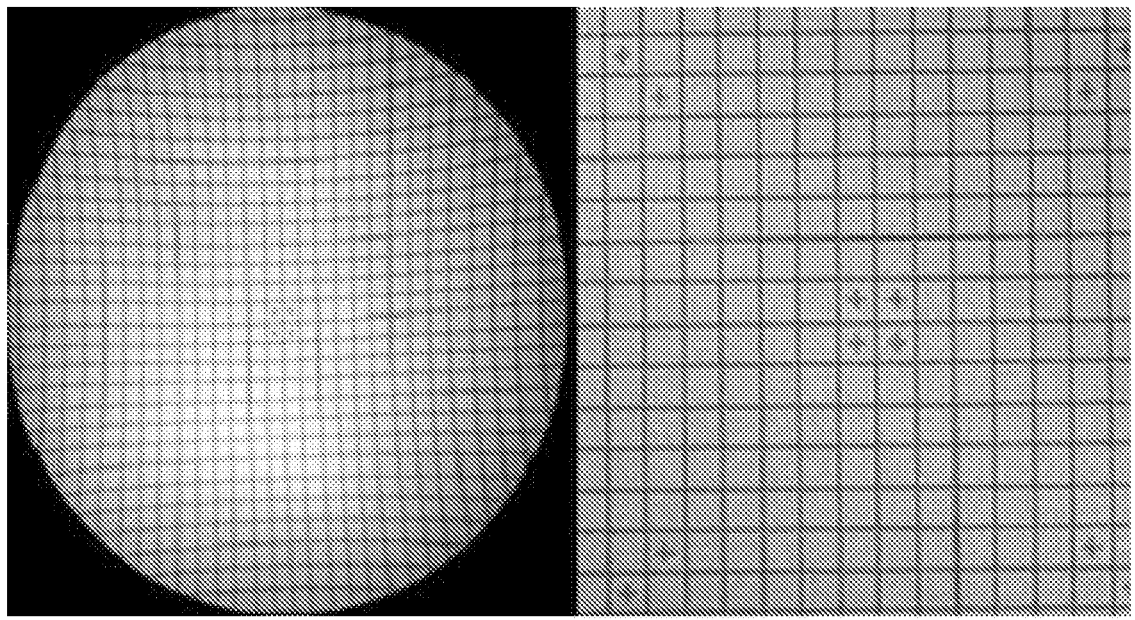
FIG. 21A show examples of x-ray images of a calibration jig generated by a C-arm that uses an image intensifier, and by a C-arm that uses a flat-panel detector, such images reflecting prior art techniques.
Figure 21B:
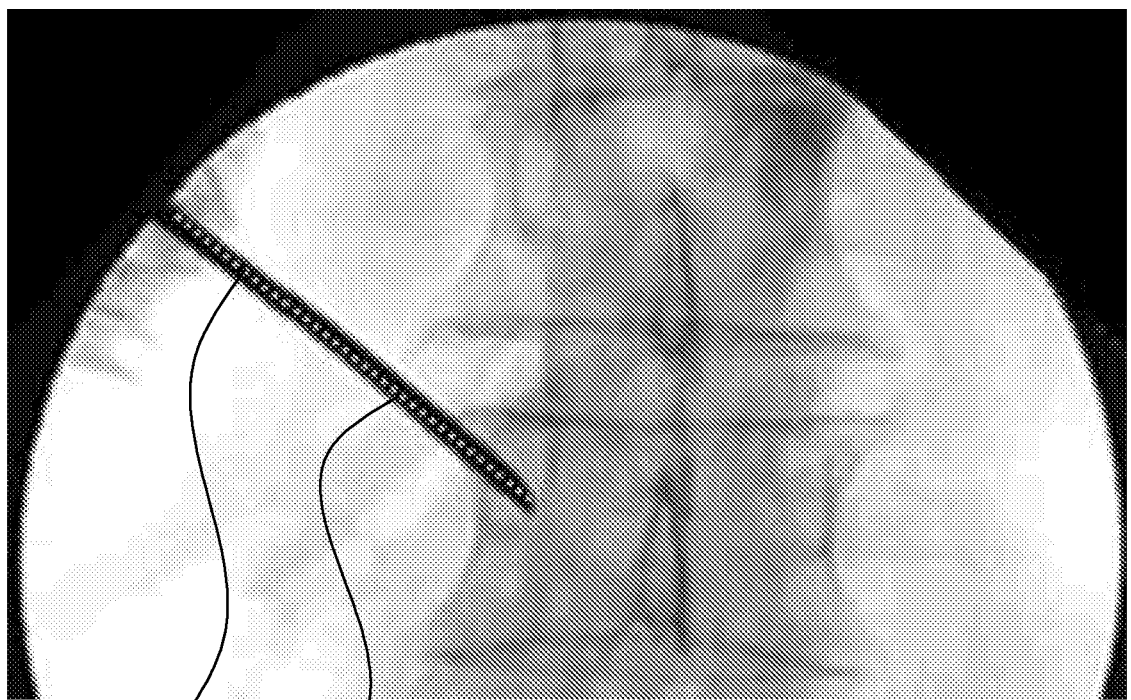
FIG. 21B shows an example of an x-ray image acquired by a C-arm that uses an image intensifier, the image including a radiopaque component that corresponds to a portion of a tool that is known to be straight, and a dotted line overlaid upon the image indicating how a line defined by the straight portion would appear if distortions in the image are corrected, in accordance with some applications of the present invention.

Reference is now made to FIG. 21A, which shows examples of x-ray images of an image calibration jig generated by a C-arm that uses an image intensifier (on the left), and by a C-arm that uses a flat-panel detector (on the right), such images reflecting prior art techniques. Reference is also made to FIG. 21B, which shows an example of an x-ray image acquired by a C-arm that uses an image intensifier, the image including a radiopaque component 200 that corresponds to a portion of a tool that is known to be straight, and a dotted line 210 overlaid upon the image indicating how a line (for example, a centerline) defined by the straight portion would appear if distortions in the image are corrected, in accordance with some applications of the present invention.

As may be observed in the example shown in FIG. 21A, in x-ray images generated by a C-Arm that uses an image intensifier, there is typically image distortion, which increases toward the periphery of the image. By contrast, in images generated using a flat-panel detector, there is typically no distortion. For some applications of the present invention, distortions in x-ray images generated by a C-Arm that uses an image intensifier are at least partially corrected automatically, by means of image processing. For example, the distortion of such images may be corrected in order to then register the corrected image to a 3D image data, using the techniques described hereinabove.

Referring to FIG. 21B, for some applications such an x-ray image is at least partially corrected by computer processor 22 identifying, by means of image processing, a radiopaque component 200 of an instrument within a portion of the radiographic image. For some applications, the radiopaque component is a portion of the tool that is known to be straight, a component having a different known shape, and/or two or more features that are disposed in known arrangement with respect to one another. For example, the straight shaft of a Jamshidi™ needle may be identified.

For some applications, in order to at least partially correct an x-ray image comprising a radiopaque component that is known to be straight, the computer processor uses techniques for automatically identifying a centerline of an object, for example, as described in US 2010-0161022 to Tolkowsky, which is incorporated herein by reference, to generate a centerline of said component. Typically, the computer processor then at least partially corrects the image distortion, in at least a portion of the image in which the component that is known to be straight is disposed, by deforming the portion of the radiographic image, such that the centerline of the radiopaque component of the instrument that is known to be straight appears straight within the radiographic image. FIG. 19B shows an example of how an x-ray image, prior to correcting its distortion, comprises component 200 that is known to be straight and yet does not appear straight within the image, as can be observed relative to straight line 210. For some applications, two or more such components are identified in respective portions of the image, and distortion of those portions of the image are corrected accordingly. For some applications, distortions in portions of the image in which no such components are disposed are corrected, based upon distortion correction parameters that are determined by means of the radiopaque component that is known to be straight, or known to have a different known shape.

For some applications of the present invention, techniques described hereinabove are combined with a system that determines the location of the tip of a tool with respect to a portion of the subject's body by (a) calculating a location of a proximal portion of the tool that is disposed outside the subject's body, and (b) based upon the calculated position of the proximal portion of the tool, deriving a location of a tip of the tool with respect to the portion of the subject's body with respect to the 3D image data. For example, such techniques may be used with a navigation system that, for example, may include the use of one or more location sensors that are attached to a portion of a tool that is typically disposed outside the subject's body even during the procedure. (It is noted that the location sensors that are disposed upon the tool may be sensors that are tracked by a tracker that is disposed elsewhere, or they may be a tracker that tracks sensors that are disposed elsewhere, and thereby acts a location sensor of the tool.) For example, a tool may be inserted into the subject's vertebra, such that its distal tip (or a distal portion of the tool) is disposed inside the vertebra, and a location sensor may be disposed on a proximal portion of the tool that is disposed outside the subject's body. The navigation system typically derives the location of the tip of the tool (or a distal portion of the tool), by detecting the location(s) of the location sensor(s) that are disposed on the proximal portion of the tool, and then deriving the location of the tip of the tool (or a distal portion of the tool) based upon an assumed location of the distal tip of the tool (or a distal portion of the tool) relative to the location sensor(s). The navigation system then overlays the derived location of the tip of the tip of the tool (or a distal portion of the tool) with respect to the vertebra upon previously acquired 3D image data (e.g., images acquired prior to the subject being placed in the operating room, or when the subject was in the operating room, but typically prior to the commencement of the intervention). Alternatively or additionally, the location of a proximal portion of the tool that is disposed outside the subject's body may be calculated by video tracking the proximal portion of the tool, and/or by means of tracking motion of a portion of a robot to which the proximal portion of the tool is coupled, relative to a prior known position, e.g., based upon the values of the joints of the robot relative to the corresponding values of the joints of the robot at the prior known position.

In such cases, there may be errors associated with determining the location of the tip of the tool (or a distal portion of the tool), based upon the assumed location of the distal tip of the tool (or a distal portion of the tool) relative to the location sensor(s) being erroneous, e.g., due to slight bending of the tool upon being inserted into the vertebra. Therefore, for some applications, during the procedure, typically periodically, 2D x-ray images are acquired within which the actual tip of tool (or distal portion of the tool) within the vertebra is visible. The location of the tip of the tool (or distal portion of the tool) with respect to the vertebra as observed in the 2D x-ray images is determined with respect to the 3D image data, by registering the 2D x-ray images to the 3D image data. For example, the 2D x-ray images may be registered to the 3D image data using techniques described hereinabove. In this manner, the actual location of the tip of the tool (or distal portion of the tool) with respect to the vertebra is determined with respect to the 3D image data. For some applications, in response thereto, errors in the determination of the location of the tip of the tool (or distal portion of the tool) with respect to the vertebra within the 3D image space resulting from the navigation system, are periodically corrected by system 20. For example, based upon the determined location of at least the tip of the tool (or distal portion of the tool), the computer processor may drive the display to update the indication of the location of the tip of the tool (or distal portion of the tool) with respect to the vertebra with respect to the 3D image data. For some applications, the navigation systems comprise the use of augmented reality, or virtual reality, or robotic manipulation of tools, or any combination thereof.

By way of illustration and not limitation, it is noted that the scope of the present invention includes applying the apparatus and methods described herein to any one of the following applications:

Multiple tool insertions (e.g., towards both pedicles) in the same vertebra.

Any type of medical tool or implant, including, Jamshidi™ needles, k-wires, pedicle markers, screws, endoscopes, RF probes, laser probes, injection needles, etc.

An intervention that is performed from a lateral approach, in which case the functional roles of the AP and lateral x-ray views described hereinabove are typically switched with one another.

Interventions using x-ray views other than lateral and AP views as an alternative or in addition to such views. For example, oblique imaging views may be used.

An intervention that is performed from an anterior, oblique and/or posterior interventional approach.

Interventions performed upon multiple vertebrae. Even for such cases, the intra-operative x-ray images of the vertebrae are typically registered with the 3D image data of the corresponding vertebrae on an individual basis.

Interventions performed on discs in between vertebrae.

Interventions performed on nerves.

Tool insertion under x-ray in a video imaging mode.

Use of certain features of system 20 utilizing intraprocedural 2D x-ray imaging, but without utilizing preprocedural 3D imaging.

Use of certain features of system 20 without some or all of the above-described disposable items, such as drape 53.

Various orthopedic surgeries, such as surgeries performed on limbs and/or joints.

Interventions in other body organs.

For some applications system 20 includes additional functionalities to those described hereinabove. For example, the computer processor may generate an output that is indicative of a current level of accuracy (e.g., of verification of the vertebral level, determination of the insertion site, and/or registration of the 3D image data to the 2D images), e.g., based upon a statistical calculation of the possible error. For some applications, the computer processor generates a prompt indicating that a new x-ray from one or more views should be acquired. For example, the computer processor may generate such a prompt based on the time elapsed since a previous x-ray acquisition from a given view, and/or based on the distance a tool has moved since a previous x-ray acquisition from a given view, and/or based on observed changes in the position of markers 52 relative to the C-arm.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 22. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., computer processor 22) coupled directly or indirectly to memory elements (such as memory 24) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that blocks of the flowchart shown in FIGS. 7, 14A, and 14B, combinations of blocks in the flowcharts, as well as any one of the algorithms described herein, can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 22) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 22 and the other computer processors described herein are typically hardware devices programmed with computer program instructions to produce a special purpose computer. For example, when programmed to perform the algorithms described herein, the computer processor typically acts as a special purpose skeletal-surgery-assisting computer processor. Typically, the operations described herein that are performed by computer processors transform the physical state of a memory, which is a real physical article, to have a different magnetic polarity, electrical charge, or the like depending on the technology of the memory that is used.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for performing a procedure using a tool that has at least one radiopaque feature, the tool being configured to be advanced into a skeletal portion within a body of a subject along a longitudinal insertion path, the method comprising:
    acquiring 3D image data of the skeletal portion;
    while a portion of the tool is disposed at a first location along the longitudinal insertion path with respect to the skeletal portion, sequentially:
    acquiring a first 2D x-ray image of at least the portion of the tool and the skeletal portion from a first view, using a 2D x-ray imaging device that is unregistered with respect to the subject's body and that is disposed at a first pose with respect to the subject's body;
    moving the 2D x-ray imaging device to a second pose with respect to the subject's body; and
    while the 2D x-ray imaging device is at the second pose, acquiring a second 2D x-ray image of at least the portion of the tool and the skeletal portion from a second view;
    using at least one computer processor:
    registering the first and second x-ray images to the 3D image data, the registering comprising:
    generating a plurality of 2D projections from the 3D image data, and
    identifying respective first and second 2D projections that match the first and second 2D x-ray images of the skeletal portion;
    identifying a location of the portion of the tool with respect to the skeletal portion within the first and second 2D x-ray images, using the at least one radiopaque feature of the tool, by means of image processing;
    based upon the identified location of the portion of the tool within the first and second 2D x-ray images, and the registration of the first and second 2D x-ray images to the 3D image data, determining the first location of the portion of the tool with respect to the 3D image data;
    subsequently, moving the portion of the tool to a second location along the longitudinal insertion path with respect to the skeletal portion;
    subsequent to moving the portion of the tool to the second location, acquiring one or more additional 2D x-ray images of at least the portion of the tool and the skeletal portion from a single image view;
    using the computer processor:
    identifying the second location of the portion of the tool within the one or more additional 2D x-ray images, using the at least one radiopaque feature of the tool, by means of image processing;
    deriving the second location of the portion of the tool with respect to the 3D image data, based upon the second location of the portion of the tool within the one or more additional 2D x-ray images, and the determined first location of the portion of the tool with respect to the 3D image data; and
    generating an output, at least partially in response thereto.

2. The method according to claim 1, wherein acquiring the one or more additional 2D x-ray images of at least the portion of the tool and the skeletal portion from the single image view comprises acquiring the one or more additional 2D x-ray image of at least the portion of the tool and the skeletal portion from one of the first and second image views.

3. The method according to claim 1, wherein acquiring the one or more additional 2D x-ray images of at least the portion of the tool and the skeletal portion comprises acquiring the one or more additional 2D x-ray images of at least the portion of the tool and the skeletal portion from a third image view that is different from the first and second image views.

4. A method for performing a procedure using a tool that has at least one radiopaque feature, the tool being configured to be advanced into a skeletal portion within a body of a subject along a longitudinal insertion path, the method comprising:
   acquiring 3D image data of the skeletal portion;
   while a portion of the tool is disposed at a location along the longitudinal insertion path, sequentially:
   acquiring a first 2D x-ray image of at least the portion of the tool and the skeletal portion from a first view, using a 2D x-ray imaging device that is unregistered with respect to the subject's body and that is disposed at a first pose with respect to the subject's body;
   moving the 2D x-ray imaging device to a second pose with respect to the subject's body; and
   while the 2D x-ray imaging device is at the second pose, acquiring a second 2D x-ray image of at least the portion of the tool and the skeletal portion from a second view;
   using at least one computer processor:
   registering the first and second 2D x-ray images to the 3D image data, the registering comprising:
   generating a plurality of 2D projections from the 3D image data, and
   identifying respective first and second 2D projections that match the first and second 2D x-ray images;
   identifying the location of the portion of the tool with respect to the skeletal portion, within the first and second x-ray images, using the at least one radiopaque feature of the tool, by means of image processing;
   based upon the identified location of the portion of the tool within the first and second x-ray images, and the registration of the first and second 2D x-ray images to the 3D image data, deriving a relationship between the location of the portion of the tool with respect to the 3D image data and a given location within the 3D image data; and
   generating an output that is indicative of the relationship between the location of the portion of the tool with respect to the 3D image data and the given location within the 3D image data.

5. The method according to claim 4, wherein generating the output that is indicative of the relationship between the location of the portion of the tool with respect to the 3D image data and the given location within the 3D image data comprises generating the output upon a 2D cross-section of the skeletal portion that is derived from the 3D image data.

6. The method according to claim 4, wherein generating the output that is indicative of the relationship between the location of the portion of the tool with respect to the 3D image data and the given location within the 3D image data comprises generating the output upon a 2D projection of the skeletal portion that is derived from the 3D image data.

7. The method according to claim 4, wherein generating the output that is indicative of the relationship between the location of the portion of the tool with respect to the 3D image data and the given location within the 3D image data comprises generating the output upon a 3D image of the skeletal portion that is derived from the 3D image data.

8. The method according to claim 4, wherein deriving the relationship between the location of the portion of the tool with respect to the 3D image data and the given location within the 3D image data comprises deriving an anticipated longitudinal insertion path of the tool with respect to the given location within the 3D image data.

9. The method according to claim 4, wherein deriving the relationship between the location of the portion of the tool with respect to the 3D image data and the given location within the 3D image data comprises deriving a relationship between the location of the portion of the tool with respect to the 3D image data and a predesignated target location within the 3D image data.

10. The method according to claim 4, wherein deriving the relationship between the location of the portion of the tool with respect to the 3D image data and the given location within the 3D image data comprises deriving a relationship between the location of the portion of the tool with respect to the 3D image data with respect to respective volumes within the 3D image data, the respective volumes designating respective levels of acceptability of protrusion of the tool or another tool with respect to the respective volumes.

11. The method according to claim 4, wherein generating the output that is indicative of the relationship between the location of the portion of the tool with respect to the 3D image data and the given location within the 3D image data comprises generating the output upon a 2D x-ray image that is registered with the 3D image data.

12. The method according to claim 4, wherein generating the output that is indicative of the relationship between the location of the portion of the tool with respect to the 3D image data and the given location within the 3D image data comprises generating the output upon at least one of the first and second 2D x-ray images.

* * * * *